(12) United States Patent
Choe et al.

(10) Patent No.: US 7,834,258 B2
(45) Date of Patent: Nov. 16, 2010

(54) DIMER OF CHIMERIC RECOMBINANT BINDING DOMAIN-FUNCTIONAL GROUP FUSION FORMED VIA DISULFIDE-BOND-BRIDGE AND THE PROCESSES FOR PRODUCING THE SAME

(75) Inventors: Mu-Hyeon Choe, 15-1205, Dongsung 3 cha Apt., Sinnae 1-dong, Jungnang-gu, Seoul 131-131 (KR); Seong-Hyeok Choi, Gongju-si (KR); Yong-Chan Lee, Seosan-si (KR); Hye-Won Kwon, Seoul (KR); Jae-Seon Won, Seoul (KR); Mi-Hyun Yu, Seoul (KR); Jeong-Hwa Song, Seoul (KR); Yong-Jae Kim, Seoul (KR)

(73) Assignee: Mu-Hyeon Choe, Seoul (KR)

( * ) Notice: Subject to any disclaimer, the term of this patent is extended or adjusted under 35 U.S.C. 154(b) by 0 days.

(21) Appl. No.: 10/562,627

(22) PCT Filed: Jun. 30, 2004

(86) PCT No.: PCT/KR2004/001595

§ 371 (c)(1),
(2), (4) Date: Dec. 22, 2005

(87) PCT Pub. No.: WO2005/000902

PCT Pub. Date: Jan. 6, 2005

(65) Prior Publication Data

US 2007/0009987 A1 Jan. 11, 2007

(30) Foreign Application Priority Data

Jun. 30, 2003 (KR) .................. 10-2003-0043599

(51) Int. Cl.
*C12P 21/02* (2006.01)
*C12N 9/00* (2006.01)
*C07K 16/00* (2006.01)
*A61K 38/17* (2006.01)

(52) U.S. Cl. ................ 930/310; 435/69.7; 435/183; 530/387.1; 514/12

(58) Field of Classification Search ................ 930/310; 435/69.7, 183; 530/387.1; 514/12
See application file for complete search history.

(56) References Cited

U.S. PATENT DOCUMENTS 4,956,453 A 9/1990 Bjorn et al.

FOREIGN PATENT DOCUMENTS

EP 501215 A2 * 9/1992

OTHER PUBLICATIONS

Ogata et al., "Processing of *Pseudomonas* exotoxin by a cellular protease results in the generation of a 37,000-Da toxin fragment that is translocated to the cytosol," J Biol Chem 265(33):20678-20685, 1990.*
B. Pastan, I., et al., Science 254, pp. 1173-1177, 1991.

(Continued)

*Primary Examiner*—Karen Cochrane Carlson
*Assistant Examiner*—Rosanne Kosson
(74) *Attorney, Agent, or Firm*—Lucas & Mercanti, LLP

(57) ABSTRACT

The present invention relates to a method producing dimer of chimeric recombinant binding domain-heterogeneous functional group fusion([B-F fusion]$_2$) by using covalent disulfide-bond-bridge connecting the two monomers of chimeric recombinant binding domain-heterogeneous functional group fusion(B-F fusion). The dimer of chimeric recombinant binding domain(B)-heterogeneous functional group(F) fusion was the first to be formed by using covalent disulfide-bond-bridge to connect monomers to have double binding valency of the monomer. It has higher functional efficiency to its targets and the production yield is high by containing said extension peptide chain.

5 Claims, 13 Drawing Sheets

OTHER PUBLICATIONS

B. Brinkmann, U., et al., J. Mol. Biol., vol. 268, pp. 107-117, 1997.
B. Buchner, J., et al., Anal Biochem., vol. 205, pp. 263-270, 1992.
B. Choe, M., et al., Cancer Res., vol. 54, pp. 3460-3467, 1994.
B. Takemura S., et al., Cancer Immunol Immunother., vol. 51(1), pp. 33-44, 2002.
B. Bera, T.K., et al., Bioconjug Chem. vol. 9(6), pp. 736-744, 1998.
B. Choi, S., et al., Bull. Korean. Chem. Soc., vol. 22(12), pp. 1361-1365, 2001.
B. Park, J., et al., Mol. Cells, vol. 12(3), pp. 398-402, 2001.

* cited by examiner

The position of Cysteine on extension peptide chain (a) Fd, Fc fragment PCR from pMC74 and pcDNA3Cγ1

(b) Splicing PCR amplification by overlap extension (c) Insert of pLSC52 encoding B3(Fd-Fc)-PE38R (a) Fd, CH3 fragment PCR from pLSC52

(b) Splicing PCR amplification by overlap extension (c) Insert of pLSC32 encoding B3(Fd-CH3)-PE38R

```
                        SEQUENCE LISTING

<160> NUMBER OF SEQ ID NOS: 59

<210> SEQ ID NO 1
<211> LENGTH: 1749
<212> TYPE: DNA
<213> ORGANISM: Artificial Sequence
<220> FEATURE:
<223> OTHER INFORMATION: pMC74 plasmid coding sequence

<400> SEQUENCE: 1
atggatgtga agctggtgga atctggagga ggcttagtgc agcctggagg gtccctgaaa      60
ctctcctgtg caacctctgg attcactttc agtgactatt acatgtattg ggttcgccag     120
actccagaga gaggctgga gtgggtcgca tacattagta tgatgatag ttccgccgct       180 tattcagaca ctgtaaaggg ccggttcacc atctccagag acaatgccag gaacaccctc     240
tacctgcaaa tgagccgtct gaagtctgag gacacagcca tatattcctg tgcaagagga     300
ctggcctggg gagcctggtt tgcttactgg ggccaaggga ctctggtcac tgtctctgca     360
gccaaaacga cccccccatc tgtctatcca ctggcccctg gatctgctgc ccaaactaac     420
tccatggtga ccctgggatg cctggtcaag ggctatttcc ctgagccagt gacagtgacc     480
tggaactctg gatccctgtc cagcggtgtg cacaccttcc cagctgtcct gcagtctgac     540
ctctacactc tgagcagctc agtgactgtc ccctccagca cctggcccag cgagaccgtc     600
acctgcaacg ttgcccaccc ggccagcagc accaaggtgg acaagaaaat tgtgcccagg     660
gattgtggta gtaagcctag cataagtaca aaagcttccg gaggtcccga gggcggcagc     720
ctggccgcgc tgaccgcgca ccaggcttgc cacctgccgc tggagacttt cacccgtcat     780
cgccagccgc gcggctggga acaactggag cagtgcggct atccggtgca gcggctggtc     840
gccctctacc tggcggcgcg gctgtcgtgg aaccaggtcg accaggtgat ccgcaacgcc     900
ctggccagcc ccggcagcgg cggcgacctg ggcgaagcga tccgcgagca gccggagcag     960
```

-continued

```
gcccgtctgg ccctgaccct ggccgccgcc gagagcgagc gcttcgtccg gcagggcacc    1020
ggcaacgacg aggccggcgc ggccaacggc ccggcggaca gcggcgacgc cctgctggag    1080
cgcaactatc ccactggcgc ggagttcctc ggcgacggcg cgacgtcag cttcagcacc     1140
cgcggcacgc agaactggac ggtggagcgg ctgctccagg cgcaccgcca actggaggag    1200
cgcggctatg tgttcgtcgg ctaccacggc accttcctcg aagcggcgca aagcatcgtc    1260
ttcggcgggg tgcgcgcgcg cagccaggac ctcgacgcga tctggcgcgg tttctatatc    1320
gccggcgatc cggcgctggc ctacggctac gcccaggacc aggaacccga cgcacgcggc    1380
cggatccgca acggtgccct gctgcgggtc tatgtgccgc gctcgagcct gccgggcttc    1440
taccgcacca gcctgaccct ggccgcgccg gaggcggcgg gcgaggtcga acggctgatc    1500
ggccatccgc tgccgctgcg cctggacgcc atcaccggcc ccgaggagga aggcgggcgc    1560
ctggagacca ttctcggctg gccgctggcc gagcgcaccg tggtgattcc ctcggcgatc    1620
cccaccgacc cgcgcaacgt cggcggcgac ctcgacccgt ccagcatccc cgacaaggaa    1680
caggcgatca gcgccctgcc ggactacgcc agccagcccg gcaaaccgcc gcgcgaggac    1740
ctgaagtaa                                                            1749
```

<210> SEQ ID NO 2
<211> LENGTH: 1764
<212> TYPE: DNA
<213> ORGANISM: Artificial Sequence
<220> FEATURE:
<223> OTHER INFORMATION: pMH21 plasmid coding sequence

<400> SEQUENCE: 2

```
atggaggtga agctggtgga atctggagga ggcttagtgc agcctggagg gtccctgaaa      60
ctctcctgtg caacctctgg attcactttc agtgactatt acatgtattg ggttcgccag     120
actccagaga gaggctggga gtgggtcgca tacattagta atgatgatag ttccgccgct     180
tattcagaca ctgtaaaggg ccggttcacc atctccagag acaatgccag gaacacccct     240
tacctgcaaa tgagccgtct gaagtctgag gacacagcca tatattcctg tgcaagagga     300
ctggcctggg agcctggtt tgcttactgg ggccaaggga ctctggtcac tgtctctgca     360
gccaaaacga caccccatc tgtctatcca ctggcccctg gatctgctgc ccaaactaac     420
tccatggtga ccctgggatg cctggtcaag ggctatttcc ctgagccagt gacagtgacc     480
tggaactctg gatccctgtc cagcggtgtg cacaccttcc cagctgtcct gcagtctgac     540
ctctacactc tgagcagctc agtgactgtc ccctccagca cctggcccag cgagaccgtc     600
acctgcaacg ttgcccaccc ggccagcagc accaaggtgg acaagaaaat tgtgcccagg     660
gattgtggta gtaagccttg cataagtaca aaagcttctg tggtggcgg atctggaggt     720
cccgagggcg gcagcctggc cgcgctgacc gcgcaccagg cttgccacct gccgctggag     780
actttcaccc gtcatcgcca gccgcgcggc tgggaacaac tggagcagtg cggctatccg     840
gtgcagcggc tggtcgccct ctacctggcg gcgcggctgt cgtggaacca ggtcgaccag    900
gtgatccgca acgccctggc cagccccggc agcggcggcg acctgggcga agcgatccgc    960
gagcagccgg agcaggcccg tctggccctg accctggccg ccgccgagag cgagcgcttc   1020
gtccggcagg gcaccggcaa cgacgaggcc ggcgcggcca acggcccggc ggacagcggc   1080
gacgccctgc tggagcgcaa ctatcccact ggcgcggagt tcctcggcga cggcggcgac   1140
gtcagcttca gcacccgcgg cacgcagaac tggacggtgg agcggctgct ccaggcgcac   1200
```

```
cgccaactgg aggagcgcgg ctatgtgttc gtcggctacc acggcaccttc cctcgaagcg    1260 gcgcaaagca tcgtcttcgg cggggtgcgc gcgcgcagcc aggacctcga cgcgatctgg    1320
cgcggtttct atatcgccgg cgatccggcc ctggcctacg gctacgccca ggaccaggaa    1380
cccgacgcac gcggccggat ccgcaacggt gccctgctgc gggtctatgt gccgcgctcg    1440
agcctgccgg gcttctaccg caccagcctg accctggccg cgccggaggc ggcgggcgag    1500
gtcgaacggc tgatcggcca tccgctgccg ctgcgcctgg acgccatcac cggccccgag    1560
gaggaaggcg ggcgcctgga gaccattctc ggctggccgc tggccgagcg caccgtggtg    1620
attccctcgg cgatccccac cgacccgcgc aacgtcggcg cgacctcga cccgtccagc     1680 atccccgaca aggaacaggc gatcagcgcc ctgccggact acgccagcca gcccggcaaa    1740
ccgccgcgcg aggacctgaa gtaa                                            1764

<210> SEQ ID NO 3
<211> LENGTH: 1749
<212> TYPE: DNA
<213> ORGANISM: Artificial Sequence
<220> FEATURE:
<223> OTHER INFORMATION: pCE2 plasmid coding sequence

<400> SEQUENCE: 3
atggatgtga agctggtgga atctggagga ggcttagtgc agcctggagg gtccctgaaa      60
ctctcctgtg caacctctgg attcactttc agtgactatt acatgtattg ggttcgccag     120
actccagaga gaggctgga gtgggtcgca tacattagta atgatgatag ttccgccgct     180
tattcagaca ctgtaaaggg ccggttcacc atctccagag acaatgccag gaacaccctc     240
tacctgcaaa tgagccgtct gaagtctgag gacacagcca tatattcctg tgcaagagga     300
ctggcctggg agcctggttt gcttactggg gccaaggga ctctggtcac tgtctctgca     360
gccaaaacga caccccatc tgtctatcca ctggcccctg gatctgctgc ccaaactaac     420
tccatggtga ccctgggatg cctggtcaag ggctatttcc ctgagccagt gacagtgacc     480
tggaactctg gatccctgtc cagcggtgtg cacaccttcc cagctgtcct gcagtctgac     540
ctctacactc tgagcagctc agtgactgtc ccctccagca cctggcccag cgagaccgtc     600
acctgcaacg ttgcccaccc ggccagcagc accaaggtgg acaagaaaat tgtgcccagg     660
gattgtggta gtaagccttg cataagtaca aaagcttccg gaggtcccga gggcggcagc     720
ctggccgcgc tgaccgcgca ccaggcttgc cacctgccgc tggagacttt cacccgtcat     780
cgccagccgc gcggctggga caactggag cagtgcggct atccggtgca gcggctggtc     840
gccctctacc tggcggcgcg gctgtcgtgg aaccaggtcg accaggtgat ccgcaacgcc     900
ctggccagcc ccgcagcggc cggcgacctg gcgaagcga tccgcgagca gccggagcag     960
gcccgtctgg ccctgaccct ggccgccgcc gagagcgagc gcttcgtccg gcagggcacc    1020
ggcaacgacg aggccggcgc ggccaacggc ccggcggaca cgggcgacgc cctgctggag    1080
cgcaactatc ccactggcgc ggagttcctc ggcgacggcg cgacgtcag cttcagcacc     1140 cgcggcacgc agaactggac ggtggagcgg ctgctccagg cgcaccgcca actggaggag    1200
cgcggctatg tgttcgtcgg ctaccacggc accttcctcg aagcggcgca aagcatcgtc    1260
ttcggcgggg tgcgcgcgcg cagccaggac ctcgacgcga tctggcgcgg tttctatatc    1320
gccggcgatc cggcgctggc ctacggctac gcccaggacc aggaacccga cgcacgcggc    1380
cggatccgca acggtgccct gctgcgggtc tatgtgccgc gctcgagcct gccgggcttc    1440
taccgcacca gcctgaccct ggccgcgccg gaggcggcgg gcgaggtcga acggctgatc    1500
```

-continued

```
ggccatccgc tgccgctgcg cctggacgcc atcaccggcc cgaggagga aggcgggcgc    1560 ctggagacca ttctcggctg gccgctggcc gagcgcaccg tggtgattcc ctcggcgatc    1620
cccaccgacc gcgcaacgt cggcggcgac ctcgacccgt ccagcatccc cgacaaggaa    1680
caggcgatca gcgccctgcc ggactacgcc agccagcccg gcaaaccgcc gcgcgaggac    1740
ctgaagtaa                                                             1749

<210> SEQ ID NO 4
<211> LENGTH: 672
<212> TYPE: DNA
<213> ORGANISM: Artificial Sequence
<220> FEATURE:
<223> OTHER INFORMATION: pMC75 plasmid coding sequence

<400> SEQUENCE: 4
atggatgtgc tgatgaccca gtctccattg agtttacctg tcagtcttgg agatcaagcc      60
tccatctctt gcagatctag tcagatcatt gtacatagta atggaaacac ctatttagaa     120
tggtacctgc agaaaccagg ccagtctcca aagctcctga tctacaaagt ttccaaccga     180
ttttctgggg tcccagacag gttcagtggc agtggatcag ggacagattt cacactcaag     240
atcagcagag tggaggctga ggatctggga gtttattact gctttcaagg ttcacatgtt     300
ccattcacgt tcggctcggg gacaaagttg gaaataaaac gggctgatgc tgcaccaact     360
gtatccatct tcccaccatc cagtgagcag ttaacatctg gaggtgcctc agtcgtgtgc     420
ttcttgaaca acttctaccc caaagacatc aatgtcaagt ggaagattga tggcagtgaa     480
cgacaaaatg gcgtcctgaa cagttggact gatcaggaca gcaaagacag cacctacagc     540
atgagcagca ccctcacgtt gaccaaggac gagtatgaac gacataacag ctatacctgt     600
gaggccactc acaagacatc aacttcaccc attgtcaaga gcttcaacag gaatgagtgt     660
ggtaaagctt aa                                                         672

<210> SEQ ID NO 5
<211> LENGTH: 2454
<212> TYPE: DNA
<213> ORGANISM: Artificial Sequence
<220> FEATURE:
<223> OTHER INFORMATION: pLSC52 plasmid coding sequence

<400> SEQUENCE: 5
atggatgtga agctggtgga atctggagga ggcttagtgc agcctggagg gtccctgaaa      60
ctctcctgtg caacctctgg attcactttc agtgactatt acatgtattg ggttcgccag     120
actccagaga gaggctgga gtgggtcgca tacattagta atgatgatag ttccgccgct     180
tattcagaca ctgtaaaggg ccggttcacc atctccagag acaatgccag gaacaccctc     240
tacctgcaaa tgagccgtct gaagtctgag gacacagcca tatattcctg tgcaagagga     300
ctggcctggg gagcctggtt tgcttactgg ggccaaggga ctctggtcac tgtctctgca     360
gccaaaacga cacccccatc tgtctatcca ctggcccctg gatctgctgc ccaaactaac     420
tccatggtga ccctgggatg cctggtcaag ggctatttcc ctgagccagt gacagtgacc     480
tggaactctg gatccctgtc cagcggtgtg cacaccttcc cagctgtcct gcagtctgac     540
ctctacactc tgagcagctc agtgactgtc ccctccagca cctggcccag cgagaccgtc     600
acctgcaacg ttgcccaccc ggccagcagc accaaggtgg acaagaaaat tgtgcccagg     660
gattgtggtg agcccaaatc ttgtgacaaa actcacacat gcccaccgtg cccagcacct     720
```

```
gaactcctgg ggggaccgtc agtcttcctc ttccccccaa aacccaagga caccctcatg        780
atctcccgga cccctgaggt cacatgcgtg gtggtggacg tgagccacga agaccctgag        840
gtcaagttca actggtacgt ggacggcgtg gaggtgcata atgccaagac aaagccgcgg        900
gaggagcagt acaacagcac gtaccgtgtg gtcagcgtcc tcaccgtcct gcaccaggac        960
tggctgaatg gcaaggagta caagtgcaag gtctccaaca aagccctccc agcccccatc       1020
gagaaaacca tctccaaagc caagggcag ccccgagaac acaggtgta caccctgccc         1080 ccatcccggg atgagctgac caagaaccag gtcagcctga cctgcctggt caaaggcttc       1140
tatcccagcg acatcgccgt ggagtgggag agcaatgggc agccggagaa caactacaag       1200
accacgcctc ccgtgctgga ctccgacggc tccttcttcc tctacagcaa gctcaccgtg       1260
gacaagagca ggtggcagca ggggaacgtc ttctcatgct ccgtgatgca tgaggctctg       1320
cacaaccact acacgcagaa gagcctctcc ctgtctccgg gtaaaggcgg aggcggatcc       1380
ggtggtggcg gttctaaagc ttccggaggt cccgagggcg cagcctggc cgcgctgacc        1440 gcgcaccagg cttgccacct gccgctggag actttcaccc gtcatcgcca gccgcgcggc       1500
tgggaacaac tggagcagtg cggctatccg gtgcagcggc tggtcgccct ctacctggcg       1560
gcgcggctgt cgtggaacca ggtcgaccag gtgatccgca acgccctggc cagccccggc       1620
agcggcggcg acctgggcga agcgatccgc gagcagccgg agcaggcccg tctggccctg       1680
accctggccg ccgccgagag cgagcgcttc gtccggcagg gcaccggcaa cgacgaggcc       1740
ggcgcggcca acgcccggc ggacagcggc gacgccctgc tggagcgcaa ctatcccact        1800
ggcgcggagt tcctcggcga cggcggcgac gtcagcttca gcacccgcgg cacgcagaac       1860
tggacggtgg agcggctgct ccaggcgcac cgccaactgg aggagcgcgg ctatgtgttc       1920
gtcggctacc acggcacctt cctcgaagcg gcgcaaagca tcgtcttcgg cggggtgcgc       1980
gcgcgcagcc aggacctcga cgcgatctgg cgcggtttct atatcgccgg cgatccggcg       2040
ctggcctacg gctacgccca ggaccaggaa cccgacgcac gcggccggat ccgcaacggt       2100
gccctgctgc gggtctatgt gccgcgctcg agcctgccgg gcttctaccg caccagcctg       2160
accctggccg cgccggaggc ggcgggcgag gtcgaacggc tgatcggcca tccgctgccg       2220
ctgcgcctgg acgccatcac cggccccgag gaggaaggcg ggcgcctgga gaccattctc       2280
ggctggccgc tggccgagcg caccgtggtg attccctcgg cgatccccac cgacccgcgc       2340
aacgtcggcg gcgacctcga cccgtccagc atccccgaca aggaacaggc gatcagcgcc       2400
ctgccggact acgccagcca gcccggcaaa ccgccgcgcg aggacctgaa gtaa            2454
```

<210> SEQ ID NO 6
<211> LENGTH: 1233
<212> TYPE: DNA
<213> ORGANISM: Artificial Sequence
<220> FEATURE:
<223> OTHER INFORMATION: pKL4 plasmid coding sequence

<400> SEQUENCE: 6

```
atgcatcacc atcaccatca cgatgtgaag ctggtggaat ctggaggagg cttagtgcag         60
cctggagggt ccctgaaact ctcctgtgca acctctggat tcactttcag tgactattac        120
atgtattggg ttcgccagac tccagagaag aggctggagt gggtcgcata cattagtaat        180
gatgatagtt ccgccgctta ttcagacact gtaaagggcc ggttcaccat ctccagagac        240
aatgccaaga acaccctcta cctgcaaatg agccgtctga gtctgagga cacagccata        300 tattcctgtg caagaggact ggcctgggga gcctggtttg cttactgggg ccaagggact       360
```

| | |
|---|---|
| ctggtcactg tctctgcagc caaaacgaca cccccatctg tctatccact ggcccctgga | 420 |
| tctgctgccc aaactaactc catggtgacc ctgggatgcc tggtcaaggg ctatttccct | 480 |
| gagccagtga cagtgacctg gaactctgga tccctgtcca gcggtgtgca cccttccca | 540 |
| gctgtcctgc agtctgacct ctacactctg agcagctcag tgactgtccc ctccagcacc | 600 |
| tggcccagcg agaccgtcac ctgcaacgtt gcccacccgg ccagcagcac caaggtggac | 660 |
| aagaaaattg tgcccaggga ttgtggtgct aagccttgca tagctacaca gcttccggt | 720 |
| ggtggcggat ctggaggtgg cggaagcgga ggtcccgagg tgacaggggg aatggcaagc | 780 |
| aagtgggatc agaagggtat ggacattgcc tatgaggagg cggccttagg ttacaaagag | 840 |
| ggtggtgttc ctattggcgg atgtcttatc aataacaaag acggaagtgt tctcggtcgt | 900 |
| ggtcacaaca tgagatttca aaagggatcc gccacactac atggtgagat ctccactttg | 960 |
| gaaaactgtg ggagattaga gggcaaagtg tacaagatac cactttgta tacgacgctg | 1020 |
| tctccatgcg acatgtgtac aggtgccatc atcatgtatg gtattccacg ctgtgttgtc | 1080 |
| ggtgagaacg ttaatttcaa agtaagggc gagaaatatt tacaaactag aggtcacgag | 1140 |
| gttgttgttg ttgacgatga gaggtgtaaa aagatcatga acaatttat cgatgaaaga | 1200 |
| cctcaggatt ggtttgaaga tattggtgag tag | 1233 |

<210> SEQ ID NO 7
<211> LENGTH: 4871
<212> TYPE: DNA
<213> ORGANISM: Artificial Sequence
<220> FEATURE:
<223> OTHER INFORMATION: pMC74 plasmid full sequence

<400> SEQUENCE: 7

| | |
|---|---|
| taatacgact cactataggg agaccacaac ggtttccctc tagaaataat tttgtttaac | 60 |
| tttaagaagg agatatacat atggatgtga agctggtgga atctggagga ggcttagtgc | 120 |
| agcctggagg gtccctgaaa ctcctcctgtg caacctctgg attcactttc agtgactatt | 180 |
| acatgtattg ggttcgccag actccagaga gaggctggga gtgggtcgca tacattagta | 240 |
| atgatgatag ttccgccgct tattcagaca ctgtaaaggg ccggttcacc atctccagag | 300 |
| acaatgccag gaacaccctc tacctgcaaa tgagccgtct gaagtctgag gacacagcca | 360 |
| tatattcctg tgcaagagga ctggcctggg gagcctggtt tgcttactgg ggccaaggga | 420 |
| ctctggtcac tgtctctgca gccaaaacga caccccatc tgtctatcca ctggcccctg | 480 |
| gatctgctgc ccaaactaac tccatggtga ccctgggatg cctggtcaag ggctatttcc | 540 |
| ctgagccagt gacagtgacc tggaactctg gatccctgtc cagcggtgtg cacaccttcc | 600 |
| cagctgtcct gcagtctgac ctctacactc tgagcagctc agtgactgtc ccctccagca | 660 |
| cctggcccag cgagaccgtc acctgcaacg ttgcccaccc ggccagcagc accaaggtgg | 720 |
| acaagaaaat tgtgcccagg gattgtggta gtaagcctag cataagtaca aaagcttccg | 780 |
| gaggtcccga gggcggcagc ctggccgcgc tgaccgcgca ccaggcttgc acctgccgc | 840 |
| tggagacttt cacccgtcat cgccagccgc gcggctggga caactggag cagtgcggct | 900 |
| atccggtgca gcggctggtc gccctctacc tggcggcgcg gctgtcgtgg aaccaggtcg | 960 |
| accaggtgat ccgcaacgcc ctggccagcc cggcagcgg cggcgacctg gcgaagcga | 1020 |
| tccgcgagca gccggagcag gcccgtctgg ccctgaccct ggccgccgcc gagagcgagc | 1080 |
| gcttcgtccg gcagggcacc ggcaacgacg aggccggcgc ggccaacggc ccggcggaca | 1140 |

```
gcggcgacgc cctgctggag cgcaactatc ccactggcgc ggagttcctc ggcgacggcg    1200
gcgacgtcag cttcagcacc cgcggcacgc agaactggac ggtggagcgg ctgctccagg    1260
cgcaccgcca actggaggag cgcggctatg tgttcgtcgg ctaccacggc accttcctcg    1320
aagcggcgca aagcatcgtc ttcggcgggg tgcgcgcgcg cagccaggac ctcgacgcga    1380
tctggcgcgg tttctatatc gccggcgatc cggcgctggc ctacggctac gcccaggacc    1440
aggaacccga cgcacgcggc cggatccgca acggtgccct gctgcgggtc tatgtgccgc    1500
gctcgagcct gccgggcttc taccgcacca gcctgaccct ggccgcgccg gaggcggcgg    1560
gcgaggtcga acggctgatc ggccatccgc tgccgctgcg cctggacgcc atcaccggcc    1620
ccgaggagga aggcgggcgc ctggagacca ttctcggctg gccgctggcc gagcgcaccg    1680
tggtgattcc ctcggcgatc cccaccgacc cgcgcaacgt cggcggcgac ctcgacccgt    1740
ccagcatccc cgacaaggaa caggcgatca gcgccctgcc ggactacgcc agccagcccg    1800
gcaaaccgcc gcgcgaggac ctgaagtaac tgccgcgacc ggccggctcc cttcgcagga    1860
gccggccttc tcggggcctg gccatacatc aggttttcct gatgccagcc caatcgaata    1920
tgaattcggc tgctaacaaa gcccgaaagg aagctgagtt ggctgctgcc accgctgagc    1980
aataactagc ataaccccct gggcctctaa acgggtcttg aggggttttt tgctgaaagg    2040
aggaactata tccggatcgg agatcaattc tggcgtaata gcgaagaggc ccgcaccgat    2100
cgcccttccc aacagttgcg tagcctgaat ggcgaatggg acgcgccctg tagcggcgca    2160
ttaagcgcgg cgggtgtggt ggttacgcgc agcgtgaccg ctacacttgc cagcgcccta    2220
gcgcccgctc ctttcgcttt cttcccttcc tttctcgcca cgttcgccgg ctttccccgt    2280
caagctctaa atcgggggct ccctttaggg ttccgattta gtgctttacg gcacctcgac    2340
cccaaaaaac ttgattaggg tgatggttca cgtagtgggc catcgccctg atagacggtt    2400
tttcgccctt tgacgttgga gtccacgttc tttaatagtg gactcttgtt ccaaactgga    2460
acaacactca accctatctc ggtctattct tttgatttat aagggatttt gccgatttcg    2520
gcctattggt taaaaaatga gctgatttaa caaaaattta acgcgaattt taacaaaata    2580
ttaacgttta caatttcagg tggcactttt cggggaaatg tgcgcggaac ccctatttgt    2640
ttatttttct aaatacattc aaatatgtat ccgctcatga caataaccct gataaatg     2700 cttcaataat attgaaaaag gaagagtatg agtattcaac atttccgtgt cgcccttatt    2760 ccctttttg cggcattttg ccttcctgtt tttgctcacc cagaaacgct ggtgaaagta    2820
aaagatgctg aagatcagtt gggtgcacga gtgggttaca tcgaactgga tctcaacagc    2880
ggtaagatcc ttgagagttt tcgccccgaa gaacgttttc caatgatgag cacttttaaa    2940
gttctgctat gtggcgcggt attatcccgt attgacgccg ggcaagagca actcggtcgc    3000
cgcatacact attctcagaa tgacttggtt gagtactcac cagtcacaga aaagcatctt    3060
acggatggca tgacagtaag agaattatgc agtgctgcca taagcatgag tgataacact    3120
gcggccaact tacttctgac aacgatcgga ggaccgaagg agctaaccgc ttttttcac    3180 aacatggggg atcatgtaac tcgccttgat cgttgggaac cggagctgaa tgaagccata    3240
ccaaacgacg agcgtgacac cacgatgcct gtagcaatgg caacaacgtt gcgcaaacta    3300
ttaactggcg aactacttac tctagcttcc cggcaacaat taatagactg gatgaggcg    3360 gataaagttg caggaccact tctgcgctcg gcccttccgg ctggctggtt tattgctgat    3420
aaatctggag ccggtgagcg tgggtctcgc ggtatcattg cagcactggg gccagatggt    3480
aagccctccc gtatcgtagt tatctacacg acgggcagtc aggcaactat ggatgaacga    3540
```

```
aatagacaga tcgctgagat aggtgcctca ctgattaagc attggtaact gtcagaccaa    3600
gtttactcat atatacttta gattgattta aacttcatt tttaatttaa aaggatctag     3660
gtgaagatcc ttttttgataa tctcatgacc aaaatcccctt aacgtgagtt tcgttccac   3720 tgagcgtcag accccgtaga aaagatcaaa ggatcttctt gagatccttt ttttctgcgc    3780
gtaatctgct gcttgcaaac aaaaaaacca ccgctaccag cggtggtttg tttgccggat    3840
caagagctac caactctttt tccgaaggta actggcttca gcagagcgca gataccaaat    3900
actgtccttc tagtgtagcc gtagttaggc caccacttca agaactctgt agcaccgcct    3960
acatacctcg ctctgctaat cctgttacca gtggctgctg ccagtggcga taagtcgtgt    4020
cttaccgggt tggactcaag acgatagtta ccggataagg cgcagcggtc gggctgaacg    4080
gggggttcgt gcacacagcc cagcttggag cgaacgacct acaccgaact gagatacccta   4140 cagcgtgagc attgagaaag cgccacgctt cccgaaggga gaaaggcgga caggtatccg    4200
gtaagcggca gggtcggaac aggagagcgc acgagggagc ttccagggg gaacgcctgg     4260 tatctttata gtcctgtcgg gtttcgccac ctctgacttg agcgtcgatt tttgtgatgc    4320
tcgtcagggg ggccgagcct atggaaaaac gccagcaacg cggccttttt acggttcctg    4380
gccttttgct ggccttttgc tcacatgttc tttcctgcgt tatcccctga ttctgtggat    4440
aaccgtatta ccgcctttga gtgagctgat accgctcgcc gcagccgaac gaccgagcgc    4500
agcgagtcag tgagcgagga agcggaagag cgcctgatgc ggtattttct ccttacgcat    4560
ctgtgcggta tttcacaccg catatatggt gcactctcag tacaatctgc tctgatgccg    4620
catagttaag ccagtataca ctccgctatc gctacgtgac tgcaaggaga tggcgcccaa    4680 cagtccccccg gccacggggc ctgccaccat acccacgccg aaacaagcgc tcatgagccc    4740
gaagtggcga gcccgatctt ccccatcggt gatgtcggcg atataggcgc cagcaaccgc    4800
acctgtggcg ccggtgatgc cggccacgat gcgtccggcg tagaggatct tgagatctcg    4860
atccgcgaaa t                                                         4871
```

<210> SEQ ID NO 8
<211> LENGTH: 4886
<212> TYPE: DNA
<213> ORGANISM: Artificial Sequence
<220> FEATURE:
<223> OTHER INFORMATION: pMH21 plasmid full sequence

<400> SEQUENCE: 8

```
taatacgact cactataggg agaccacaac ggtttccctc tagaaataat tttgtttaac      60
tttaagaagg agatatacat atggaggtga agctggtgga atctggagga ggcttagtgc     120
agcctggagg gtccctgaaa ctctcctgtg caacctctgg attcactttc agtgactatt     180
acatgtattg ggttcgccag actccagaga gaggctgga gtgggtcgca tacattagta     240
atgatgatag ttccgccgct tattcagaca ctgtaaaggg ccggttcacc atctccagag    300
acaatgccag gaacaccctc tacctgcaaa tgagccgtct gaagtctgag gacacagcca    360
tatattcctg tgcaagagga ctggcctggg gagcctggtt tgcttactgg ggccaaggga    420
ctctggtcac tgtctctgca gccaaaacga caccccccatc tgtctatcca ctggcccctg    480
gatctgctgc ccaaactaac tccatggtga ccctgggatg cctggtcaag ggctatttcc    540
ctgagccagt gacagtgacc tggaactctg atccctgtc cagcggtgtg cacaccttcc    600
cagctgtcct gcagtctgac ctctacactc tgagcagctc agtgactgtc ccctccagca    660
```

-continued

```
cctggcccag cgagaccgtc acctgcaacg ttgcccaccc ggccagcagc accaaggtgg      720
acaagaaaat tgtgcccagg gattgtggta gtaagccttg cataagtaca aaagcttctg      780
gtggtggcgg atctggaggt cccgagggcg cagcctggc cgcgctgacc gcgcaccagg       840
cttgccacct gccgctggag actttcaccc gtcatcgcca gccgcgcggc tgggaacaac      900
tggagcagtg cggctatccg gtgcagcggc tggtcgccct ctacctggcg gcgcggctgt      960
cgtggaacca ggtcgaccag gtgatccgca acgccctggc cagccccggc agcggcggcg     1020
acctgggcga agcgatccgc gagcagccgg agcaggcccg tctggccctg accctggccg     1080
ccgccgagag cgagcgcttc gtccggcagg gcaccggcaa cgacgaggcc ggcgcggcca     1140
acggcccggc ggacagcggc gacgccctgc tggagcgcaa ctatcccact ggcgcggagt     1200
tcctcggcga cggcggcgac gtcagcttca gcacccgcgg cacgcagaac tggacggtgg     1260
agcggctgct ccaggcgcac cgccaactgg aggagcgcgg ctatgtgttc gtcggctacc     1320
acggcacctt cctcgaagcg gcgcaaagca tcgtcttcgg cggggtgcgc gcgcgcagcc     1380
aggacctcga cgcgatctgg cgcggtttct atatcgccgg cgatccggcg ctggcctacg     1440
gctacgccca ggaccaggaa cccgacgcac gcggccggat ccgcaacggt gccctgctgc     1500
gggtctatgt gccgcgctcg agcctgccgg gcttctaccg caccagcctg accctggccg     1560
cgccggaggc ggcgggcgag gtcgaacggc tgatcggcca tccgctgccg ctgcgcctgg     1620
acgccatcac cggccccgag gaggaaggcg ggcgcctgga gaccattctc ggctggccgc     1680
tggccgagcg caccgtggtg attccctcgg cgatccccac cgaccgcgc aacgtcggcg      1740
gcgacctcga cccgtccagc atccccgaca aggaacaggc gatcagcgcc ctgccggact     1800
acgcagccaa gcccggcaaa ccgcgcgcg aggacctgaa gtaactgccg cgaccggccg      1860
gctcccttcg caggagccgg ccttctcggg gcctggccat acatcaggtt ttcctgatgc     1920
cagcccaatc gaatatgaat tcggctgcta acaaagcccg aaaggaagct gagttggctg     1980
ctgccaccgc tgagcaataa ctagcataac cccttgggcc tctaaacggg tcttgagggg     2040
tttttttgctg aaaggaggaa ctatatccgg atcggagatc aattctggcg taatagcgaa     2100
gaggcccgca ccgatcgccc ttcccaacag ttgcgtagcc tgaatggcga atgggacgcg     2160
ccctgtagcg gcgcattaag cgcggcgggt gtggtggtta cgcgcagcgt gaccgctaca     2220
cttgccagcg ccctagcgcc cgctccttc gctttcttcc cttcctttct cgccacgttc       2280
gccggctttc cccgtcaagc tctaaatcgg gggctccctt tagggttccg atttagtgct     2340
ttacggcacc tcgaccccaa aaaacttgat tagggtgatg gttcacgtag tgggccatcg     2400
ccctgataga cggttttttcg ccctttgacg ttggagtcca cgttctttaa tagtggactc     2460
ttgttccaaa ctggaacaac actcaaccct atctcggtct attctttga tttataaggg       2520
attttgccga tttcggccta ttggttaaaa aatgagctga tttaacaaaa atttaacgcg     2580
aattttaaca aaatattaac gtttacaatt tcaggtggca cttttcgggg aaatgtgcgc     2640
ggaaccccta tttgtttatt tttctaaata cattcaaata tgtatccgct catgagacaa     2700
taaccctgat aaatgcttca ataatattga aaaaggaaga gtatgagtat tcaacatttc     2760
cgtgtcgccc ttattccctt ttttgcggca ttttgccttc ctgttttttgc tcacccagaa     2820
acgctggtga aagtaaaaga tgctgaagat cagttgggtg cacgagtggg ttacatcgaa     2880
ctggatctca acagcggtaa gatccttgag agttttcgcc ccgaagaacg ttttccaatg     2940
atgagcactt ttaaagttct gctatgtggc gcggtattat cccgtattga cgccgggcaa     3000
gagcaactcg gtcgccgcat acactattct cagaatgact tggttgagta ctcaccagtc     3060
```

| | |
|---|---|
| acagaaaagc atcttacgga tggcatgaca gtaagagaat tatgcagtgc tgccataagc | 3120 |
| atgagtgata acactgcggc caacttactt ctgacaacga tcggaggacc gaaggagcta | 3180 |
| accgcttttt ttcacaacat gggggatcat gtaactcgcc ttgatcgttg ggaaccggag | 3240 |
| ctgaatgaag ccataccaaa cgacgagcgt gacaccacga tgcctgtagc aatggcaaca | 3300 |
| acgttgcgca aactattaac tggcgaacta cttactctag cttcccggca acaattaata | 3360 |
| gactggatgg aggcggataa agttgcagga ccacttctgc gctcggccct tccggctggc | 3420 |
| tggtttattg ctgataaatc tggagccggt gagcgtgggt ctcgcggtat cattgcagca | 3480 |
| ctggggccag atggtaagcc ctcccgtatc gtagttatct acacgacggg cagtcaggca | 3540 |
| actatgatg aacgaaatag acagatcgct gagataggtg cctcactgat taagcattgg | 3600 |
| taactgtcag accaagttta ctcatatata ctttagattg atttaaaact tcatttttaa | 3660 |
| tttaaaagga tctaggtgaa gatcctttt gataatctca tgaccaaaat cccttaacgt | 3720 |
| gagttttcgt tccactgagc gtcagacccc gtagaaaaga tcaaaggatc ttcttgagat | 3780 |
| cctttttttc tgcgcgtaat ctgctgcttg caaacaaaaa aaccaccgct accagcggtg | 3840 |
| gtttgtttgc cggatcaaga gctaccaact cttttttccga aggtaactgg cttcagcaga | 3900 |
| gcgcagatac caaatactgt ccttctagtg tagccgtagt taggccacca cttcaagaac | 3960 |
| tctgtagcac cgcctacata cctcgctctg ctaatcctgt taccagtggc tgctgccagt | 4020 |
| ggcgataagt cgtgtcttac cgggttggac tcaagacgat agttaccgga taaggcgcag | 4080 |
| cggtcgggct gaacggggg ttcgtgcaca cagcccagct tggagcgaac gacctacacc | 4140 |
| gaactgagat acctacagcg tgagcattga gaaagcgcca cgcttcccga agggagaaag | 4200 |
| gcggacaggt atccggtaag cggcagggtc ggaacaggag agcgcacgag ggagcttcca | 4260 |
| gggggaacg cctggtatct ttatagtcct gtcgggtttc gccacctctg acttgagcgt | 4320 |
| cgatttttgt gatgctcgtc aggggggcg agcctatgga aaaacgccag caacgcggcc | 4380 |
| tttttacggt tcctggcctt tgctggcct tttgctcaca tgttctttcc tgcgttatcc | 4440 |
| cctgattctg tggataaccg tattaccgcc tttgagtgag ctgataccgc tcgccgcagc | 4500 |
| cgaacgaccg agcgcagcga gtcagtgagc gaggaagcgg aagagcgcct gatgcggtat | 4560 |
| tttctcctta cgcatctgtg cggtatttca caccgcatat atggtgcact ctcagtacaa | 4620 |
| tctgctctga tgccgcatag ttaagccagt atacactccg ctatcgctac gtgactgcaa | 4680 |
| ggagatggcg cccaacagtc ccccggccac ggggcctgcc accataccca cgccgaaaca | 4740 |
| agcgctcatg agcccgaagt ggcgagcccg atcttcccca tcggtgatgt cggcgatata | 4800 |
| ggcgccagca accgcacctg tggcgccggt gatgccggcc acgatgcgtc cggcgtagag | 4860 |
| gatcttgaga tctcgatccg cgaaat | 4886 |

<210> SEQ ID NO 9
<211> LENGTH: 4871
<212> TYPE: DNA
<213> ORGANISM: Artificial Sequence
<220> FEATURE:
<223> OTHER INFORMATION: pCE2 plasmid full sequence

<400> SEQUENCE: 9

| | |
|---|---|
| taatacgact cactataggg agaccacaac ggtttccctc tagaaataat tttgtttaac | 60 |
| tttaagaagg agatatacat atggatgtga agctggtgga atctggagga ggcttagtgc | 120 |
| agcctggagg gtccctgaaa ctctcctgtg caacctctgg attcactttc agtgactatt | 180 |

```
acatgtattg ggttcgccag actccagaga agaggctgga gtgggtcgca tacattagta      240
atgatgatag ttccgccgct tattcagaca ctgtaaaggg ccggttcacc atctccagag      300
acaatgccag gaacaccctc tacctgcaaa tgagccgtct gaagtctgag gacacagcca      360
tatattcctg tgcaagagga ctggcctggg gagcctggtt tgcttactgg ggccaaggga      420
ctctggtcac tgtctctgca gccaaaacga caccccatc tgtctatcca ctggcccctg       480
gatctgctgc ccaaactaac tccatggtga ccctgggatg cctggtcaag ggctatttcc      540
ctgagccagt gacagtgacc tggaactctg gatccctgtc cagcggtgtg cacaccttcc      600
cagctgtcct gcagtctgac ctctacactc tgagcagctc agtgactgtc ccctccagca      660
cctggcccag cgagaccgtc acctgcaacg ttgcccaccc ggccagcagc accaaggtgg      720
acaagaaaat tgtgcccagg gattgtggta gtaagccttg cataagtaca aaagcttccg      780
gaggtcccga gggcggcagc ctggccgcgc tgaccgcgca ccaggcttgc acctgccgc       840 tggagacttt cacccgtcat cgccagccgc gcggctggga acaactggag cagtgcggct      900
atccggtgca gcggctggtc gccctctacc tggcggcgcg gctgtcgtgg aaccaggtcg      960
accaggtgat ccgcaacgcc ctggccagcc cggcagcgg cggcgacctg ggcgaagcga      1020
tccgcgagca gccggagcag gcccgtctgg ccctgaccct ggccgccgcc gagagcgagc     1080
gcttcgtccg gcagggcacc ggcaacgacg aggccggcgc ggccaacggc ccggcggaca     1140
gcggcgacgc cctgctggag cgcaactatc ccactggcgc ggagttcctc ggcgacggcg     1200
gcgacgtcag cttcagcacc cgcggcacgc agaactggac ggtggagcgg ctgctccagg     1260
cgcaccgcca actggaggag cgcggctatg tgttcgtcgg ctaccacggc accttcctcg     1320
aagcggcgca aagcatcgtc ttcggcgggg tgcgcgcgcg cagccaggac ctcgacgcga     1380
tctggcgcgg tttctatatc gccggcgatc cggcgctggc ctacggctac gcccaggacc     1440
aggaacccga cgcacgcggc cggatccgca acggtgccct gctgcgggtc tatgtgccgc     1500
gctcgagcct gccgggcttc taccgcacca gcctgaccct ggccgcgccg gaggcggcgg     1560
gcgaggtcga acggctgatc ggccatccgc tgccgctgcg cctggacgcc atcaccggcc     1620
ccgaggagga aggcgggcgc ctggagacca ttctcggctg gccgctggcc gagcgcaccg     1680
tggtgattcc ctcggcgatc cccaccgacc cgcgcaacgt cggcggcgac ctcgacccgt     1740
ccagcatccc cgacaaggaa caggcgatca gcgccctgcc ggactacgcc agccagcccg     1800
gcaaaccgcc gcgcgaggac ctgaagtaac tgccgcgacc ggccggctcc cttcgcagga     1860
gccggccttc tcggggcctg gccatacatc aggtttttcct gatgccagcc caatcgaata     1920
tgaattcggc tgctaacaaa gcccgaaagg aagctgagtt ggctgctgcc accgctgagc     1980
aataactagc ataaccccctt gggcctctaa acgggtcttg aggggttttt tgctgaaagg     2040
aggaactata tccggatcgg agatcaattc tggcgtaata gcgaagaggc ccgcaccgat     2100
cgcccttccc aacagttgcg tagcctgaat ggcgaatggg acgcgccctg tagcggcgca     2160
ttaagcgcgg cgggtgtggt ggttacgcgc agcgtgaccg ctacacttgc cagcgcccta     2220
gcgcccgctc ctttcgcttt cttcccttcc tttctcgcca cgttcgccgg ctttccccgt     2280
caagctctaa atcggggggct cccctttaggg ttccgattta gtgctttacg gcacctcgac     2340
cccaaaaaac ttgattaggg tgatggttca cgtagtgggc catcgccctg atagacggtt     2400
tttcgccctt tgacgttgga gtccacgttc tttaatagtg gactcttgtt ccaaactgga     2460
acaacactca accctatctc ggtctattct tttgatttat aagggatttt gccgatttcg     2520
gcctattggt taaaaaatga gctgatttaa caaaaattta cgcgaatttt taacaaaata     2580
```

```
ttaacgttta caatttcagg tggcactttt cggggaaatg tgcgcggaac ccctatttgt    2640
ttatttttct aaatacattc aaatatgtat ccgctcatga gacaataacc ctgataaatg    2700
cttcaataat attgaaaaag gaagagtatg agtattcaac atttccgtgt cgcccttatt    2760 ccctttttg cggcattttg ccttcctgtt tttgctcacc cagaaacgct ggtgaaagta    2820
aaagatgctg aagatcagtt gggtgcacga gtgggttaca tcgaactgga tctcaacagc    2880
ggtaagatcc ttgagagttt tcgccccgaa gaacgttttc caatgatgag cacttttaaa    2940
gttctgctat gtggcgcggt attatcccgt attgacgccg ggcaagagca actcggtcgc    3000
cgcatacact attctcagaa tgacttggtt gagtactcac cagtcacaga aaagcatctt    3060
acggatggca tgacagtaag agaattatgc agtgctgcca taagcatgag tgataacact    3120
gcggccaact tacttctgac aacgatcgga ggaccgaagg agctaaccgc ttttttttcac    3180 aacatggggg atcatgtaac tcgccttgat cgttgggaac cggagctgaa tgaagccata    3240
ccaaacgacg agcgtgacac cacgatgcct gtagcaatgg caacaacgtt gcgcaaacta    3300
ttaactggcg aactacttac tctagcttcc cggcaacaat taatagactg gatggaggcg    3360
gataaagttg caggaccact tctgcgctcg gcccttccgg ctggctggtt tattgctgat    3420
aaatctggag ccggtgagcg tgggtctcgc ggtatcattg cagcactggg gccagatggt    3480
aagccctccc gtatcgtagt tatctacacg acgggcagtc aggcaactat ggatgaacga    3540
aatagacaga tcgctgagat aggtgcctca ctgattaagc attggtaact gtcagaccaa    3600
gtttactcat atatacttta gattgattta aaacttcatt tttaatttaa aaggatctag    3660
gtgaagatcc tttttgataa tctcatgacc aaaatccctt aacgtgagtt ttcgttccac    3720
tgagcgtcag accccgtaga aaagatcaaa ggatcttctt gagatccttt ttttctgcgc    3780
gtaatctgct gcttgcaaac aaaaaaacca ccgctaccag cggtggtttg tttgccggat    3840
caagagctac caactctttt tccgaaggta actggcttca gcagagcgca gataccaaat    3900
actgtccttc tagtgtagcc gtagttaggc caccacttca agaactctgt agcaccgcct    3960
acatacctcg ctctgctaat cctgttacca gtggctgctg ccagtggcga taagtcgtgt    4020
cttaccgggt tggactcaag acgatagtta ccggataagg cgcagcggtc gggctgaacg    4080
gggggttcgt gcacacagcc cagcttggag cgaacgacct acaccgaact gagatacccta    4140 cagcgtgagc attgagaaag cgccacgctt cccgaaggga gaaaggcgga caggtatccg    4200
gtaagcggca gggtcggaac aggagagcgc acgagggagc ttccaggggg gaacgcctgg    4260
tatctttata gtcctgtcgg gtttcgccac ctctgacttg agcgtcgatt tttgtgatgc    4320
tcgtcagggg ggcgagcct atggaaaaac gccagcaacg cggccttttt acggttcctg    4380
gccttttgct ggccttttgc tcacatgttc tttcctgcgt tatcccctga ttctgtggat    4440
aaccgtatta ccgcctttga gtgagctgat accgctcgcc gcagccgaac gaccgagcgc    4500
agcgagtcag tgagcgagga agcggaagag cgcctgatgc ggtattttct ccttacgcat    4560
ctgtgcggta tttcacaccg catatatggt gcactctcag tacaatctgc tctgatgccg    4620
catagttaag ccagtataca ctccgctatc gctacgtgac tgcaaggaga tggcgcccaa    4680
cagtcccccg gccacggggc ctgccaccat acccacgccg aaacaagcgc tcatgagccc    4740
gaagtggcga gcccgatctt ccccatcggt gatgtcggcg atataggcgc cagcaaccgc    4800
acctgtggcg ccggtgatgc cggccacgat gcgtccggcg tagaggatct tgagatctcg    4860
atccgcgaaa t                                                          4871
```

<210> SEQ ID NO 10
<211> LENGTH: 3703
<212> TYPE: DNA
<213> ORGANISM: Artificial Sequence
<220> FEATURE:
<223> OTHER INFORMATION: pMC75 plasmid full sequence

<400> SEQUENCE: 10

| | | | | | | |
|---|---|---|---|---|---|---|
| taatacgact | cactataggg | agaccacaac | ggtttccctc | tagaaataat | tttgtttaac | 60 |
| tttaagaagg | agatatacat | atggatgtgc | tgatgaccca | gtctccattg | agtttacctg | 120 |
| tcagtcttgg | agatcaagcc | tccatctctt | gcagatctag | tcagatcatt | gtacatagta | 180 |
| atggaaacac | ctatttagaa | tggtacctgc | agaaaccagg | ccagtctcca | aagctcctga | 240 |
| tctacaaagt | ttccaaccga | ttttctgggg | tcccagacag | gttcagtggc | agtggatcag | 300 |
| ggacagattt | cacactcaag | atcagcagag | tggaggctga | ggatctggga | gtttattact | 360 |
| gctttcaagg | ttcacatgtt | ccattcacgt | tcggctcggg | gacaaagttg | gaaataaaac | 420 |
| gggctgatgc | tgcaccaact | gtatccatct | tcccaccatc | cagtgagcag | ttaacatctg | 480 |
| gaggtgcctc | agtcgtgtgc | ttcttgaaca | acttctaccc | caaagacatc | aatgtcaagt | 540 |
| ggaagattga | tggcagtgaa | cgacaaaatg | gcgtcctgaa | cagttggact | gatcaggaca | 600 |
| gcaaagacag | cacctacagc | atgagcagca | ccctcacgtt | gaccaaggac | gagtatgaac | 660 |
| gacataacag | ctatacctgt | gaggccactc | acaagacatc | aacttcaccc | attgtcaaga | 720 |
| gcttcaacag | gaatgagtgt | ggtaaagctt | aatgaattcg | ctgctaaca | aagcccgaaa | 780 |
| ggaagctgag | ttggctgctg | ccaccgctga | gcaataacta | gcataacccc | ttgggcctct | 840 |
| aaacgggtct | tgaggggttt | tttgctgaaa | ggaggaacta | tatccggatc | ggagatcaat | 900 |
| tctggcgtaa | tagcgaagag | gcccgcaccg | atcgcccttc | ccaacagttg | cgtagcctga | 960 |
| atggcgaatg | ggacgcgccc | tgtagcggcg | cattaagcgc | ggcgggtgtg | gtggttacgc | 1020 |
| gcagcgtgac | cgctacactt | gccagcgccc | tagcgcccgc | tcctttcgct | ttcttccctt | 1080 |
| cctttctcgc | cacgttcgcc | ggctttcccc | gtcaagctct | aaatcggggg | ctccctttag | 1140 |
| ggttccgatt | tagtgcttta | cggcacctcg | accccaaaaa | acttgattag | ggtgatggtt | 1200 |
| cacgtagtgg | gccatcgccc | tgatagacgg | ttttcgccc | tttgacgttg | gagtccacgt | 1260 |
| tctttaatag | tggactcttg | ttccaaactg | gaacaacact | caaccctatc | tcggtctatt | 1320 |
| cttttgattt | ataagggatt | ttgccgattt | cggcctattg | gttaaaaaat | gagctgattt | 1380 |
| aacaaaaatt | taacgcgaat | tttaacaaaa | tattaacgtt | tacaatttca | ggtggcactt | 1440 |
| ttcggggaaa | tgtgcgcgga | accctatttt | gtttattttt | ctaaatacat | tcaaatatgt | 1500 |
| atccgctcat | gagacaataa | ccctgataaa | tgcttcaata | atattgaaaa | aggaagagta | 1560 |
| tgagtattca | acatttccgt | gtcgccctta | ttccctttt | tgcggcattt | tgccttcctg | 1620 |
| tttttgctca | cccagaaacg | ctggtgaaag | taaaagatgc | tgaagatcag | ttgggtgcac | 1680 |
| gagtgggtta | catcgaactg | gatctcaaca | gcggtaagat | ccttgagagt | tttcgccccg | 1740 |
| aagaacgttt | tccaatgatg | agcactttta | aagttctgct | atgtggcgcg | gtattatccc | 1800 |
| gtattgacgc | cgggcaagag | caactcggtc | gccgcataca | ctattctcag | aatgacttgg | 1860 |
| ttgagtactc | accagtcaca | gaaaagcatc | ttacggatgg | catgacagta | agagaattat | 1920 |
| gcagtgctgc | cataagcatg | agtgataaca | ctgcggccaa | cttacttctg | acaacgatcg | 1980 |
| gaggaccgaa | ggagctaacc | gcttttttc | acaacatggg | ggatcatgta | actcgccttg | 2040 |
| atcgttggga | accggagctg | aatgaagcca | taccaaacga | cgagcgtgac | accacgatgc | 2100 |

```
ctgtagcaat ggcaacaacg ttgcgcaaac tattaactgg cgaactactt actctagctt   2160
cccggcaaca attaatagac tggatggagg cggataaagt tgcaggacca cttctgcgct   2220
cggcccttcc ggctggctgg tttattgctg ataaatctgg agccggtgag cgtgggtctc   2280
gcggtatcat tgcagcactg gggccagatg gtaagccctc ccgtatcgta gttatctaca   2340
cgacgggcag tcaggcaact atggatgaac gaaatagaca gatcgctgag ataggtgcct   2400
cactgattaa gcattggtaa ctgtcagacc aagtttactc atatatactt tagattgatt   2460
taaaacttca tttttaattt aaaaggatct aggtgaagat cctttttgat aatctcatga   2520
ccaaaatccc ttaacgtgag ttttcgttcc actgagcgtc agaccccgta gaaaagatca   2580
aaggatcttc ttgagatcct ttttttctgc gcgtaatctg ctgcttgcaa acaaaaaaac   2640
caccgctacc agcggtggtt tgtttgccgg atcaagagct accaactctt tttccgaagg   2700
taactggctt cagcagagcg cagataccaa atactgtcct tctagtgtag ccgtagttag   2760
gccaccactt caagaactct gtagcaccgc ctacatacct cgctctgcta atcctgttac   2820
cagtggctgc tgccagtggc gataagtcgt gtcttaccgg gttggactca agacgatagt   2880
taccggataa ggcgcagcgg tcgggctgaa cggggggttc gtgcacacag cccagcttgg   2940
agcgaacgac ctacaccgaa ctgagatacc tacagcgtga gcattgagaa agcgccacgc   3000
ttcccgaagg gagaaaggcg gacaggtatc cggtaagcgg cagggtcgga acaggagagc   3060
gcacgaggga gcttccaggg gggaacgcct ggtatcttta tagtcctgtc gggtttcgcc   3120
acctctgact tgagcgtcga tttttgtgat gctcgtcagg gggccgagc ctatggaaaa   3180 acgccagcaa cgcggccttt ttacggttcc tggccttttg ctggccttt gctcacatgt   3240 tctttcctgc gttatcccct gattctgtgg ataaccgtat taccgccttt gagtgagctg   3300
ataccgctcg ccgcagccga acgaccgagc gcagcgagtc agtgagcgag gaagcggaag   3360
agcgcctgat gcggtatttt ctccttacgc atctgtgcgg tatttcacac cgcatatatg   3420
gtgcactctc agtacaatct gctctgatgc cgcatagtta agccagtata cactccgcta   3480
tcgctacgtg actgcaagga gatggcgccc aacagtcccc cggccacggg gcctgccacc   3540
atacccacgc cgaaacaagc gctcatgagc ccgaagtggc gagcccgatc ttccccatcg   3600
gtgatgtcgg cgatataggc gccagcaacc gcacctgtgg cgccggtgat gccggccacg   3660
atgcgtccgg cgtagaggat cttgagatct cgatccgcga aat                     3703

<210> SEQ ID NO 11
<211> LENGTH: 5576
<212> TYPE: DNA
<213> ORGANISM: Artificial Sequence
<220> FEATURE:
<223> OTHER INFORMATION: pLSC52 plasmid full sequence

<400> SEQUENCE: 11
taatacgact cactataggg agaccacaac ggtttccctc tagaaataat tttgtttaac     60
tttaagaagg agatatacat atggatgtga agctggtgga atctggagga ggcttagtgc    120
agcctggagg gtccctgaaa ctctcctgtg caacctctgg attcactttc agtgactatt    180
acatgtattg ggttcgccag actccagaga gaggctggag gtgggtcgca tacattagta    240
atgatgatag ttccgccgct tattcagaca ctgtaaaggg ccggttcacc atctccagag    300
acaatgccag gaacaccctc tacctgcaaa tgagccgtct gaagtctgag gacacagcca    360
tatattcctg tgcaagagga ctggcctggg gagcctggtt tgcttactgg ggccaaggga    420
```

```
ctctggtcac tgtctctgca gccaaaacga caccccatc tgtctatcca ctggcccctg      480
gatctgctgc ccaaactaac tccatggtga ccctgggatg cctggtcaag ggctatttcc      540
ctgagccagt gacagtgacc tggaactctg gatccctgtc cagcggtgtg cacaccttcc      600
cagctgtcct gcagtctgac ctctacactc tgagcagctc agtgactgtc ccctccagca      660
cctggcccag cgagaccgtc acctgcaacg ttgcccaccc ggccagcagc accaaggtgg      720
acaagaaaat tgtgcccagg gattgtggtg agcccaaatc ttgtgacaaa actcacacat      780
gcccaccgtg cccagcacct gaactcctgg ggggaccgtc agtcttcctc ttccccccaa      840
aacccaagga caccctcatg atctcccgga cccctgaggt cacatgcgtg gtggtggacg      900
tgagccacga agaccctgag gtcaagttca actggtacgt ggacggcgtg gaggtgcata      960
atgccaagac aaagccgcgg gaggagcagt acaacagcac gtaccgtgtg gtcagcgtcc     1020
tcaccgtcct gcaccaggac tggctgaatg gcaaggagta caagtgcaag gtctccaaca     1080
aagccctccc agcccccatc gagaaaacca tctccaaagc caaagggcag ccccgagaac     1140
cacaggtgta caccctgccc ccatcccggg atgagctgac caagaaccag gtcagcctga     1200
cctgcctggt caaaggcttc tatcccagcg acatcgccgt ggagtgggag agcaatgggc     1260
agccggagaa caactacaag accacgcctc ccgtgctgga ctccgacggc tccttcttcc     1320
tctacagcaa gctcaccgtg gacaagagca ggtggcagca ggggaacgtc ttctcatgct     1380
ccgtgatgca tgaggctctg cacaaccact acacgcagaa gagcctctcc ctgtctccgg     1440
gtaaaggcgg aggcggatcc ggtggtggcg gttctaaagc ttccggaggt cccgagggcg     1500
gcagcctggc cgcgctgacc gcgcaccagg cttgccacct gccgctggag actttcaccc     1560
gtcatcgcca gccgcgcggc tgggaacaac tggagcagtg cggctatccg gtgcagcggc     1620
tggtcgccct ctacctggcg cgcgggctgt cgtggaacca ggtcgaccag gtgatccgca     1680
acgccctggc cagccccggc agcggcggcg acctgggcga agcgatccgc gagcagccgg     1740
agcaggcccg tctggccctg accctggccg ccgccgagag cgagcgcttc gtccggcagg     1800
gcaccggcaa cgacgaggcc ggcgcggcca acggcccggc ggacagcggc gacgccctgc     1860
tggagcgcaa ctatcccact ggcgcggagt tcctcggcga cggcggcgac gtcagcttca     1920
gcacccgcgg cacgcagaac tggacggtgg agcggctgct ccaggcgcac cgccaactgg     1980
aggagcgcgg ctatgtgttc gtcggctacc acggcacctt cctcgaagcg gcgcaaagca     2040
tcgtcttcgg cggggtgcgc gcgcgcagcc aggacctcga cgcgatctgg cgcggtttct     2100
atatcgccgg cgatccggcg ctggcctacg gctacgccca ggaccaggaa cccgacgcac     2160
gcggccggat ccgcaacggt gccctgctgc gggtctatgt gccgcgctcg agcctgccgg     2220
gcttctaccg caccagcctg accctggccg cgccggaggc ggcgggcgag gtcgaacggc     2280
tgatcggcca tccgctgccg ctgcgcctgg acgccatcac cggccccgag gaggaaggcg     2340
ggcgcctgga gaccattctc ggctggccgc tggccgagcg caccgtggtg attccctcgg     2400
cgatccccac cgaccccgcg aacgtcggcg gcgacctcga cccgtccagc atccccgaca     2460
aggaacaggc gatcagcgcc ctgccggact acgccagcca gccggcaaa ccgccgcgcg     2520 aggacctgaa gtaactgccg cgaccggccg gctcccttcg caggagccgg cctctcgggg     2580
gcctggccat acatcaggtt ttcctgatgc cagcccaatc gaatatgaat tcggctgcta     2640
acaaagcccg aaaggaagct gagttggctg ctgccaccgc tgagcaataa ctagcataac     2700 cccttgggc tctaaacggg tcttgagggg ttttttgctg aaaggaggaa ctatatccgg     2760
atcggagatc aattctggcg taatagcgaa gaggcccgca ccgatcgccc ttcccaacag     2820
```

```
ttgcgtagcc tgaatggcga atgggacgcg ccctgtagcg gcgcattaag cgcggcgggt    2880
gtggtggtta cgcgcagcgt gaccgctaca cttgccagcg ccctagcgcc cgctcctttc    2940
gctttcttcc cttcctttct cgccacgttc gccggctttc cccgtcaagc tctaaatcgg    3000 gggctcccctt tagggttccg atttagtgct ttacggcacc tcgaccccaa aaaacttgat   3060
tagggtgatg gttcacgtag tgggccatcg ccctgataga cggttttttcg ccctttgacg   3120 ttggagtcca cgttctttaa tagtggactc ttgttccaaa ctggaacaac actcaaccct    3180
atctcggtct attcttttga tttataaggg attttgccga tttcggccta ttggttaaaa    3240
aatgagctga tttaacaaaa atttaacgcg aattttaaca aaatattaac gtttacaatt    3300
tcaggtggca cttttcgggg aaatgtgcgc ggaacccta tttgtttatt tttctaaata     3360
cattcaaata tgtatccgct catgagacaa taaccctgat aaatgcttca ataatattga    3420
aaaaggaaga gtatgagtat tcaacatttc cgtgtcgccc ttattccctt ttttgcggca    3480
ttttgccttc ctgttttttgc tcacccagaa acgctggtga agtaaaaga tgctgaagat    3540 cagtggggtg cacgagtggg ttacatcgaa ctggatctca acagcggtaa gatccttgag    3600
agttttcgcc ccgaagaacg ttttccaatg atgagcactt ttaaagttct gctatgtggc    3660
gcggtattat cccgtattga cgccgggcaa gagcaactcg gtcgccgcat acactattct    3720
cagaatgact tggttgagta ctcaccagtc acagaaaagc atcttacgga tggcatgaca    3780
gtaagagaat tatgcagtgc tgccataagc atgagtgata acactgcggc caacttactt    3840
ctgacaacga tcggaggacc gaaggagcta accgcttttt ttcacaacat ggggdatcat    3900
gtaactcgcc ttgatcgttg ggaaccggag ctgaatgaag ccataccaaa cgacgagcgt    3960
gacaccacga tgcctgtagc aatggcaaca acgttgcgca aactattaac tggcgaacta    4020
cttactctag cttcccggca acaattaata gactggatgg aggcggataa agttgcagga    4080
ccacttctgc gctcggccct tccggctggc tggtttattg ctgataaatc tggagccggt    4140
gagcgtgggt ctcgcggtat cattgcagca ctggggccag atggtaagcc ctcccgtatc    4200
gtagttatct acacgacggg cagtcaggca actatggatg aacgaaatag acagatcgct    4260
gagataggtg cctcactgat taagcattgg taactgtcag accaagttta ctcatatata    4320
ctttagattg atttaaaact tcatttttaa tttaaaagga tctaggtgaa gatcctttt    4380 gataatctca tgaccaaaat cccttaacgt gagttttcgt tccactgagc gtcagacccc    4440
gtagaaaaga tcaaaggatc ttcttgagat cctttttttc tgcgcgtaat ctgctgcttg    4500
caaacaaaaa aaccaccgct accagcggtg gtttgtttgc cggatcaaga gctaccaact    4560
ctttttccga aggtaactgg cttcagcaga gcgcagatac caaatactgt ccttctagtg    4620
tagccgtagt taggccacca cttcaagaac tctgtagcac cgcctacata cctcgctctg    4680
ctaatcctgt taccagtggc tgctgccagt ggcgataagt cgtgtcttac cgggttggac    4740
tcaagacgat agttaccgga taaggcgcag cggtcgggct gaacgggggg ttcgtgcaca    4800
cagcccagct tggagcgaac gacctacacc gaactgagat acctacagcg tgagcattga    4860
gaaagcgcca cgcttcccga agggagaaag gcggacaggt atccggtaag cggcagggtc    4920
ggaacaggag agcgcacgag ggagcttcca gggggaacg cctggtatct ttatagtcct    4980
gtcgggtttc gccacctctg acttgagcgt cgatttttgt gatgctcgtc agggggggccg    5040 agcctatgga aaaacgccag caacgcggcc ttttacggtt cctggccttt tgctggcct    5100 tttgctcaca tgttctttcc tgcgttatcc cctgattctg tggataaccg tattaccgcc    5160
```

```
tttgagtgag ctgataccgc tcgccgcagc cgaacgaccg agcgcagcga gtcagtgagc    5220
gaggaagcgg aagagcgcct gatgcggtat tttctcctta cgcatctgtg cggtatttca    5280
caccgcatat atggtgcact ctcagtacaa tctgctctga tgccgcatag ttaagccagt    5340
atacactccg ctatcgctac gtgactgcaa ggagatggcg cccaacagtc ccccggccac    5400
ggggcctgcc accatacccca cgccgaaaca agcgctcatg agcccgaagt ggcgagcccg    5460
atcttcccca tcggtgatgt cggcgatata ggcgccagca accgcacctg tggcgccggt    5520
gatgccggcc acgatgcgtc cggcgtagag gatcttgaga tctcgatccg cgaaat       5576
```

<210> SEQ ID NO 12
<211> LENGTH: 4263
<212> TYPE: DNA
<213> ORGANISM: Artificial Sequence
<220> FEATURE:
<223> OTHER INFORMATION: pKL4 plasmid full sequence

<400> SEQUENCE: 12

```
taatacgact cactataggg agaccacaac ggtttccctc tagaaataat tttgtttaac      60
tttaagaagg agatatacat atgcatcacc atcaccatca cgatgtgaag ctggtggaat     120
ctggaggagg cttagtgcag cctggagggt ccctgaaact ctcctgtgca acctctggat     180
tcactttcag tgactattac atgtattggg ttcgccagac tccagagaag aggctggagt     240
gggtcgcata cattagtaat gatgatagtt ccgccgctta ttcagacact gtaaagggcc     300
ggttcaccat ctccagagac aatgccagga acaccctcta cctgcaaatg agccgtctga     360
agtctgagga cacagccata tattcctgtg caagaggact ggcctgggga gcctggtttg     420
cttactgggg ccaagggact ctggtcactg tctctgcagc caaaacgaca ccccccatctg    480 tctatccact ggcccctgga tctgctgccc aaactaactc catggtgacc ctgggatgcc     540
tggtcaaggg ctatttccct gagccagtga cagtgacctg gaactctgga tccctgtcca     600
gcggtgtgca caccttccca gctgtcctgc agtctgacct ctacactctg agcagctcag     660
tgactgtccc ctccagcacc tggcccagcg agaccgtcac ctgcaacgtt gcccacccgg     720
ccagcagcac caaggtggac aagaaaattg tgcccaggga ttgtggtgct aagccttgca     780
tagctacaca agcttccggt ggtggcggat ctggaggtgg cggaagcgga ggtcccgagg     840
tgacaggggg aatggcaagc aagtgggatc agaagggtat ggacattgcc tatgaggagg     900
cggccttagg ttacaaagag ggtggtgttc ctattggcgg atgtcttatc aataacaaag     960
acggaagtgt tctcggtcgt ggtcacaaca tgagatttca aaagggatcc gccacactac    1020
atggtgagat ctccactttg gaaaactgtg ggagattaga gggcaaagtg tacaaagata    1080
ccactttgta tacgacgctg tctccatgcg acatgtgtac aggtgccatc atcatgtatg    1140
gtattccacg ctgtgttgtc ggtgagaacg ttaatttcaa agtaagggc gagaaatatt     1200 tacaaactag aggtcacgag gttgttgttg ttgacgatga gaggtgtaaa agatcatga     1260 aacaattat cgatgaaaga cctcaggatt ggtttgaaga tattggtgag taggaattcg     1320
gctgctaaca aagcccgaaa ggaagctgag ttggctgctg ccaccgctga gcaataacta    1380
gcataacccc ttgggcctct aaacgggtct tgagggttt tttgctgaaa ggaggaacta    1440
tatccggatc ggagatcaat tctggcgtaa tagcgaagag gcccgcaccg atcgccttc    1500 ccaacagttg cgtagcctga atggcgaatg ggacgcgccc tgtagcggcg cattaagcgc    1560
ggcgggtgtg gtggttacgc gcagcgtgac cgctacactt gccagcgccc tagcgcccgc    1620
tcctttcgct ttcttccctt cctttctcgc cacgttcgcc ggctttcccc gtcaagctct    1680
```

```
aaatcggggg ctcccttag ggttccgatt tagtgcttta cggcacctcg accccaaaaa    1740
acttgattag ggtgatggtt cacgtagtgg gccatcgccc tgatagacgg ttttcgccc    1800 tttgacgttg gagtccacgt tctttaatag tggactcttg ttccaaactg aacaacact    1860 caaccctatc tcggtctatt cttttgattt ataagggatt ttgccgattt cggcctattg    1920
gttaaaaaat gagctgattt aacaaaaatt taacgcgaat tttaacaaaa tattaacgtt    1980
tacaatttca ggtggcactt ttcggggaaa tgtgcgcgga accctatt gtttattttt    2040 ctaaatacat tcaaatatgt atccgctcat gagacaataa ccctgataaa tgcttcaata    2100
atattgaaaa aggaagagta tgagtattca acatttccgt gtcgcccta ttcccttttt    2160 tgcggcattt tgccttcctg tttttgctca cccagaaacg ctggtgaaag taaaagatgc    2220
tgaagatcag ttgggtgcac gagtgggtta catcgaactg gatctcaaca gcggtaagat    2280
ccttgagagt tttcgccccg aagaacgttt tccaatgatg agcactttta aagttctgct    2340
atgtggcgcg gtattatccc gtattgacgc cgggcaagag caactcggtc gccgcataca    2400
ctattctcag aatgacttgg ttgagtactc accagtcaca gaaaagcatc ttacggatgg    2460
catgacagta agagaattat gcagtgctgc cataagcatg agtgataaca ctgcggccaa    2520
cttacttctg acaacgatcg gaggaccgaa ggagctaacc gcttttttc acaacatggg    2580 ggatcatgta actcgccttg atcgttggga accggagctg aatgaagcca taccaaacga    2640
cgagcgtgac accacgatgc ctgtagcaat ggcaacaacg ttgcgcaaac tattaactgg    2700
cgaactactt actctagctt cccggcaaca attaatagac tggatggagg cggataaagt    2760
tgcaggacca cttctgcgct cggcccttcc ggctggctgg tttattgctg ataaatctgg    2820
agccggtgag cgtgggtctc gcggtatcat tgcagcactg gggccagatg gtaagccctc    2880
ccgtatcgta gttatctaca cgacgggcag tcaggcaact atggatgaac gaaatagaca    2940
gatcgctgag ataggtgcct cactgattaa gcattggtaa ctgtcagacc aagtttactc    3000
atatatactt tagattgatt taaaacttca ttttaattt aaaaggatct aggtgaagat    3060
cctttttgat aatctcatga ccaaaatccc ttaacgtgag ttttcgttcc actgagcgtc    3120
agaccccgta gaaaagatca aaggatcttc ttgagatcct ttttttctgc gcgtaatctg    3180
ctgcttgcaa acaaaaaaac caccgctacc agcggtggtt tgtttgccgg atcaagagct    3240
accaactctt ttccgaagg taactggctt cagcagagcg cagataccaa atactgtcct    3300
tctagtgtag ccgtagttag gccaccactt caagaactct gtagcaccgc ctacatacct    3360
cgctctgcta atcctgttac cagtggctgc tgccagtggc gataagtcgt gtcttaccgg    3420
gttggactca agacgatagt taccggataa ggcgcagcgg tcgggctgaa cggggggttc    3480
gtgcacacag cccagcttgg agcgaacgac ctacaccgaa ctgagatacc tacagcgtga    3540
gcattgagaa agcgccacgc ttcccgaagg agaaaggcg acaggtatc cggtaagcgg    3600 cagggtcgga acaggagagc gcacgaggga gcttccaggg ggaacgcct ggtatcttta    3660 tagtcctgtc gggtttcgcc acctctgact tgagcgtcga tttttgtgat gctcgtcagg    3720
ggggccgagc ctatggaaaa acgccagcaa cgcggccttt ttacggttcc tggccttttg    3780
ctggcctttt gctcacatgt tctttcctgc gttatcccct gattctgtgg ataaccgtat    3840
taccgccttt gagtgagctg ataccgctcg ccgcagccga acgaccgagc gcagcgagtc    3900
agtgagcgag gaagcggaag agcgcctgat gcggtatttt ctccttacgc atctgtgcgg    3960
tatttcacac cgcatatatg gtgcactctc agtacaatct gctctgatgc cgcatagtta    4020
```

```
agccagtata cactccgcta tcgctacgtg actgcaagga gatggcgccc aacagtcccc    4080
cggccacggg gcctgccacc atacccacgc cgaaacaagc gctcatgagc ccgaagtggc    4140
gagcccgatc ttccccatcg gtgatgtcgg cgatataggc gccagcaacc gcacctgtgg    4200
cgccggtgat gccggccacg atgcgtccgg cgtagaggat cttgagatct cgatccgcga    4260
aat                                                                  4263
```

<210> SEQ ID NO 13
<211> LENGTH: 54
<212> TYPE: PRT
<213> ORGANISM: Artificial Sequence
<220> FEATURE:
<223> OTHER INFORMATION: Extension peptide 1
<220> FEATURE:
<221> NAME/KEY: VARIANT
<222> LOCATION: (1)..(1)
<223> OTHER INFORMATION: X is S or A
<220> FEATURE:
<221> NAME/KEY: VARIANT
<222> LOCATION: (6)..(6)
<223> OTHER INFORMATION: X is S or A
<220> FEATURE:
<221> NAME/KEY: VARIANT
<222> LOCATION: (8)..(8)
<223> OTHER INFORMATION: X is K or Q
<220> FEATURE:
<221> NAME/KEY: VARIANT
<222> LOCATION: (11)..(50)
<223> OTHER INFORMATION: GGGGS is present or absent

<400> SEQUENCE: 13

Xaa Lys Pro Ser Ile Xaa Thr Xaa Ala Ser Gly Gly Gly Gly Ser Gly
1               5                   10                  15

Gly Gly Gly Ser Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Pro Glu
    50

<210> SEQ ID NO 14
<211> LENGTH: 5
<212> TYPE: PRT
<213> ORGANISM: Artificial Sequence
<220> FEATURE:
<223> OTHER INFORMATION: affinity domain

<400> SEQUENCE: 14

Leu Ala Asp Phe Ala
1               5

<210> SEQ ID NO 15
<211> LENGTH: 19
<212> TYPE: PRT
<213> ORGANISM: Artificial Sequence
<220> FEATURE:
<223> OTHER INFORMATION: Extension peptide 2
<220> FEATURE:
<221> NAME/KEY: VARIANT
<222> LOCATION: (1)..(1)
<223> OTHER INFORMATION: X is S or A
<220> FEATURE:
<221> NAME/KEY: VARIANT
<222> LOCATION: (6)..(6)
<223> OTHER INFORMATION: X is S or A
<220> FEATURE:
<221> NAME/KEY: VARIANT
<222> LOCATION: (8)..(8)

```
<223> OTHER INFORMATION: X is K or Q
<220> FEATURE:
<221> NAME/KEY: REPEAT
<222> LOCATION: (11)..(15)

<400> SEQUENCE: 15

Xaa Lys Pro Cys Ile Xaa Thr Xaa Ala Ser Gly Gly Gly Ser Gly
1               5                   10                  15

Gly Pro Glu

<210> SEQ ID NO 16
<211> LENGTH: 14
<212> TYPE: PRT
<213> ORGANISM: Artificial Sequence
<220> FEATURE:
<223> OTHER INFORMATION: Extension peptide 3

<400> SEQUENCE: 16

Cys Lys Pro Ser Ile Ser Thr Lys Ala Ser Gly Gly Pro Glu
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Extension peptide 4

<400> SEQUENCE: 17

Gly Gly Gly Gly Ser
1               5

<210> SEQ ID NO 18
<211> LENGTH: 10
<212> TYPE: PRT
<213> ORGANISM: Artificial Sequence
<220> FEATURE:
<223> OTHER INFORMATION: Extension peptide 5

<400> SEQUENCE: 18

Gly Gly Gly Gly Ser Gly Gly Gly Gly Ser
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Extension peptide 6

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Extension peptide 7
<220> FEATURE:
<221> NAME/KEY: VARIANT
<222> LOCATION: (2)..(2)
<223> OTHER INFORMATION: X is S or A
<220> FEATURE:
<221> NAME/KEY: VARIANT
<222> LOCATION: (4)..(4)
<223> OTHER INFORMATION: X is S or A
```

```
<220> FEATURE:
<221> NAME/KEY: REPEAT
<222> LOCATION: (7)..(11)

<400> SEQUENCE: 20

Ile Xaa Thr Xaa Ala Ser Gly Gly Gly Gly Ser Gly Gly Pro Glu
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Extension peptide 8

<400> SEQUENCE: 21

Gly Ala Ser Gln Glu Asn Asp
1               5

<210> SEQ ID NO 22
<211> LENGTH: 10
<212> TYPE: PRT
<213> ORGANISM: Artificial Sequence
<220> FEATURE:
<223> OTHER INFORMATION: Extension peptide 9

<400> SEQUENCE: 22

Ala Lys Pro Cys Ile Ala Thr Gln Ala Ser
1               5                   10

<210> SEQ ID NO 23
<211> LENGTH: 23
<212> TYPE: DNA
<213> ORGANISM: Artificial Sequence
<220> FEATURE:
<223> OTHER INFORMATION: Primer MH-1

<400> SEQUENCE: 23
taatacgact cactataggg aga                                      23

<210> SEQ ID NO 24
<211> LENGTH: 36
<212> TYPE: DNA
<213> ORGANISM: Artificial Sequence
<220> FEATURE:
<223> OTHER INFORMATION: Primer MH-2

<400> SEQUENCE: 24
agatccgcca ccaccagaag cttttgtact tatgct                        36

<210> SEQ ID NO 25
<211> LENGTH: 62
<212> TYPE: DNA
<213> ORGANISM: Artificial Sequence
<220> FEATURE:
<223> OTHER INFORMATION: Primer MH-3

<400> SEQUENCE: 25
ccagatccgc caccaccact tcccctccc ccggaagctt ttgtacttat gctaggctta   60
ct                                                             62

<210> SEQ ID NO 26
<211> LENGTH: 38
<212> TYPE: DNA
<213> ORGANISM: Artificial Sequence
<220> FEATURE:
```

-continued

<223> OTHER INFORMATION: Primer MH-4

<400> SEQUENCE: 26
tgctggtggc ggatctggag gtcccgaggg cggcaagc                              38

<210> SEQ ID NO 27
<211> LENGTH: 52
<212> TYPE: DNA
<213> ORGANISM: Artificial Sequence
<220> FEATURE:
<223> OTHER INFORMATION: Primer MH-5

<400> SEQUENCE: 27
tggtggtggc ggatctggag gtggcggaag cggaggtccc gagggcggca gc              52

<210> SEQ ID NO 28
<211> LENGTH: 33
<212> TYPE: DNA
<213> ORGANISM: Artificial Sequence
<220> FEATURE:
<223> OTHER INFORMATION: Primer MH-6

<400> SEQUENCE: 28
gccgcgggtg ctgaagctga cgtcgccgcc gtc                                   33

<210> SEQ ID NO 29
<211> LENGTH: 45
<212> TYPE: DNA
<213> ORGANISM: Artificial Sequence
<220> FEATURE:
<223> OTHER INFORMATION: Primer MH-7

<400> SEQUENCE: 29
gggaattcat taagcttgtg tagctatgca aggcttagca ccaca                      45

<210> SEQ ID NO 30
<211> LENGTH: 7
<212> TYPE: PRT
<213> ORGANISM: Artificial Sequence
<220> FEATURE:
<223> OTHER INFORMATION: Extension peptide 10

<400> SEQUENCE: 30

Lys Ala Ser Gly Gly Pro Glu
1               5

<210> SEQ ID NO 31
<211> LENGTH: 5
<212> TYPE: PRT
<213> ORGANISM: Artificial Sequence
<220> FEATURE:
<223> OTHER INFORMATION: Extension peptide 11

<400> SEQUENCE: 31

Ser Lys Pro Cys Gly
1               5

<210> SEQ ID NO 32
<211> LENGTH: 9
<212> TYPE: PRT
<213> ORGANISM: Artificial Sequence
<220> FEATURE:
<223> OTHER INFORMATION: Extension peptide 12

<400> SEQUENCE: 32

Ser Lys Pro Cys Lys Ala Ser Pro Glu

<210> SEQ ID NO 33
<211> LENGTH: 8
<212> TYPE: PRT
<213> ORGANISM: Artificial Sequence
<220> FEATURE:
<223> OTHER INFORMATION: Extension peptide 13

<400> SEQUENCE: 33

Ala Lys Pro Cys Ile Ala Thr Gln
1               5

<210> SEQ ID NO 34
<211> LENGTH: 8
<212> TYPE: PRT
<213> ORGANISM: Artificial Sequence
<220> FEATURE:
<223> OTHER INFORMATION: Extension peptide 14

<400> SEQUENCE: 34

Ser Lys Pro Cys Ile Ser Thr Lys
1               5

<210> SEQ ID NO 35
<211> LENGTH: 15
<212> TYPE: PRT
<213> ORGANISM: Artificial Sequence
<220> FEATURE:
<223> OTHER INFORMATION: Extension peptide 15

<400> SEQUENCE: 35

Gly Gly Gly Gly Cys Gly Gly Gly Gly Ser Gly Gly Gly Gly Ser
1               5                   10                  15

<210> SEQ ID NO 36
<211> LENGTH: 29
<212> TYPE: PRT
<213> ORGANISM: Artificial Sequence
<220> FEATURE:
<223> OTHER INFORMATION: Extension peptide 16

<400> SEQUENCE: 36

Ser Lys Pro Ser Ile Ser Thr Lys Ala Ser Gly Gly Gly Gly Cys Gly
1               5                   10                  15

Gly Gly Ser Gly Gly Gly Gly Ser Gly Gly Pro Glu
            20                  25

<210> SEQ ID NO 37
<211> LENGTH: 43
<212> TYPE: DNA
<213> ORGANISM: Artificial Sequence
<220> FEATURE:
<223> OTHER INFORMATION: Primer 1

<400> SEQUENCE: 37
ggcccatatg catcaccatc accatcacgt gacaggggga atg          43

<210> SEQ ID NO 38
<211> LENGTH: 35
<212> TYPE: DNA
<213> ORGANISM: Artificial Sequence
<220> FEATURE:
<223> OTHER INFORMATION: Primer 2

<400> SEQUENCE: 38

```
ttggtttgaa gatattggtg agtaggaatt cggcc                           35
```

<210> SEQ ID NO 39
<211> LENGTH: 25
<212> TYPE: DNA
<213> ORGANISM: Artificial Sequence
<220> FEATURE:
<223> OTHER INFORMATION: Primer 3

<400> SEQUENCE: 39

```
ggcccccgag gtgacagggg gaatg                                      25
```

<210> SEQ ID NO 40
<211> LENGTH: 46
<212> TYPE: DNA
<213> ORGANISM: Artificial Sequence
<220> FEATURE:
<223> OTHER INFORMATION: Primer 4

<400> SEQUENCE: 40

```
gaagatattg gtgagcatca ccatcaccat cactaggaat tcggcc               46
```

<210> SEQ ID NO 41
<211> LENGTH: 49
<212> TYPE: DNA
<213> ORGANISM: Artificial Sequence
<220> FEATURE:
<223> OTHER INFORMATION: Primer 5

<400> SEQUENCE: 41

```
ggcccatatg catcaccatc accatcacga tgtgaagctg gtggagtct            49
```

<210> SEQ ID NO 42
<211> LENGTH: 14
<212> TYPE: PRT
<213> ORGANISM: Artificial Sequence
<220> FEATURE:
<223> OTHER INFORMATION: Extension peptide 17

<400> SEQUENCE: 42

```
Ser Lys Pro Ser Ile Ser Thr Lys Ala Ser Gly Gly Pro Glu
1               5                   10
```

<210> SEQ ID NO 43
<211> LENGTH: 44
<212> TYPE: PRT
<213> ORGANISM: Artificial Sequence
<220> FEATURE:
<223> OTHER INFORMATION: Extension peptide 18

<400> SEQUENCE: 43

```
Ser Lys Pro Ser Ile Ser Thr Lys Ala Ser Gly Gly Gly Gly Ser Gly
1               5                   10                  15
Gly Gly Gly Ser Gly Gly Gly Cys Gly Gly Gly Ser Gly Gly
            20                  25                  30
Gly Gly Ser Gly Gly Gly Gly Ser Gly Gly Pro Glu
        35                  40
```

<210> SEQ ID NO 44
<211> LENGTH: 54
<212> TYPE: PRT
<213> ORGANISM: Artificial Sequence
<220> FEATURE:
<223> OTHER INFORMATION: Extension peptide 19

<400> SEQUENCE: 44

Ser Lys Pro Ser Ile Ser Thr Lys Ala Ser Gly Gly Gly Gly Ser Gly
1               5                   10                  15

Gly Gly Gly Ser Gly Gly Gly Ser Gly Gly Gly Ser Gly Gly
            20                  25                  30

Gly Gly Cys Gly Gly Gly Ser Gly Gly Gly Ser Gly Gly
        35                  40                  45

Gly Ser Gly Gly Pro Glu
        50

<210> SEQ ID NO 45
<211> LENGTH: 64
<212> TYPE: PRT
<213> ORGANISM: Artificial Sequence
<220> FEATURE:
<223> OTHER INFORMATION: Extension peptide 20

<400> SEQUENCE: 45

Ser Lys Pro Ser Ile Ser Thr Lys Ala Ser Gly Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Ser Gly Gly Gly Cys Gly Gly
        35                  40                  45

Gly Ser Gly Gly Gly Ser Gly Gly Gly Ser Gly Pro Glu
        50                  55                  60

<210> SEQ ID NO 46
<211> LENGTH: 14
<212> TYPE: PRT
<213> ORGANISM: Artificial Sequence
<220> FEATURE:
<223> OTHER INFORMATION: Extension peptide 21

<400> SEQUENCE: 46

Ser Lys Pro Cys Ile Ser Thr Lys Ala Ser Gly Gly Pro Glu
1               5                   10

<210> SEQ ID NO 47
<211> LENGTH: 19
<212> TYPE: PRT
<213> ORGANISM: Artificial Sequence
<220> FEATURE:
<223> OTHER INFORMATION: Extension peptide 22

<400> SEQUENCE: 47

Ser Lys Pro Cys Ile Ser Thr Lys Ala Ser Gly Gly Gly Gly Ser Gly
1               5                   10                  15

Gly Pro Glu

<210> SEQ ID NO 48
<211> LENGTH: 24
<212> TYPE: PRT
<213> ORGANISM: Artificial Sequence
<220> FEATURE:
<223> OTHER INFORMATION: Extension peptide 23

<400> SEQUENCE: 48

Ser Lys Pro Cys Ile Ser Thr Lys Ala Ser Gly Gly Gly Gly Ser Gly
1               5                   10                  15

Gly Gly Ser Gly Gly Pro Glu
            20

<210> SEQ ID NO 49
<211> LENGTH: 29
<212> TYPE: PRT
<213> ORGANISM: Artificial Sequence
<220> FEATURE:
<223> OTHER INFORMATION: Extension peptide 24

<400> SEQUENCE: 49

Ser Lys Pro Cys Ile Ser Thr Lys Ala Ser Gly Gly Gly Gly Ser Gly
1               5                   10                  15

Gly Gly Gly Ser Gly Gly Gly Ser Gly Gly Pro Glu
            20                  25

<210> SEQ ID NO 50
<211> LENGTH: 24
<212> TYPE: PRT
<213> ORGANISM: Artificial Sequence
<220> FEATURE:
<223> OTHER INFORMATION: Extension peptide 25

<400> SEQUENCE: 50

Ala Lys Pro Cys Ile Ala Thr Gln Ala Ser Gly Gly Gly Gly Ser Gly
1               5                   10                  15

Gly Gly Gly Ser Gly Gly Pro Glu
            20

<210> SEQ ID NO 51
<211> LENGTH: 34
<212> TYPE: PRT
<213> ORGANISM: Artificial Sequence
<220> FEATURE:
<223> OTHER INFORMATION: Extension peptide 26

<400> SEQUENCE: 51

Ser Lys Pro Cys Ile Ser Thr Lys Ala Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Pro Glu

<210> SEQ ID NO 52
<211> LENGTH: 39
<212> TYPE: PRT
<213> ORGANISM: Artificial Sequence
<220> FEATURE:
<223> OTHER INFORMATION: Extension peptide 27

<400> SEQUENCE: 52

Ser Lys Pro Cys Ile Ser Thr Lys Ala Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Pro Glu
        35

<210> SEQ ID NO 53
<211> LENGTH: 44
<212> TYPE: PRT
<213> ORGANISM: Artificial Sequence
<220> FEATURE:
<223> OTHER INFORMATION: Extension peptide 28

<400> SEQUENCE: 53

-continued

Ser Lys Pro Cys Ile Ser Thr Lys Ala Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Ser Gly Gly Pro Glu
        35                  40

<210> SEQ ID NO 54
<211> LENGTH: 49
<212> TYPE: PRT
<213> ORGANISM: Artificial Sequence
<220> FEATURE:
<223> OTHER INFORMATION: Extension peptide 29

<400> SEQUENCE: 54

Ser Lys Pro Cys Ile Ser Thr Lys Ala Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Ser Gly Gly Pro
        35                  40                  45

Glu

<210> SEQ ID NO 55
<211> LENGTH: 54
<212> TYPE: PRT
<213> ORGANISM: Artificial Sequence
<220> FEATURE:
<223> OTHER INFORMATION: Extension peptide 30

<400> SEQUENCE: 55

Ser Lys Pro Cys Ile Ser Thr Lys Ala Ser Gly Gly Gly Ser Gly
1               5                   10                  15

Gly Gly Gly Ser Gly Gly Gly Ser Gly Gly Gly Ser Gly Gly Gly
            20                  25                  30

Gly Gly Ser Gly Gly Gly Gly Ser Gly Gly Gly Ser Gly Gly Gly
        35                  40                  45

Gly Ser Gly Gly Pro Glu
    50

<210> SEQ ID NO 56
<211> LENGTH: 5
<212> TYPE: PRT
<213> ORGANISM: Artificial Sequence
<220> FEATURE:
<223> OTHER INFORMATION: PE38REDLK

<400> SEQUENCE: 56

Arg Glu Asp Leu Lys
1               5

<210> SEQ ID NO 57
<211> LENGTH: 24
<212> TYPE: PRT
<213> ORGANISM: Artificial Sequence
<220> FEATURE:
<223> OTHER INFORMATION: pKL2

<400> SEQUENCE: 57

Ser Lys Pro Cys Ile Ser Thr Lys Ala Ser Gly Gly Gly Ser Gly
1               5                   10                  15

Gly Gly Gly Ser Gly Gly Pro Glu

-continued

```
<210> SEQ ID NO 58
<211> LENGTH: 24
<212> TYPE: PRT
<213> ORGANISM: Artificial Sequence
<220> FEATURE:
<223> OTHER INFORMATION: pKL3

<400> SEQUENCE: 58

Ser Lys Pro Cys Ile Ser Thr Lys Ala Ser Gly Gly Gly Ser Gly
1               5                   10                  15

Gly Gly Gly Ser Gly Gly Pro Glu
            20

<210> SEQ ID NO 59
<211> LENGTH: 24
<212> TYPE: PRT
<213> ORGANISM: Artificial Sequence
<220> FEATURE:
<223> OTHER INFORMATION: pKL4

<400> SEQUENCE: 59

Ala Lys Pro Cys Ile Ala Thr Gln Ala Ser Gly Gly Gly Ser Gly
1               5                   10                  15

Gly Gly Gly Ser Gly Gly Pro Glu
            20
```

DIMER OF CHIMERIC RECOMBINANT BINDING DOMAIN-FUNCTIONAL GROUP FUSION FORMED VIA DISULFIDE-BOND-BRIDGE AND THE PROCESSES FOR PRODUCING THE SAME

CROSS REFERENCE TO RELATED APPLICATIONS

This patent application claims the benefit of priority from Korean Patent Application No. 10-2003-0043599 filed Jun. 30, 2003 through PCT Application Serial No. PCT/KR2004/001595 filed Jun. 30, 2004 the contents of which are incorporated herein by reference.

TECHNICAL FIELD

This invention is related to the dimer of chimeric recombinant binding domain-functional group fusion([B-F fusion]$_2$) by using disulfide-bond-bridge connecting the two of a monomer of chimeric recombinant binding domain-functional group fusion(B-F fusion) and method for producing the said dimer.

BACKGROUND ART

The dimer of chimeric recombinant binding domain(B)-functional group(F) fusion was the first to be formed by using disulfide-bond-bridge to connect monomers having twice number of binding domain, and it has higher efficiency for targeting its functional group to the targets than the monomer and the production yield is high containing said extension peptide chain(LFA, lath flexible amino acid).

The fusions of binding domain and heterogeneous functional group have been made of various kinds of binding domains and heterogeneous functional groups.

Antibody is a typical use of binding domain[Reference: Hall, Walter A., Immunotoxin Method and Protocols, *Method in Molecular Biology* Vol 166, Humana Press, Totowa, N.J.]. Antibody has been studied with changing its binding region through recombination and modification maintaining its binding affinity and binding specificity. For examples, there are scFv, pFv, dsFv, Fab, L(using one light chain), LL(using two light chains), H(using one heavy chain), HH(using two heavy chains), diabody, triabody, tetrabody, double headed antibody and others[Reference: Brinkmann, U., et al., *J. Mol. Biol.* 268, 107~117, 1997, Chaudhary, V. K., et al., *Nature* 339, 394~397, 1989, Webber, K. O., et al., *Mol. Immunol.* 4, 249~258, 1995, Yokota, T., et al., *Cancer Res.* 52, 3402~3408, 1992, Kreitman R. J., et al., *Leukemia* 7(4), 553~562, 1993, Pluckthun A. and Pack P., *Immunotechnology* 3, 83, 1997, Hollinger, P., et al., *Protein Eng.* 9, 299~305, 1996, Atwell J., et al., *Protein Eng.* 12, 597~604, 1999, Iliades P., et al., *FEBS Lett.* 409, 437, 1997]. These fragments of antibody binding regions have been used independently without fusing to functional groups or used as a fusion with functional groups which provokes physiological responses to target cells to deliver the functional group specifically.

Also, examples for use as binding domain are, many kinds of ligands or fragments which have ligand binding affinity, for example, TGF alpha, TGF beta, IL2, IL6, TNF, GMSCF and more. And they include many kinds of ligand receptors or fragments which have receptor binding affinity, for example, TBP1, TBP2, IFN alpha or beta receptor, gonadotropin receptor and other receptors.

There are many functional groups that have been used in fusion with binding domains [Reference: Hall, Walter A., Immunotoxin Method and Protocols, Method in Molecular Biology Vol 166, Humana Press, Totowa, N.J.]. For example, enzymes that have functions in prodrug transformation, material detection, decomposition, formation, proteins containing cytotoxic functional group and other functional group, organisms including the viruses for gene therapy, compounds that form cationic tail for delivering DNA, drug compounds, liposomes for drug delivery, biosensors for detecting real time target molecule and many others are used as functional group for fusion[Reference: (Hudson, P. J., *Curr Opin Immunol* 11(5), 548~5, 1999)(Bagshawe, K. D., et al., *Curr Opin Immunol* 11(5), 579~83, 1999)].

Antibody-toxin functional group fusion is a molecule which has cytotoxic factor connected via chemical or genetic method with antibodies as specific cell binding-domain [Reference: Cobb, P. W., et al., *Semin Hematol* 29, 6~13, 1992]. Antibody-toxin functional group fusion was expected to be successful in cancer treatment after the development of the antibody recognizing cancer cell.

Antibody-toxin functional group fusion in its early stages was made by connecting two proteins via protein chemical cross-linking reaction, but in accordance with the development of recombinant DNA technology, it was produced in various forms of recombinant protein through genetic fusion. The incipient of antibody-toxin fusion(mAb-toxin) made by protein chemical cross-linking showed high stability of the fusion protein in blood and it exterminated the cancer cells at clinical demonstration[Reference: Pai, L. H., et al., *Cancer Res.* 52, 3189~93, 1992] but, the damages on antibody caused during chemical reaction and inactivate molecules produced by chemical side reactions remained as problems.

These problems were solved mostly through recombinant DNA technology. Genetic engineering allowed genetically fusing the essential elements for antibody-toxin fusion to make molecules in purity and homogenously, and also it allowed small molecular weighted-proteins to be designed and produced[Reference: Pai, L. H., et al., *Proc Natl Acad Sci USA* 88, 3358~3362, 1991]. For the minimum domain for antibody-toxin functional group fusion, the variable region of the antibody for binding (except constant region) and toxic enzymatic region of toxin (except cell-binding domain of toxin) [Reference: Kondo, T., et al., *J Biol Chem* 263, 9470~9475, 1988] was used. However, nowadays binding domains and toxic domains themselves are modified to be made as derivatives for better activity[Reference: (Pastan, I., et al., *Science* 254, 1173~1177, 1991)(Pastan, I., et al., *Proc Natl Acad Sci USA* 88, 3358~3362, 1991)(Vitetta, E. S., et al., *Cell Biology* 2, 47~58, 1991) (Allured, V. S., et al., *Proc. Natl. Acad. Sci. USA* 83, 1320~1324, 1986) (Hwang, J et al., *Cell* 48, 129~136, 1987)].

The modified antibody binding region produced by genetic recombination can be classified in 4 types. These are scFv (single chain Fv form) characterized in connecting the minimum binding unit of antibody $V_H$ and $V_L$ with 15 amino acid polypeptide linker (Gly$_4$Ser$_4$) [Reference: Buchner, J., et al., *Anal Biochem* 205, 263~70, 1992], dsFv(disulfide-stabilized Fv form) characterized by connecting $V_H$ and $V_L$ via disulfide bonds, pFv(permutated Fv form) characterized in connecting $V_H$ and $V_L$ with base loop and Fab form etc. scFv-toxin functional group form has the smallest molecular weight from antibody binding domain produced and for this it was expected to have good penetration ability into cancer tissues showing good cytotoxicity. However, the low productions yield[Reference: (Buchner, J., et al., *Anal Biochem* 205, 263~70, 1992)(Brinkmann. U., et al., *Proc. Natl. Acad. Sci. USA* 88, 8616~8620, 1991)] and short half life in animal blood circulation[Reference: Brinkmann. U., et al., *Proc.*

*Natl. Acad. Sci. USA* 89, 3065~3069, 1992] were problems and there were no effects observed from results of clinical demonstration.

dsFv-toxin functional group has similar size with scFv-toxin functional group and made to have high stability in animal blood circulation. This type of antibody-toxin functional group was more stable than scFv toxin in blood circulation but the cytotoxicity test with cultured cell in vitro showed similar results[Reference: (Pastan, I., et al., *Science* 254, 1173~1177, 1991) (Pastan, I., et al., *Cancer Research* 51, 3781~3787, 1991)]. Results on dsFv distribution tests in animal with radionuclide labeled dsFv-toxin functional group[Reference: Choi, C., et al., *Cancer Res.* 55, 5323~9, 1995] showed that dsFv disappeared from the blood circulation through excretion more fast than to bind with cancer cells and accumulate.

pFv is made by connecting the β-strand between 3 and 3b on $V_L$ and β-strand between 3 and 3b on $V_H$[Reference: Brinkmann, U., et al., *J Mol Biol* 268, 107~17, 1997]. However, this form of antibody-toxin functional group showed short half-life rate, low production yield, and no improved cytotoxicity effect.

Recombinant Fab-toxin functional group fusion was made to overcome the problem mentioned above[Reference (Ghetie, M. A., et al., 1991)(Kreitman, R. J., et al., *Cancer Res* 53, 819~25, 1993)(Choe, M., et al., *Cancer Res* 54,3406~7, 1994) (Kreitman, R. J et al., *Int J Cancer* 57,856~64, 1994)]. This molecule showed similar half life of activity in blood circulation as the incipient antibody-toxin functional group chemical fusion(mAb-toxin) although it was a recombinant antibody-toxin functional group fusion and was more stable than scFv-toxin functional group, dsFv toxin functional group, pFv-toxin functional group in structure[Reference: (Choe, M., et al., *Cancer Res.* 54, 3460~7, 1994)(Kreitman, R. J., et al., *Int J Cancer* 57, 856~64, 1994)]. Also, the production yield of refolding was 10 times higher in maximum [Reference: (Buchner, J., et al., *Bio/Technology* 9, 157~162, 1991)(Buchner, J., et al., *Anal Biochem* 205, 263~70, 1992)]. Even though the Fab-toxin functional group in blood circulation was more active than scFv, the therapeutic efficacy towards cancer cells in animal model was good or had no big difference according to antibody type. The reason it had no big difference was assumed to be that Fab-toxin functional group has a bigger binding domain that each of the quaternary structure of Fab didn't form properly during refolding or it has two more intrachain disulfide bond to make disulfide bond incomplete or make disulfide bond scrambled or the cysteins for interchain disulfide bond between heavy and light chain did not form disulfide bond completely or got scrambled. Therefore, the complete structure formation of molecule was disturbed to have abnormal binding affinity against antigen and these may have mixed with the normal molecules to lower the efficacy[Reference: Choe, M., et al., *Cancer Res* 54. 3460~7, 1994].

In this way, the Fab-toxin functional group has weak binding affinity because the isolation and removal of the inactivated molecules and molecules with disulfide bond scrambled or incomplete formed is very difficult. According to these results, the recombinant antibody-toxin functional groups with the best stability in structure and appropriate half-life are Fab-toxin functional group form. To explain this biochemically, $C_{H1}$ and $C_L$ and the disulfide bond between light and heavy chain give high stability to quaternary structure, and the resistance against degradation and clearance will be strong. The most important issue of the antibody-toxin functional group is stability and affinity.

Therefore, development of new antibody-toxin functional group is needed with improved stability and affinity to have high efficacy for targets and high productivity. To increase structural stability, the number of disulfide bond can be increased but if wrong bonds form or scrambling happen molecules with inactive structures are produced and the production yield lowers or doesn't produce it at all.

In addition to the described molecules mentioned above, there are toxin functional group-antibody fusions, which have toxin functional group on the amino terminal and antibody binding domain on the carboxyl terminal and they showed similar results.

Also, antibody derivatives with multiple binding domains were produced to increase binding affinity and they are diabody, triabody, tetrabody, double headed antibody and others [Reference: Takemura S., et al., *Cancer Immunol Immunother.* 51(1): 33~44, 2002]. Increasing the numbers of binding domains two, three, four times and with the affinities between the chains composing binding domains, multiple binding domain derivatives are made. They showed that the binding affinity increased by the increase of binding domain numbers and there was no report before about these molecules being fused with heterogeneous functional groups to produce chimeric fusion. It is a difficult matter to connect binding domain to functional group without hindrance to each other and between the functional group themselves in forming dimeric form of the chimeric fusion and manufacturers concerned will know that this is the key to successful production. If the extension chain, which connects binding domain and functional group, disturbs the refolding of the big chains of binding domain or functional group or some hindrance occurs between the big chains, no production will occur.

Also, when the Cysteine lacking intrachain disulfide bond counterpart cysteine is added in the extension sequence connecting binding domain and functional group this may form disulfide bond with other Cysteine, which has its right counterpart, and this may lead to disulfide bond structure scrambling. In this case the uncoupled Cysteine that has no natural disulfide bond counterpart will form wrong disulfide bonds to ruin sterical structure of the molecule and lose its activity. And also, it is natural to think that if the extension chain containing uncoupled Cysteine has lots of flexible amino acids to be long making the extension chain have no regular structure, it is easier for the uncoupled Cysteine to intermix with other naturally coupled Cysteine in neighboring big structure. The inventors experienced these kinds of failures in producing active dimer molecules and it will be thought as a special and incidental case when the manufacturers concerned produce one of these types of molecule.

If the problems and limits mentioned above are overcome by new findings about forming dimers with disulfide bond generally, the dimer of binding domain(B)-functional group (F) fusion by disulfide bond will be possible by the manufacturers concerned.

On the other side, there were reports about compared studies of various structures of molecules[Reference: Bera, T. K., et al., *Bioconjug Chem* 9(6), 736~4, 1998] but no reports were found about producing dimer[antibody-toxin functional group]$_2$ by using disulfide bonding between antibody-toxin functional groups fusion to form molecules with double binding valency. Therefore, it has been expected that the manufacturers will be able to know how extension peptide chain to be put in between big sequences of antibody and toxin functional group and how the uncoupled Cysteine to be put in to extension peptide chain to form disulfide bonds for dimerization after the understanding about the refolding process forming the tertiary and quaternary structure of the protein.

DETAILED DESCRIPTION OF THE INVENTION

Technical Problem

Figure 1:
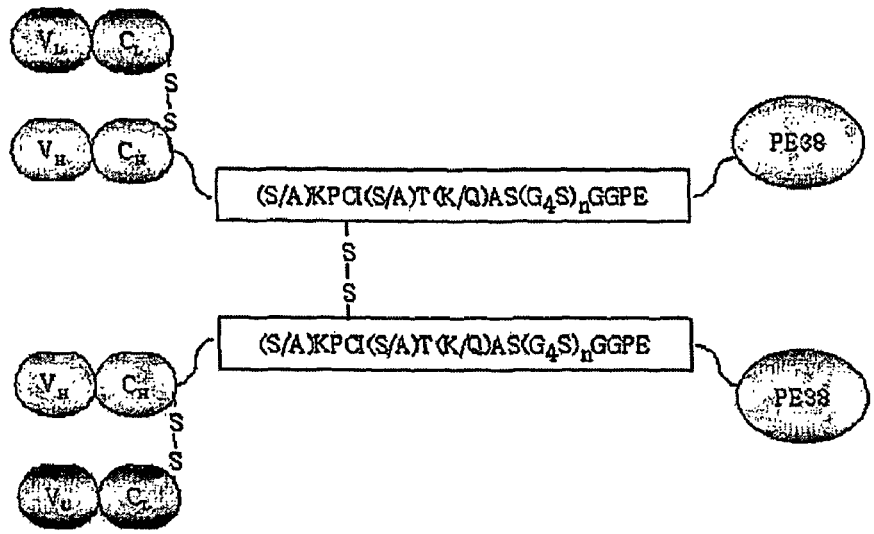
FIG. 1 is a structure of the dimer of chimeric recombinant binding domain(B)-functional group(F) fusion with double binding valency produced from pMH21, 22, 23 and pMHS22. The sequence shown is SEQ ID NO:15.

The technical task of this invention is fusing binding domain(B) with heterogeneous functional group(F) to form a monomer of chimeric recombinant binding domain-functional group fusion(B-F fusion) and connecting two of these with covalent disulfide-bond-bridge to make a dimer of chimeric recombinant binding domain-functional group fusion ([B-F fusion]$_2$) with double binding valency of the monomer.

Technical Solution

This invention is related to a method producing dimer of chimeric recombinant binding domain-heterogeneous functional group fusion([B-F fusion]$_2$) with double binding valency of the monomer by using covalent disulfide-bond-bridge connecting the two of a monomer of chimeric recombinant binding domain-heterogeneous functional group fusion(B-F fusion).

In a concrete way, two monomer is connected to become a dimer by disulfide-bond-bridge formed by the oxidation reaction between the two uncoupled Cys that is on any of 1~45 amino acid position of extension peptide chain (Ext) which extends from binding domain to functional group for fusion.

At this time, said extension peptide chain (Ext, extension amino acid sequence) is firstly composed of peptide linker(L) from the last of the uncoupled Cys to functional group(end of Ext) and composed of 1~50 amino acids from the last of the uncoupled Cys to functional group. Secondly, said extension peptide chain (Ext, extension amino acid sequence) is composed of peptide linker(L) from the last of the uncoupled Cys to functional group(end of Ext), and said peptide linker(L) is a peptide linker containing an affinity domain(LAD) which has homomeric self affinity or heteromeric affinity making the domain to assemble and leading to the formation of homomeric multimer or heteromeric multimer, and the amino acid sequence from the end of said affinity domain(AD) to functional group(end of Ext) is composed of 1~50 amino acids. Thirdly, said extension peptide chain(Ext, extension amino acid sequence) is composed of peptide linker(L) from the last of the uncoupled Cys to functional group(end of Ext), and said peptide linker(L) is a flexible amino acid sequence peptide linker(LFA) which contains non-bulky amino acids like Glycine(G) or Alanine(A) or Serine(S) or Glutamine(Q) or Glutamic acid(E) or Asparagine(N), Aspartic acid(D), and the amino acid sequence from the last of the uncoupled Cys to functional group is composed of 1~50 amino acids. Fourthly, said extension peptide chain(Ext, extension amino acid sequence) is composed of peptide linker(L) from the last of the uncoupled Cys to functional group (end of Ext), and said peptide linker(L) is a peptide linker containing an affinity domain(LAD) which has homomeric self affinity or heteromeric affinity making the domain to assemble and leading to the formation of homomeric multimer or heteromeric multimer, and said peptide linker(L) is also a flexible amino acid sequence peptide linker(LFA) which contains non-bulky amino acids like Glycine(G) or Alanine(A) or Serine(S) or Glutamine(Q) or Glutamic acid(E) or Asparagine(N), Aspartic acid(D), and the amino acid sequence from the end of said affinity domain(AD) to functional group(end of Ext) is composed of 1~0 amino acids.

On the other side, the binding domain on the chimeric recombinant binding domain-heterogeneous functional group fusion is composed of multiple chains(B1,B2, ..., Bn) and one of the chain(B1) of binding domain is connected to extension peptide chain that has the cysteine for the disulfide-bond-bridge between two monomer and another chain(B2) is connected to heterogeneous functional group.

At this time, said extension peptide chain(Ext) which is connected to one of the chain(B1) comprises firstly, uncoupled Cys on any of 1~45 amino acids position on the extension peptide chain. Secondly said extension peptide chain comprises uncoupled Cys on any of 1~45 amino acids position and comprises peptide linker(L) from the last uncoupled Cys to the end of extension peptide chain. Thirdly, said extension peptide chain comprises uncoupled Cys on any of 1~45 amino acids position and comprises peptide linker(L) from the last uncoupled Cys to the end of extension peptide chain and said peptide linker(L) has homomeric self affinity or heteromeric affinity domain(AD) making the domain to assemble and leading to the formation of homomeric multimer or heteromeric multimer. Fourthly, said extension peptide chain comprises uncoupled Cys on any of 1~45 amino acids position and comprises peptide linker(L) from the last uncoupled Cys to the end of extension peptide chain and said peptide linker(L) has homomeric self affinity or heteromeric affinity domain(AD) making the domain to assemble and leading to the formation of homomeric multimer or heteromeric multimer and said peptide linker(L) comprises flexible amino acid sequence with non-bulky amino acids like Glycine(G) or Alanine(A) or Serine(S) or Glutamine(Q) or Glutamic acid(E) or Asparagine(N), Aspartic acid(D).

At this time, another chain(B2) firstly, has functional group (F) at the end of the chain. Secondly, has functional group(F) at the end of the peptide linker(L) connected to the end of the chain and said peptide linker comprises 1~50 amino acids. Thirdly, has functional group(F) at the end of the peptide linker(L) connected to the end of the chain and said peptide linker(L) is flexible amino acid sequence peptide linker(LFA) which comprises Glycine(G) or Alanine(A) or Serine(S) or Glutamine(Q) or Glutamic acid(E) or Asparagine(N), Aspartic acid(D) and said peptide linker(L) comprises 1~50 amino acids.

Binding domain(B) is adhesive protein or amino acid sequence having adhesive fragment for instance, antibody, fragment of antibody like scFv, pFv, dsFv, Fab, L(using 1 light chain), LL(using 2 light chains), H(using 1 heavy chain), HH(using 2 heavy chains), diabody, triabody, tetrabody, double-headed antibody, ligands for example, TGF alpha, TGF beta, IL2, IL6, TNF, GMSCF Granulocyte Macrophage Colony Stimulating Factor) or some fragments having ligand's affinity, all kinds of ligand receptors for example, insulin receptor, TBP1, TBP2, IFN alpha or beta receptor, gonadotropin receptor or some fragments having receptor's affinity and sequences having binding affinity.

Functional group(F) is a functional group with all kinds of physiological functions including enzymes used in prodrug transformation, detection, decomposition, formation of materials and proteins containing toxin-functional group which has cytotoxicity, organisms like viruses for gene therapy, compounds with cationic tail for delivering DNA, drug compounds, liposome for drug delivery, biosensor for detecting real time target molecule.

The dimer of chimeric recombinant binding domain(B)-heterogeneous functional group(F) fusion was the first to be formed by using disulfide-bond-bridge to connect monomers having twice as high binding valency, and it has higher functional efficiency to its targets and the production yield is high containing said extension peptide chain.

Namely, from one point of view, this invention offers dimer of chimeric recombinant binding domain-functional group fusion([B-F fusion]$_2$) with double binding valency by using disulfide-bond-bridge connecting the two of a monomer of chimeric recombinant binding domain-functional group fusion([B-F fusion]).

In another point of view, this invention offers polypeptides used in producing dimer of chimeric recombinant binding domain-functional group fusion([B-F fusion]$_2$) with double binding valency by using disulfide-bond-bridge connecting the two of a monomer of chimeric recombinant binding domain-functional group fusion([B-F fusion]).

In another point of view, this invention offers recombinant plasmid containing genes coding polypeptides used in producing dimer of chimeric recombinant binding domain-functional group fusion([B-F fusion]$_2$) with double binding valency by using disulfide-bond-bridge connecting the two of a monomer of chimeric recombinant binding domain-functional group fusion([B-F fusion]).

Something to make clear in this invention is concluding not only the amino acid sequence of binding domain(B)-functional group(F) protein but concluding all the nucleotide sequences coding the same protein. Actually, all the nucleotide sequences means all the different DNA sequences which codes the same amino acid using different codons to code same amino acids.

PCR is mostly used to produce chimeric recombinant binding domain(B)-functional domain(F) fusion coding sequences by using oligonucleotide primers made from clones which has genes coding the protein we want.

The invention chimeric recombinant binding domain(B)-functional domain(F) fusion can be expressed in high class eukaryotic cell(for example, yeast, insects or mammalian cells) or prokaryotic cell of microorganism using appropriate expression vector. Any method known in this field can be used.

For example, chimeric recombinant binding domain(B)-functional domain(F) fusion protein coding DNA produced from said any method referred above can be inserted into appropriate expression vector. Double strand cDNA is inserted into the vector by using synthesized DNA linker or blunt-ended DNA ligation or restriction enzyme treated DNA ligation or terminal polymerase treated DNA ligation. DNA ligase is used in DNA molecules ligation and alkaline phosphatase is used in removing the phosphate group.

Expression vector must have specific nucleotides elements for mRNA transcription and translation into protein from the coding DNA sequence. Promoter is needed for the RNA polymerase to recognize for transcription. RNA polymerase binds to this promoter to start transcription. Promoters used are various on general but has different efficiency.

In another point of view, this invention offers host cells including recombinant vectors cloned with genes coding polypeptides used in producing dimer of chimeric recombinant binding domain-functional group fusion([B-F fusion]$_2$) by using disulfide-bond-bridge connecting the two of a monomer of chimeric recombinant binding domain-functional group fusion([B-F fusion]).

According to eukaryotic hosts, it varies with control sequences for transcription and translation. These are regulatory signals related to highly expressed genes and can be gained from viruses like adenovirus, cow papillomavirus, anthropoid virus. For example, there are TK promoter from Herpes virus, SV40 early promoter, gal4 gene promoter from yeast and more. There are transcription start control signals that can both inhibit or promote the expression of the gene to be selected for use.

Transformation, transfection, conjugation, protoplast fusion, electroporation, calcium phosphate-precipitation, direct microinjection and others can insert the expression vector into host cell.

Host cells are prokaryotic or eukaryotic cells. Eukaryotic cells are preferable for example, mammalian cells like human, monkey, mouse, Chinese hamster ovarian cell(CHO) because these cells offer correct folding or modification of proteins like glycosylation. Also, in yeast cells modification including glycosylation takes place after protein expression. Yeast cells provide high copy numbers of recombinant vectors in the cell and transcription efficiency is high. The yeast recognizes the guidance sequence of protein secretion signal of the cloned mammalian gene and secretes the peptide(precursor protein) which has the signal.

In another point of view, this invention offers method to produce chimeric recombinant binding domain-functional group fusion([B-F fusion]$_2$) through host cells including recombinant vectors cloned with genes coding polypeptides used in producing dimer of chimeric recombinant binding domain-functional group fusion([B-F fusion]$_2$) by using disulfide-bond-bridge connecting the two of a monomer of chimeric recombinant binding domain-functional group fusion ([B-F fusion]).

In another point of view, this invention offers pharmaceutical compounds containing chimeric recombinant binding domain-functional group fusion([B-F fusion]$_2$).

The dimeric form of chimeric recombinant binding domain-functional group fusion([B-F fusion]$_2$) with double binding valency is indicated as a formula below.

[Binding domain(B)-Ext-F]$_2$      (I)

The binding sequence(B) in said formula(I) above is adhesive protein or adhesive fragment containing amino acid sequence;

Ext is extension peptide chain(extension sequence) extended from binding domain(B) to functional group(F) to fuse them, and disulfide-bond-bridge is formed between the monomers by the oxidation of two uncoupled Cys on the extension peptide chain(Ext) to produce dimer, or said extension peptide chain comprises peptide linker(L) from the last uncoupled Cys to the end of extension peptide chain or said peptide linker is an affinity domain(AD) containing peptide linker(LAD) which has homomeric self affinity or heteromeric affinity leading to the formation of homomeric multimer or heteromeric multimer domain, or said peptide linker (L) is flexible amino acid(FA) sequence peptide linker(LFA) which has non-bulky amino acids like Glycine(G) or Alanine (A) or Serine(S) or Glutamine(Q) or Glutamic acid(E) or Asparagine(N), Aspartic acid(D) or said peptide linker having affinity domain(AD) with homomeric self affinity or heteromeric affinity comprising muldimer domains and having non-bulky amino acids like Glycine(G) or Alanine(A) or Serine(S) or Glutamine(Q) or Glutamic acid(E) or Asparagine(N), Aspartic acid(D) to be a flexible amino acid sequence peptide linker with affinity domain(LADFA) (SEQ ID NO: 14) so to be a sequence as [B-Ext or Ext(L) or Ext(LAD) or Ext(LFA) or Ext(LADFA) (SEQ ID NO: 14)-F] in its monomer form;

F is for physiological functional group like enzyme, protein with physiological (e.g. toxic) function, organisms like viruses, compounds, drug compounds for treatment, liposome, biosensor, pro-drug and more[Reference: (Farah, R. A., et al., *Crit. Rev. Eukaryot. Gene Expr.* 8, 321~356, 1998) (Trail, P. A., et al., *Science* 261, 212~215, 1993)(Hinman, L. M., et al., *Cancer res.* 53, 3336~3342, 1993) (Pastan, *I. Biochem. Biophys. Acta* 1333, C1~C6, 1997)(Kreitman, P. J., et al., *J. Clin. Oncol.* 18, 1622~1636, 2000)(Zalutsky, M. R & Vaidyanathan, G. *Curr. Pharm. Des.* 6, 1433~1455, 2000) (Goldenburg, D. M. in Clinical Uses of Antibodies (eds Baum, R. P., et al.)1~13(Kluwer academic, The Netherlands, 1991)(Lode, H. N. & Reisfield, R. A *Immunol. Res.* 21, 279~288, 2000) (Penichet, M. L & Morrison, S. L. *J. Immunol. Methods* 248, 91~101, 2001)(Lasic, D. D & Papahadjopoulos, D. *Science* 267, 1275~1276, 1995) (Park. J. W., et al., *Proc. Natl. Acad. Sci. USA* 92, 1327~1331) (Niculescu-Davaz, I., et al., *Anticancer Drug Des.* 14, 517~538, 1999) (SToldt, H. S., et al., Eur. J. Cancer 33, 186~192, 1997))]

In another mode, the dimeric form of chimeric recombinant binding domain-functional group fusion([B-F fusion]$_2$) with double binding valency is indicated as a formula below.

[Antibody binding domain-Ext-F]$_2$ (II)

The antibody binding domain in formula(II) is antibody or amino acid sequence comprising adhesive fragment of antibody.

Ext is extension peptide chain(extension sequence) extended from binding domain(B) to functional group(F) to fuse them, and disulfide-bond-bridge is formed between the monomers by the oxidation of two uncoupled Cys on the extension peptide chain(Ext) to produce dimer, or said extension peptide chain comprises peptide linker(L) from the last uncoupled Cys to the end of extension peptide chain or said peptide linker is an affinity domain(AD) containing peptide linker(LAD) which has homomeric self affinity or heteromeric affinity leading to the formation of homomeric multimer or heteromeric multimer domain, or said peptide linker (L) is flexible amino acid(FA) sequence peptide linker(LFA) which has non-bulky amino acids like Glycine(G) or Alanine (A) or Serine(S) or Glutamine(Q) or Glutamic acid(E) or Asparagine(N), Aspartic acid(D) or said peptide linker having affinity domain(AD) with homomeric self affinity or heteromeric affinity comprising multimer domains and having non-bulky amino acids like Glycine(G) or Alanine(A) or Serine(S) or Glutamine(Q) or Glutamic acid(E) or Asparagine(N), Aspartic acid(D) to be a flexible amino acid sequence peptide linker with affinity domain(LADFA) (SEQ ID NO: 14) so to be a sequence as [B-Ext or Ext(L) or Ext(LAD) or Ext(LFA) or Ext(LADFA) (SEQ ID NO: 14)-F] in its monomer form;

F is for physiological functional group like enzyme, protein with physiological (e.g. toxic) function, organisms like viruses, compounds, drug compounds for treatment, liposome, biosensor, pro-drug and more.

In another mode, the dimeric form of chimeric recombinant binding domain-functional group fusion([B-F fusion]$_2$) with double binding valency is indicated as a formula below

[Fab-Ext-F]$_2$ (III)

Fab in the said formula(III) is Fab fragment of antibody.

Ext is extension peptide chain (extension sequence) extended from binding domain(B) to functional group(F) to fuse them, and disulfide-bond-bridge is formed between the monomers by the oxidation of two uncoupled Cys on the extension peptide chain(Ext) to produce dimer, or said extension peptide chain comprises peptide linker(L) from the last uncoupled Cys to the end of extension peptide chain or said peptide linker is an affinity domain(AD) containing peptide linker(LAD) which has homomeric self affinity or heteromeric affinity leading to the formation of homomeric multimer or heteromeric multimer domain, or said peptide linker (L) is flexible amino acid (FA) sequence peptide linker(LFA) which has non-bulky amino acids like Glycine(G) or Alanine (A) or Serine(S) or Glutamine(Q) or Glutamic acid(E) or Asparagine(N), Aspartic acid(D) or said peptide linker having affinity domain(AD) with homomeric self affinity or heteromeric affinity comprising multimer domains and having non-bulky amino acids like Glycine(G) or Alanine(A) or Serine(S) or Glutamine(Q) or Glutamic acid(E) or Asparagine(N), Aspartic acid(D) to be a flexible amino acid sequence peptide linker with affinity domain(LADFA) (SEQ ID NO: 14) so to be a sequence as [B-Ext or Ext(L) or Ext(LAD) or Ext(LFA) or Ext(LADFA) (SEQ ID NO: 14)-F] in its monomer form;

F is for physiological functional group like enzyme, protein with physiological(e.g. toxic) function, organisms like viruses, compounds, drug compounds for treatment, liposome, biosensor, pro-drug and more.

In another mode, the dimeric form of chimeric recombinant binding domain-functional group fusion([B-F fusion]$_2$) with double binding valency is indicated as a formula below $V_H$ is variable region on heavy chain of monoclonal antibody;

$C_H$ is constant region on heavy chain of monoclonal antibody;

Ext is extension peptide chain(extension sequence) extended from binding domain(B) to functional group(F) to fuse them, and disulfide-bond-bridge is formed between the monomers by the oxidation of two uncoupled Cys on the extension peptide chain(Ext) to produce dimer, or said extension peptide chain comprises peptide linker(L) from the last uncoupled Cys to the end of extension peptide chain or said peptide linker is an affinity domain(AD) containing peptide linker(LAD) which has homomeric self affinity or heteromeric affinity leading to the formation of homomeric multimer or heteromeric multimer domain, or said peptide linker (L) is flexible amino acid (FA) sequence peptide linker(LFA) which has non-bulky amino acids like Glycine(G) or Alanine (A) or Serine(S) or Glutamine(Q) or Glutamic acid(E) or Asparagine(N), Aspartic acid(D) or said peptide linker having affinity domain(AD) with homomeric self affinity or heteromeric affinity comprising multimer domains and having non-bulky amino acids like Glycine(G) or Alanine(A) or Serine(S) or Glutamine(Q) or Glutamic acid(E) or Asparagine(N), Aspartic acid(D) to be a flexible amino acid sequence peptide linker with affinity domain(LADFA) (SEQ ID NO: 14) so to be a sequence as [B-Ext or Ext(L) or Ext(LAD) or Ext(LFA) or Ext(LADFA) (SEQ ID NO: 14)-F] in its monomer form;

F is for physiological functional group like enzyme, protein with physiological(e.g. toxic) function, organisms like

[Reference formula 1]

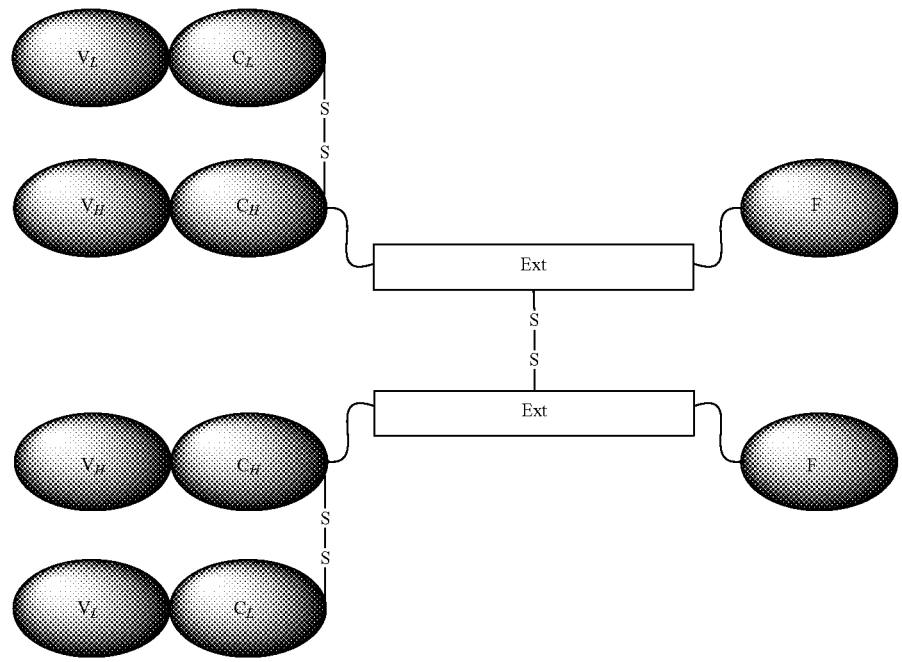

According to the formula above, $V_L$ is variable region on light chain of monoclonal antibody;

$C_L$ is constant region on light chain of monoclonal antibody;

viruses, compounds, drug compounds for treatment, liposome, biosensor, pro-drug and more.

More specifically, the dimeric form of chimeric recombinant binding domain-functional group fusion([B-F fusion]$_2$) with double binding valency is indicated as a formula below

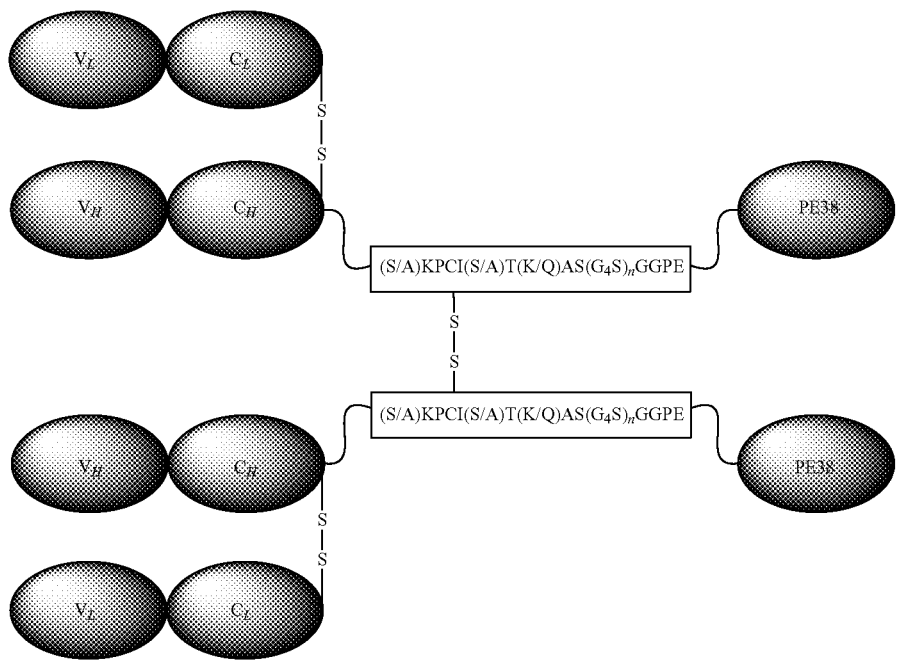

[Reference formula 2]

According to the formula above, $V_L$ is variable region on light chain of monoclonal antibody;

$C_L$ is constant region on light chain of monoclonal antibody;

$V_H$ is variable region on heavy chain of monoclonal antibody;

$C_H$ is constant region on heavy chain of monoclonal antibody;

A is Alanine;
C is Cysteine;
E is Glutamic acid;
G is Glycine;
I is Isoleucine;
K is Lysine;
P is Proline;
Q is Glutamine;
S is Serine;
T is Threonine;
n is 1 or 2 or 3;

PE38 is 38 kDa exotoxin derivative of *Pseudomonas aeruginosa* which has been truncated of amino acid sequences of domain I and II that are not required for cytotoxicity.

The inventors used the previous recombinant binding domain(B)-functional domain(F) fusion model to invent [B3 (Fab)-(S/A)KPCI(S/A)T(K/Q)AS(G4S)nGGPE(SEQ ID NO: 15)-toxin-functional group]$_2$ having twice the adhesion valency and using monoclonal antibody B3 as a model binding domain. Antibody-toxin functional group fusion made in the meantime was monovalent but the invented dimeric antibody-toxin functional group fusion is divalent so it will display much more cytotoxicity towards cultured cancer cells. This molecule is produced by modifying Fd-CKPSISTKASGGPE(SEQ ID NO: 16)-toxin functional group chain among Fd-CKPSISTKASGGPE(SEQ ID NO: 16)-toxin functional group chain and L chain which are used in composing monovalent Fab-CKPSISTKASGGPE(SEQ ID NO: 16)-toxin functional group formed monomer. The modified chain was made by changing the position of uncoupled Cysteine with Serine coming after Cysteine. (S/A) means Serine or Alanine and (K/Q) means Lysine or Glutamine. (G4S)n peptide chain is (GGGGS) (SEQ ID NO: 17) or (GGGGSGGGGS) (SEQ ID NO: 18) or (GGGGSGGGGSGGGGS) (SEQ ID NO: 19) and it's in the middle of the KASGGPE (SEQ ID NO: 30) to have Fd-(S/A)KPCI(S/A)T(K/Q)AS(G4S)nGGPE(SEQ ID NO: 15)-PE38 structure and mixing and refolding this with L chain makes an activated molecule. The divalent dimer [Fab-(S/A)KPCI(S/A)T(K/Q)AS(G4S)nGGPE(SEQ ID NO: 15)-PE38]$_2$ is formed by disulfide-bond-bridge connecting two Fab-(S/A)KPCI(S/A)T(K/Q)AS(G4S)nGGPE(SEQ ID NO: 15)-PE38 by the fourth amino acid, uncoupled Cysteine. This molecule keeps the stability of the Fab-toxin functional group structure and targeting efficiency too.

The invention dimer of chimeric recombinant binding domain-functional group fusion([B-F fusion]$_2$) by using disulfide-bond-bridge connecting the two of a monomer of chimeric recombinant binding domain-functional group fusion (B-F fusion) has extension peptide chain(extension amino acid sequence, Ext) extended from binding domain(B) to functional group(F) to fuse them, and disulfide-bond-bridge is formed between the monomers by two uncoupled oxidized Cys on the extension peptide chain(Ext) to produce dimer, or said extension peptide chain comprises peptide linker(L) from the last uncoupled Cys to the end of extension peptide chain or said peptide linker is an affinity domain containing peptide linker(LAD) which has homomeric self affinity or heteromeric affinity comprising homomeric multimer or heteromeric multimer domain, affinity domain(AD) or said peptide linker(L) is flexible amino acid (FA) sequence peptide linker(LFA) which has non-bulky amino acids like Glycine (G) or Alanine(A) or Serine(S) or Glutamine(Q) or Glutamic acid(E) or Asparagine(N), Aspartic acid(D) or said peptide linker having affinity domain(AD) with homomeric self affinity or heteromeric affinity comprising multimer domains and having non-bulky amino acids like Glycine(G) or Alanine(A) or Serine(S) or Glutamine(Q) or Glutamic acid(E) or Asparagine(N), Aspartic acid(D) to be a flexible amino acid sequence peptide linker with affinity domain(LADFA) (SEQ ID NO: 14) so to be a sequence as [B-Ext or Ext(L) or Ext(LAD) or Ext(LFA) or Ext(LADFA) (SEQ ID NO: 14)-F] in its monomer form. And the dimer has decreased three-dimensional hindrance between the two functional groups while being produced and they are produced through mixing and refolding the polypeptide obtained from the host cells containing recombinant plasmid with the Ext sequences for dimerization.

In the following, the double binding valency dimer of chimeric recombinant binding domain(B)-functional domain(F) fusion will be described in details and through this description the manufacturers concerned will be able to produce any related dimer of chimeric recombinant binding domain(B)-functional domain(F) fusion.

In another mode, this invention offers polypeptides for producing dimeric chimeric recombinant binding domain-functional group fusion([B-F fusion]$_2$) and it is indicated as a formula below.

mucinous cancer like colon carcinoma, stomach cancer, ovarian cancer, breast cancer and lung cancer but also various epidermoid carcinomas.

*Pseudomonas aeruginosa* exotoxin PE-derived PE38 was used as toxin functional group in this invention. PE is composed of three structural domains. Domain 1 at the amino terminal binds with the cell, domain 2 enables the transport of the protein into the cell, domain 3 is at the carboxy terminal having cytotoxic enzymatic activity. Truncating needless amino acids not used for cytotoxic enzymatic activity from domain 1, 2 produced the 38 kDa PE38.

The B3 monoclonal antibody is dimer form in nature as [Fab-Fc]$_2$ because of the three Cysteine in the hinge. The inventors used 1 uncoupled Cysteine, or 3 uncoupled Cysteines although 3 uncoupled Cysteines have much higher risk of mixing disulfide bonding while refolding and showed that using multiple numbers of uncoupled Cysteine can also produce physiologically active dimers. Manufacturers concerned know the dimer produced with multiple disulfide bonds using multiple uncoupled Cysteins will be highly thermodynamically stable.

The extension peptide chain(Ext) (S/A)KPCI(S/A)T(K/Q)AS(G4S)n GGPE (SEQ ID NO: 15) has a flexible peptide linker(LFA) I(S/A)T(K/Q) AS(G4S)nGGPE (SEQ ID NO:

[Reference formula 3]

(S/A)KPCI(S/A)T(K/Q)AS(G$_4$S)$_n$GGPE (SEQ ID NO: 15)

In another mode, this invention offers recombinant plasmid that expresses said polypeptide.

In another mode, this invention offers methods to produce said divalent recombinant antibody-toxin functional group fusion by culturing host cells with recombinant plasmid expressing said polypeptide gene and other host cells with plasmid expressing light chain which includes V$_L$ and C$_L$ and joining them together and refolding them.

The divalent recombinant antibody-toxin functional group fusion specifically binding its antibody to cancer cell and connecting the toxin functional group is anti-cancer therapeutic agent and it kills the cancer cells without damaging other normal cells.

B3(Fab)-PE38 is produced from the fusion of Fab of monoclonal antibody B3 and PE38 which is truncated type of *Pseudomonas aeruginosa* exotoxin and it doesn't have uncoupled Cysteine which means it can only be a monomer. The [B3(Fab)-Ext-PE38]$_2$ which belongs to divalent chimeric recombinant binding domain(B)-functional domain(F) fusion is derived from B3(Fab)-PE38 and the Fab of antibody is connected to functional group with (S/A)KPCI(S/A)T(K/Q)AS(G4S)nGGPE (SEQ ID NO: 15).

The monoclonal antibody B3 used in this invention binds directly to LeY type carbohydrate antigen found not only in 20) including GASQEND (SEQ ID NO: 21). Also the thiol group of the uncoupled Cysteine on Ext enables disulfide bonding to form divalent chimeric recombinant antibody-toxin functional group fusion[B3(Fab)-Ext-PE38]$_2$ from two polypeptide[B3(Fab)-Ext-PE38].

The peptide linker following the uncoupled Cysteine in the extension peptide chain reduces the three-dimensional hindrance between the two toxin functional group PE38 helping dimerization. Also under same condition, when the number n increases from 1 to 3, the production yield increased. This means while the dimer has 50 kDa Fab sequence and 38 kDa PE38, until the number of GASQEND (SEQ ID NO: 21) which is in flexible peptide linker(LFA) increases to 21, the dimerization will increase.

The inventors realized that dimer is not only formed by specific numbers and location of the uncoupled Cysteine and specific linker(L) amino acid sequence but, multiple numbers and certain range of locations of Cys, certain range of amino acid sequence of linker(L) can make dimers too. The manufacturers concerned can easily predict that if the size of the binding domain(B) differs and the functional domain(F) also differs, the trend will differ too. So to speak, in case of small sized binding domain and functional domain fusion, dimerization will occur even under peptide linker with only 1 amino acid and if there are too many GASQEND (SEQ ID NO: 21) of the flexible peptide chain(LFA) in the extension peptide chain, it will rather disturb refolding of the binding domain and functional domain because of the easy mutual interference and result in decrease of the active molecule yield. Therefore, it is important to find out the range of the position of the uncoupled Cys and the range of the length of the amino acid sequence(the length of L,LFA or the length between AD and F in LAD, LADFA (SEQ ID NO: 14) needed in the peptide linker of extension peptide chain that makes dimerization possible without disulfide bond scrambling. Naturally, the big sized binding domain(B) and functional domain (F) fusion will need more than 1 flexible amino acid of GASQEND (SEQ ID NO: 21) for dimerization and longer length can be predicted easily among manufacturers concerned.

The divalent chimeric recombinant antibody-toxin functional group fusion dimer[B3(Fab)-Ext-PE38]$_2$ is produced by applying fusion of the antibody gene and toxin functional group gene together and expressing it in *E. coli*. (Reference: Allured et al., 1986; Brinkmann et al., 1992; Pai et al., 1991: Roscoe et al., 1997)

In detail, recombinant vector expressing polypeptide B3(Fd)-Ext-PE38 is produced in this invention. The polypeptide B3(Fd)-Ext-PE38 has a polypeptide chain (S/A)KPCI(S/A)T(K/Q)AS(G4S)nGGPE (SEQ ID NO: 15) between Fd and PE38. Therefore, in this case, flexible amino acid peptide linker(LFA) of extension peptide chain(Ext) is "I(S/A)T(K/Q)AS(G4S)nGGPE (SEQ ID NO:20)" and the constitution of B3(Fd)-Ext-PE38 is same as B3(VH)-B3(CH1)-(S/A)KPCI(S/A)T(K/Q)AS(G4S)nGGPE(SEQ ID NO: 15)-PE38. The uncoupled Cysteine on extension peptide chain forms disulfide bond-bridge between two Fab-Ext-PE38. The decrease of three dimensional hindrance between two PE38 enables dimerization of B3(Fab)-Ext-PE38 easily by flexible amino acid following uncoupled Cysteine on the extension chain.

The extension peptide chain is for amicable, independent refolding without disturbances between antibody and PE toxin functional group in producing recombinant protein antibody-toxin functional group fusion.

The Proline(P) on the end of extension peptide chain (S/A)KPCI(S/A)T(K/Q)AS(G4S)nGGPE (SEQ ID NO: 15) cuts off the continuation of refolding motifs to prevent each refolding motif from interfering neighbor refolding domain during the process of refolding of antibody and toxin functional group.

The divalent recombinant antibody-toxin functional group fusion is produced by culturing the host cells having recombinant vectors cloned with B3(Fd)-Ext-PE38 and light chain of B3 respectively to gain polypeptides of these and then mixing these to refold. The cloned gene is expressed and gained as inclusion body in *E. coli*. Polypeptide is refolded and the active products are separated.

The method for refolding can follow well-known procedures and some references describe the methods[Reference: Buchner, J., et al., *Anal. Biochem.* 205(2), 26~70 (1992), Buchner, J., et al., *Biotechnonlogy,* 9:15~162 (1991)]

Typical ID50 value of divalent recombinant antibody-toxin functional group fusion$[B3(Fab)\text{-}Ext\text{-}PE38]_2$ was measured on A431 adenosquamous carcinoma cell line at 4 ng/ml, CRL1739 stomach cancer cell line at 1 ng/ml, MCF-7 breast cancer cell line at 5 ng/ml. The divalent recombinant antibody-toxin functional group fusion$[B3(Fab)\text{-}Ext\text{-}PE38]_2$ showed nearly 12 times higher cytotoxicity than the monovalent antibody-toxin functional group B3(scFv)-PE40.

This invention dimer of chimeric recombinant binding domain(B)-functional group(F) fusion offers pharmaceutical drug formulation which includes excipients like carriers or diluents. Pharmaceutical drug formulation containing dimer of chimeric recombinant binding domain(B)-functional group(F) fusion can be produced by commonly used method and prescribed in an appropriate way.

Dimer of chimeric recombinant binding domain(B)-functional group(F) fusion can be used as a drug alone or with radiotherapy, chemotherapy(cell growth inhibitor, cytotoxic agents, antibiotic agents, alkylating agents, anti-metabolic agents, hormones, immunological agents, interferon agents, cycloxygenase inhibitor(e.g. COX-2 inhibitor), metalomatrixprotease inhibitor, telomerase inhibitor, tyrosine kinase inhibitor, anti-growth factor receptor agents, anti-HER agents, anti-EGFR agents, anti-angiogenesis agents, farnesyl transferase inhibitor, ras-raf signal transduction inhibitor, cell cycle inhibitor, cdk inhibitors, tubulin binders, topoisomerase I inhibitor, topoisomerase II inhibitor etc.) and others.

For example, dimer of chimeric recombinant binding domain(B)-functional group(F) fusion can be prescribed with liposomal agents containing more than one chemical agents (e.g. taxane, taxane-derivatives, capsulated taxane, CPT-11, camptothesin-derivatives, anthracycline glycoside for example, idarubicin, epirubicin, etoposide, navelbine, vinblastine, carboplatine, cisplatin, estramustine, celecoxib, Sugen SU-5416, Sugen SU-6668, Herceptin etc.) used in chemotherapy.

If the mixed formulation of dimer of chimeric recombinant binding domain(B)-functional group(F) fusion and chemicals is not appropriate, they can be used on sequential order.

Dimer of chimeric recombinant binding domain(B)-functional group(F) fusion is administered through common routes and the dosage is decided according to the age, weight, condition and medication route of the drug. For example, the suitable dosage for dimer of chimeric recombinant binding domain(B)-functional group(F) fusion can be 10~2000 mg, once to 5 times a day. Dimer of chimeric recombinant binding domain(B)-functional group(F) fusion can be medicated in various forms like oral delivery system as tablets, capsules, sugar-coated tablets, film-coated tablet, solution, suspension or suppositories systems or parenteral methods as injection into muscles, vein and/or central canal and/or spinal cord.

Solid drug for oral application contains active components with diluents (e.g. lactose, dextrose, sucrose, cellulose, corn starch, potato starch), lubricant (e.g. silica, talc, stearate, magnesium, calcium stearate and/or polyethylene glycol), bonding agent(e.g. starch, Arabic gum, gelatin methylcellulose, carboxymethyl cellulose, poly(N-vinyl pyrrolidone), disintegrants(e.g. starch, alginate, sodium starch, glycolate), formal mixture, dyes, sweetenings, wetting agents(e.g. lecithin, polysorbate, lauryl sulfate) and pharmaceutically inactive agents commonly used in pharmaceutics. Using common methods, for example mixing, granulation, tablet formation, sugar or film coating can produce these drugs.

Liquid dispersion for oral application is for example, syrup, emulsion, and suspension. Emulsion and suspension can contain carriers and there are natural gum, agar, sodium alginate, pectin, methylcellulose, carboxymethylcellulose and polyvinyl alcohol, which are used. Suspension or solution for injection into the muscle may contain active components with pharmaceutically allowed carriers like distilled water, olive oil, ethyl oleiate, glycol(e.g. propylene glycol) and appropriate dosage of lidocaine hydrochloride if needed. Carriers used for injections or infusions are distilled water and preferably they are sterilized, hydrogenous, isotonic solution or they may contain propylene glycol as a carrier. Suppositories use carriers like cocoa butter, polyethylene glycol, polyoxyethylene sorbitan, fatty acid ester surface-active agent, lecithin.

The following will describe this invention more minutely in detail using examples but it does not limit the boundary of the claim.

ADVANTAGEOUS EFFECTS

The invention dimer of chimeric recombinant binding domain(B)-functional group(F) fusion formed via disulfide-bond-bridge between monomeric chimeric recombinant binding domain(B)-functional group(F) fusion is valuable for the pharmaco-medical industry since it is the first dimer formed by covalent disulfide bond to have twice the binding valency and high structural stability and has excellent functional efficiency towards its targets and has high production yield by containing said flexible peptide chain (LFA).

BEST MODE FOR CARRYING OUT THE INVENTION

Example 1

Production of Dimers which have Ext (4CLFA5X=4CL15FA11, 4CL20FA16, 4CL25FA21, AQ4CL20FA16) with Fixed Uncoupled Cysteine at Fourth Amino Acid Position and Additional Increase of Five Flexible Amino Acids in its Flexible Linker Sequence (LFA)

[B3(Fab)-Ext(4CLFA5X=4CL15FA11, 4CL20FA16, 4CL25FA21, AQ4CL20FA16)-toxin]$_2$ has uncoupled Cysteine at fixed $4^{th}$ position and has an extension peptide chain for the formation of the dimer with five amino acid additional increase in flexible amino acids linker(LFA).

On this example, the uncoupled Cysteine in the fourth location from the Fab of B3 antibody is fixed to induce dimer formation and with the uncoupled Cysteine, different numbers of flexible amino acids on extension peptide chain were put in between Fd and toxin domain to compare production yield fluctuation caused by three-dimensional steric space difference. 11, 16, 21 flexible amino acids which make the length of Linker to be 15, 20, 25 were used on this test. Alanine was used instead of Serine on the position of cysteine of natural antibody hinge sequence. The OH group of two serines takes more three-dimensional space than the natural cystine disulfide bond in dimer form. The reduced number of cysteine in extension sequence that is derived from antibody hinge sequence prevents scrambling of disulfide bonds.

The presented four types of [B3(Fab)-Ext(4CLFA5X)-PE38]$_2$ molecules had same disulfide bond formed between uncoupled Cysteines fixed at 4th position on Ext of both sides of monomers to make its interference on the formation of three dimensional structure and intermixing of disulfide bonds equal. And the amino acids following the uncoupled Cysteines were left the same except that the numbers of flexible amino acids were increased to see the effect of the sterical tolerance given by the increased length of the LFA. Adding flexible amino acids led to 12~17 times higher production yield of these molecules than molecules produced before.

Therefore, this example compared with the accumulated previous results shows the disulfide bond between uncoupled Cys on Ext of the two fusion monomer of large molecular weight 50 kD B3 antibody and 38 kD Fab domain can be formed to produce the dimer on any position in certain range of the position of Ext and not on a specific point of Ext without interfering the large neighboring domains. So, this example shows definitely that the position of the uncoupled Cysteine on Ext can be chosen generally in certain range and the increase of the number of flexible amino acids in the range of 11~21, which make the length of LFA to be 15~25, helps the disulfide bond formation for the dimerization of two monomers.

(Apparatus and Methods)

E. coli BL21(DE3) was used for protein expression. Cancer cell lines used in cytotoxicity test were A431, CRL1739, MCF7, KB3-1. pMH21, 22, 23, pMHS22 is plasmid coding B3(Fd)-Ext(4CL15FA11, 4CL20FA16, 4CL25FA21, AQ4CL20FA16)-PE38 and plasmid pMC74, pCE2 is used for construction of the plasmids and plasmid which offers the light chain that matches with pMH21, 22, 23, pMHS22 is pMCH75. The description of the plasmid, cell line and primer used in the experiment is on table 1, 2 and 3 respectively.

TABLE 1

| Plasmid Name | Coding Polypeptide Chain |
|---|---|
| pMC74 | B3(Fd)-SKPSISTKASGGPE (SEQ ID NO: 42)-PE38REDLK (SEQ ID NO: 56) |
| pCE2 | B3(Fd)-SKPCISTKASGGPE (SEQ ID NO: 46)-PE38REDLK (SEQ ID NO: 56) |
| pMCH75 | H6-B3(L) |
| pMH21 | B3(Fd)-Ext(4CL15FA11)-PE38 = B3(Fd)-SKPCISTKAS**(G4S)1**GGPE (SEQ ID NO: 47)-PE38REDLK (SEQ ID NO: 56) |
| pMH22 | B3(Fd)-Ext(4CL20FA16)-PE38 = B3(Fd)-SKPCISTKAS**(G4S)2**GGPE (SEQ ID NO: 48)-PE38REDLK (SEQ ID NO: 56) |
| pMH23 | B3(Fd)-Ext(4CL25FA21)-PE38 = B3(Fd)-SKPCISTKAS**(G4S)3**GGPE (SEQ ID NO: 49)-PE38REDLK |
| pMHS22 | B3(Fd)-Ext(AQ4CL20FA16)-PE38 = B3(Fd)-AKPCIATQAS(G4S)2GGPE (SEQ ID NO: 50)-PE38REDLK (SEQ ID NO: 56) |

TABLE 2

| cell line | cell type | B3 antigen expression | Used Media |
|---|---|---|---|
| A431 | Epidermoid | +++ | RPMI 1640, 10% FBS |
| CRL-1739 | Gastric | + | RPMI 1640, 10% FBS |
| MCR-7 | Breast adenocarcinoma | +++ | RPMI 1640, 5% FBS |
| KB3-1 | Epidermoid cervix | − | DMEM, 5% FBS |

TABLE 3

| Name of the primer | Sequence 5'-3' |
|---|---|
| Primer MH-1 (SEQ ID NO: 23) | TAA TAC GAC TCA CTA TAG GGA GA |
| Primer MH-2 (SEQ ID NO: 24) | AGA TCC GCC ACC ACC AGA AGC TTT TGT ACT TAT GCT |
| Primer MH-3 (SEQ ID NO: 25) | CCA GAT CCG CCA CCA CCA CTT CCC CCT CCC CCG GAA GCT TTT GTA CTT ATG CTA GGC TTA CT |
| Primer MH-4 (SEQ ID NO: 26) | TGC TGG TGG CGG ATC TGG AGG TCC CGA GGG CGG CAAG C |
| Primer MH-5 (SEQ ID NO: 27) | TGG TGG TGG CGG ATC TGG AGG TGG CGG AAG CGG AGG TCC CGA GGG CGG CAG C |
| Primer MH-6 (SEQ ID NO: 28) | GCC GCG GGT GCT GAA GCT GAC GTC GCC GCC GTC |

TABLE 3-continued

| Name of the primer | Sequence 5'-3' |
|---|---|
| Primer MH-7 (SEQ ID NO: 29) | GGG AAT TCA TTA AGC TTG TGT AGC TAT GCA AGG CTT AGC ACC ACA |

(Used Reagents)

Tryptone, yeast extract, agar(Difco co.), minerals(Junsei co.) was used in culture medium for bacterial culture. Ampicilin (Sigma chemical co.) 200 μg/mL was used for bacterial selection as final concentration added to the medium.

Nde I, HindIII, Sal I used for plasmid construction was products from NEB co. Ex Taq polymerase for PCR amplification and T4 DNA ligase for ligation were products from TaKaRa co. Coomassie Plus Protein Assay Reagent and BSA standard protein from Pierce co. were used for protein analysis. Buffers needed for dialysis, denaturation, refolding, protein purification were from Sigma. Isopropyl-β-thiogalactopyranoside(IPTG) for protein induction and urea for dialysis were products from Duchefa co. Q-sepharose(Pharmacia Biotech) and Source Q(Pharmacia Biotech) were used as column for purification of protein which is anion exchange chromatography and Superdex-200(Pharmacia Biotech) was used for size exclusion chromatography.

(Plasmid Construction)

Construction of plasmid expressing B3(Fd)-Ext-PE38 recombinant protein was made by splicing PCR using pMC74(Fd-PE38) as a template to insert $(G4S)_n$ inside of the KASGGPE (SEQ ID NO: 30) in existing Fd-PE38. This $(G4S)_n$-inserted coding sequence was exchanged with appropriate part of plasmid pCE2(vector which expresses B3(Fd)-SKPCISTKASGGPE (SEQ ID NO: 46)-PE38) using Hind III, EcoR 1.

Figure 2:
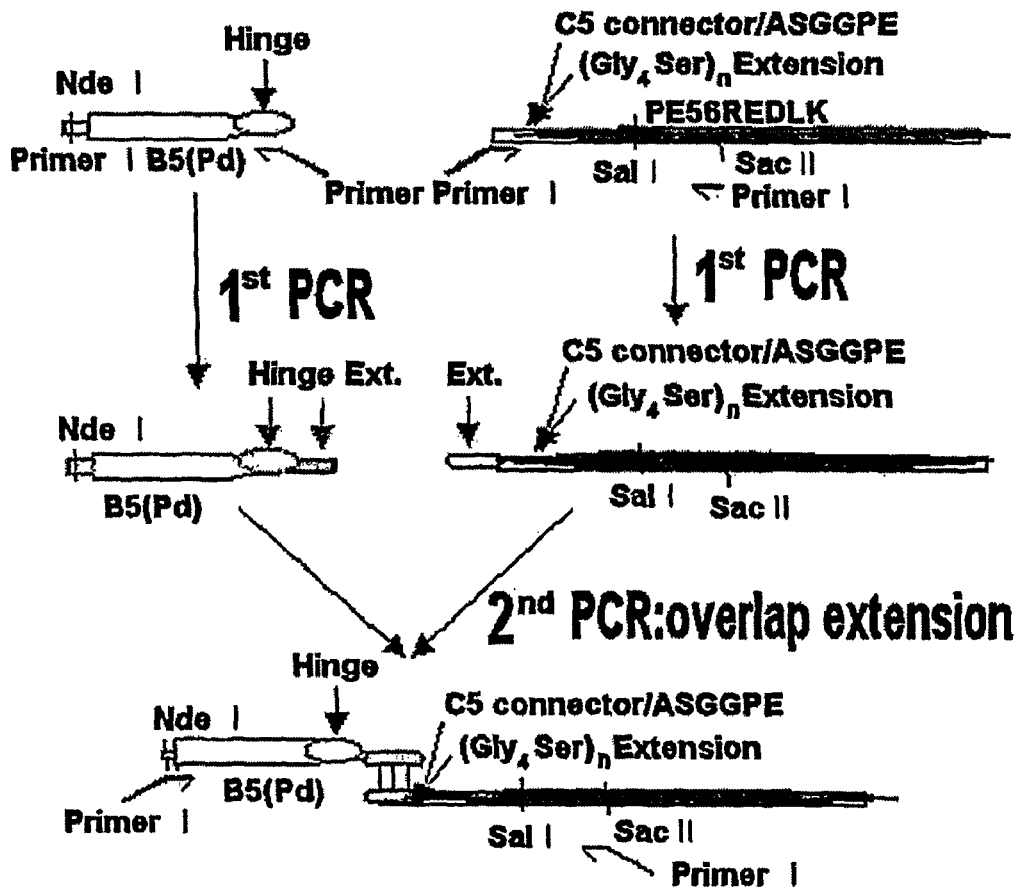
FIG. 2 shows the construction procedure of pMH21, 22, 23, pMHS22 by PCR.
Figure 3:
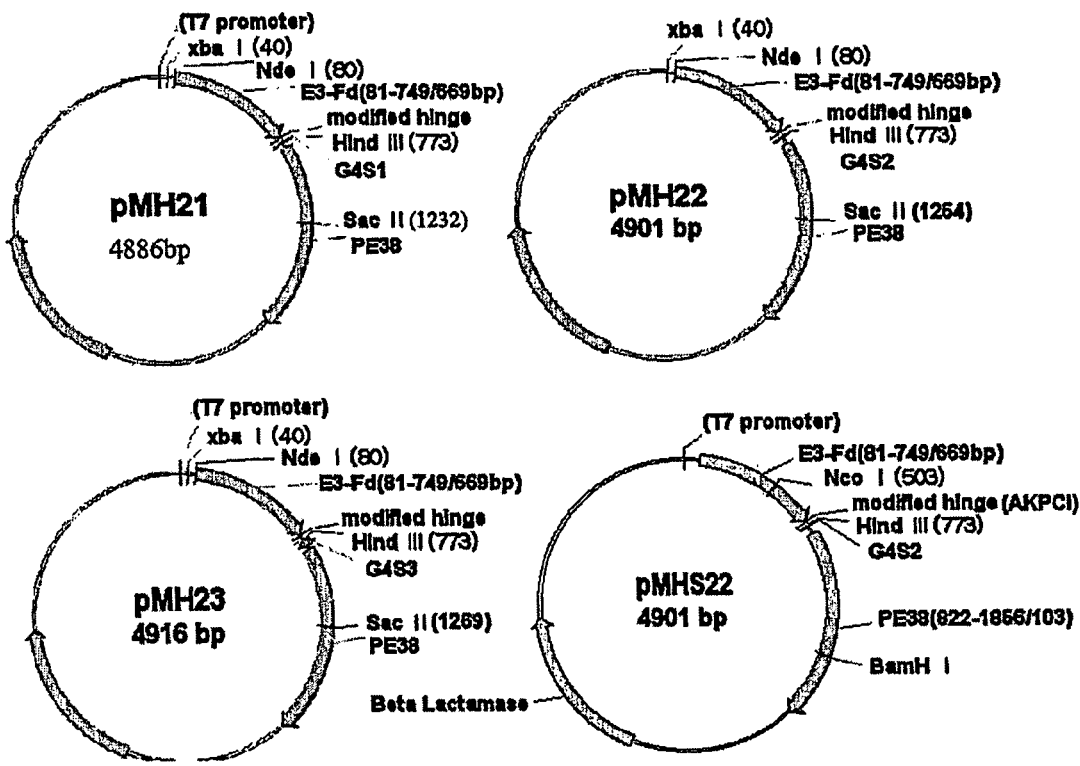
FIG. 3 shows the plasmid map of pMH21, 22, 23, pMHS22.

Plasmid pMHS22(B3(Fd)-Ext(AQ4CL20FA16)-PE38) which has exchanged the Cysteine on the natural hinge sequence to Alanine was constructed by PCR using pMH22 (B3(Fd)-Ext(4CL20FA16)-PE38) as a template to get a fragment and then exchanged with appropriate part of pMH22.

pMH21, 22, 23 which expresses [B3(Fd)-Ext (4CL15FA11, 4CL20FA16, 4CL25FA21)-PE38]$_2$ and pMHS22 which expresses B3(Fd)-Ext(AQ4CL20FA16)-PE28 are shown in FIG. 1. FIG. 2 shows the construction procedure for plasmid.

(Protein Expression and Isolation of Inclusion Body)

Proteins are expressed from plasmid pMH21, 22, 23, pMHS22, pMCH75 in *E. coli* BL21(DE3) (Studier et al., 1986). Bacteria was cultured at 37° C. in superbroth(Tryptone 10 g, yeast extract 5 g, sodium chloride 10 g) to which was added 0.05% MgSO$_4$, 2% glucose, ampicilin 150 μg/mL per liter. IPTG induction was at OD$_{600}$ 1.5~2.0 and it was cultured for 3 more hours until OD$_{600}$ 3. Cells were harvested at 3500 rpm, 4° C. for 20 minutes and collected in pellet. They were resuspended in 200 mL ice-chilled sucrose solution and they were collected again at 8,000 g, 4° C. for 20 minute. The cell were resuspended again in ice-chilled water 200 mL to give osmotic shock and centrifuged at 15,000 g, 4° C. for 20 minutes to gain pellets. This pellet was resuspended in TE buffer (50 mM Tris-Cl pH8.0, 20 mM EDTA, pH8.0) and treated with lysozyme to remove peptidoglycan layer. The highly concentrated salt 5M NaCl and 25% Triton X-100 was added and mixed evenly with tissuemizer, and incubated for 1 hour and centrifuged at 25,000 g for 30 minutes to gain inclusion body pellet. To remove periplasmic protein 25% Triton X-100 was added and mixed evenly with tissuemizer, and centrifuged at 25000 g for 30 minutes and Triton X-100 treatment was repeated once again. The pellet was washed with 4M urea buffer(4M urea, 0.1M Tris-Cl). Residual Triton X-100 and urea was removed by resuspending and washing the pellet in TE buffer(50 mM Tris-Cl pH7.4, 20 mM EDTA pH7.4) and centrifuging at 25,000 g, RT for 30 minutes for 3 times. The whole protein quantity of inclusion body gained was analyzed using Coomassie Plus Protein Assay reagent and the antibody-toxin protein quantity was analyzed using Tina 2.0 program. These were stored in –70° C. freezer before the refolding procedure.

(Refolding Process and Isolation of Protein)

Each inclusion body was dissolved in solubilizing buffer solution(6M Guanidine-HCl, 0.1M Tris-Cl, pH8.0, 2 mM EDTA pH8.0) and the 5 mL solution of the 1:1 molar ratio mixture of B3(Fd)-Ext-PE38 and B3(L) was prepared to be 40 mg in 5 mL final volume with solubilizing buffer(use the dissolving buffer solution mixing with 40 mg antibody-toxin protein and final volume to be 5 mL to make.). 0.06 mM Dithiotreitol(DTT) was mixed into this for reduction procedure. Refolding procedure was taken in 500 mL refolding buffer solution and started with rapidly diluting 5 mL of above inclusion body mixture in solubilizing buffer solution, which is a 1:100 dilution ratio. The sample was incubated at 10° C. for 48 hours. The quantity of antibody-toxin protein used in this procedure was 80 mg and 1 L for refolding buffer solution. The refolded protein was taken into dialysis process and isolated through Q-sepharose, source Q, Superdex200 column chromatography(Choe et al., 1994).

(Analysis of Cytotoxicity Effect Against Cells)

The cytotoxicity effect of isolated protein[B3(Fab)-Ext-PE38]$_2$ was analyzed as described below. Antigen LeY expressing cell lines which are A431, CRL1739, MCF-7 and non-expressing cell line which is KB3-1 were diluted to be 1×10$^5$ cells/mL, aliquoted into 96-well plate in 180 μl/each well and cultured in a CO$_2$ incubator for 24 hours at 37° C. Purified antibody-toxins are serially diluted to be 10000 ng/mL, 1000 ng/mL, 100 ng/mL, 10 ng/mL, 1 ng/mL, 0.1 ng/mL, 0.01 ng/mL in PBS with 0.2% BSA. The each of diluted antibody-toxin are added to 3 wells in 20 μl volume each well and incubated for 24 hours. 1 μCi of [$^3$H]-leucine (NEN) was put into each well, cultured for 14 hours. The cells were put in to –70° C. freezer and put them out to melt to detached the cells from the plate. The quantity of [$^3$H] incorporated into living cell was analyzed using 1450 Microbeta TriLux Liquid Scintillation Counter(Wallac E G & Co.). The cells are shown in table 2.

(Construction of Expression Vectors and Isolation of Inclusion Body.)

The nucleotide sequence of pMH21, pMH22, and pMH23, pMHS22 made from PCR was confirmed by nucleotide sequence analysis.

The amounts of proteins in inclusion body form produced by T7 polymerase system was 100~120 mg/L culture for Fd-Ext-toxin, and 80~100 mg/L culture for light chain. To isolate antibody-toxin protein from whole protein, osmotic pressure was firstly given to the cells to remove outer membrane which releases periplasmic protein and the pellet was cleaned by washing with 25% Triton X-100, 5M NaCl once, washing with 25% Triton X-100 once, washing with 4M Urea(4M urea, 0.1M Tris-Cl) once, 3 times of washing with TE buffer. Through this process, proteins except inclusion body were removed. The purity of antibody-toxin was analyzed on PAGE gel with densitrometry(TINA 2.0), and the purity of Fd-Ext-toxin and light chain was about 30%.

(Refolding of [B3(Fab)-Ext(4CLFA5X)-PE38]$_2$ Molecule)

Each inclusion body, B3(Fd)-Ext-PE38 and B3(L) was used in 1:1 molar ratio for refolding process. [Fab-toxin]$_2$ antibody-toxin with uncoupled Cysteine for disulfide-bond-bridge at the first amino acid position on Ext(molecule from pCE1) which was made in previous experiments, showed very low production yield after the refolding(Choi et al., 2001). The reason for this low productivity is because of the uncoupled Cysteine is too close to the Fab region causing scrambling with the internal Cysteines of Fab domain and another reason for it is because of the number of flexible amino acid in Ext is too small(total FA is 7, peptide linker LFA length is 13 in total) the three-dimensional hindrance between the two big PE38 molecules couldn't be overcome.

To solve this problem, the uncoupled Cysteine was transferred to the 15$^{th}$ position of Ext chain to get far from Fab region and the number of flexible amino acid (FA) of LFA chain was increased to 13(total amino acid number of LFA is 14, the dimer from pCW1) to give spaces and rotational freedom for effective refolding and dimerization. In this case the disulfide bond is formed between the cysteines on the inserted extension peptide. When the flexible extension peptide is inserted, the productivity of [B3(Fab)-Ext(15CL14FA13)-PE38]$_2$ has increased to 0.06% from 0.014% of the previous [B3(FabH1)-PE38]$_2$ (=[B3(Fab)-Ext(1CL13FA7)-PE38]$_2$. This is because the uncoupled Cysteine transferred to the 15$^{th}$ position doesn't cause disulfide bond scrambling with either Cysteines inside of Fab or on Ext and this does not cause any interference to the formation of the three dimensional structure. Also the increase of flexible amino acid in LFA makes the three dimensional hindrance between PE38 reduced.

Therefore, in this example the inventors tried to confirm that it is not true that the uncoupled Cysteine only at a specific position allows the formation of dimer without interfering interactions with Fab and/or PE38 functional group but that it is true that the uncoupled Cysteine on any point in some range of the position enables dimerization too. Also, it was confirmed with an uncoupled amino acid fixed at the middle 4$^{th}$ position and increasing the numbers of flexible amino acid in LFA was serially by 5 flexible amino acid that the number and the sequence of amino acid of LFA can be in certain range to enable the formation of dimer with various production yield and that it do not need to be of specific number and sequence as that of the previous molecules.

The inventors held experiments as below.

1) Comparing the production yield of [B3(Fab)-Ext(4CLFA5X)-PE38]$_2$ according to the LFA chain length and number of flexible amino acids when the Ext chain of Ext (4CL15FA11,4CL20FA16, 4CL25FA16) has 11, 16, 21 flexible amino acids.

2) Examining the effects of [B3(Fab)-Ext(4CLFA5X)-PE38]$_2$ having the disulfide bond formed by uncoupled Cysteine not locating in the 1$^{st}$ or 15$^{th}$ but 4$^{th}$ position.

3) Examining the effects of [B3(Fab)-Ext(AQ4CL20FA16)-PE38]$_2$ having AKPCIATQ (SEQ ID NO: 33) instead of SKPCISTK (SEQ ID NO: 34) in Ext sequence which is derived from the hinge of antibody.

The results are as followings.

1) When 11, 16, 21 flexible amino acids were inserted, the maximum production yield of [B3(Fab)-Ext(4CLFA5X)-PE38]$_2$ increased to 0.17~0.25%. This is 121~17.8 times higher than [B3(FabH1)-PE38]$_2$(32 [B3(Fab)-Ext(1CL13FA7)-PE38]$_2$) and 2.8~4.1 times higher than [B3(Fab)-Ext(15CL14FA13)-PE38]$_2$.

TABLE 4

| Plasmid name | Structure of Ext | Yield of dimer (%) | Position of Cys in Ext | Length of L (distance between Cys and F) | Number of GASQEND (SEQ ID NO: 21) in L |
|---|---|---|---|---|---|
| pCE1 | 1CL13FA7 | 0.016 | 1 | 13 | 7 |
| pCW1 | 15CL14FA13 | 0.06 | 15 | 14 | 13 |
| pMH21 | 4CL15FA11 | 0.18 | 4 | 15 | 11 |
| pMH22 | 4CL20FA16 | 0.23 | 4 | 20 | 16 |
| pMH23 | 4CL25FA21 | 0.25 | 4 | 25 | 21 |
| pMHS22 | AQ4CL20FA16 | 0.24 | 4 | 20 | 17 |

According to table 4, one can find the examples of the molecules with LFA peptide, which has 13 to 25 amino acids between the uncoupled Cysteine and PE38. Among these, the production yield of [B3(FabH1)-PE38]$_2$(=[B3(Fab)-Ext(1CL13FA7)-PE38]$_2$) which has 13 amino acids is 0.014%, which is nearly no production. But using 14, 15 amino acids which has insignificant difference with the above 13, the maximum production yield of dimer increased to 0.17~0.25%. This shows that for preventing the hindrance between PE38, the flexible amino acid containing LFA peptide is essential although peptides between uncoupled Cysteine and PE38 are similar. When inserting 11, 16, 21 amino acids containing LFA peptide, the production yield increases from 0.17% to 0.25% though it is in small quantities and this indicates L peptides with flexible amino acid are needed for preventing the hindrance between two PE38. Also, the case of pMH23(B3(Fd)-Ext(4CL25FA21)-PE38) indicates that, even though the 25 amino acid LFA having 21 non-bulky flexible amino acids exists between disulfide bond and PE38, this long length of LFA didn't allow PE38 functional group to disturb Fab refolding or binding activity and active dimer[B3(Fab)-Ext(4CLFA5X)-PE38]$_2$ was formed.

2) The production yield of [B3(Fab)-Ext(15CL14FA13)-PE38]$_2$ was 0.06% when the disulfide bond is transferred to the 15$^{th}$ location of extension chain but, when the disulfide bond is on the 4$^{th}$ location the maximum production yield increased to 0.17~0.25%. This indicates that the uncoupled Cysteine forming disulfide bond doesn't have to take specific position and the possible range is very wide to form appropriate disulfide bonds without disturbing the formation of tertiary and quaternary structure of neighboring binding domain and functional group which are massive structure. This example wants to shows whether the sequence, which has derived from natural antibody hinge region, on extension chain helps disulfide bonding for dimerization. For this, there are facts from the preceding experiment that the production yield of [B3(FabH1)-PE38]$_2$(=[(B3(Fab)-Ext(1CL13FA7)-PE38]$_2$) having Ext with modified sequence derived from antibody hinge and uncoupled Cysteine was 0.016%, and the production yield of [B3(Fab)-Ext(15CL14FA13)-PE38]$_2$ having Ext with modified sequence derived from antibody hinge and uncoupled Cysteine not on the hinge derived sequence but on irregular flexible sequence after the hinge derived sequence showed the increased yield to 0.06%. But, if when the uncoupled Cysteine was put into the middle of the $1^{st}$ and $15^{th}$ position, the production yield was higher than both of the previous $1^{st}$ and $15^{th}$ position Therefore, the conclusion for whether the hinge sequence derived from antibody has effects on dimerization is not clear.

3) For the construction of plasmid pMHS22, the Serine(S) on SKPCISTK (SEQ ID NO: 34) sequence which is derived from hinge was exchanged with Alanine(A) that has no —OH group. This is because the —OH group on Serine may make the space sterically too crowded and disturb three-dimensional structure to decrease production yield of dimer. Also, uncoupled Cysteine was put into the $4^{th}$ location and exchanged bulky amino acid Lysine(K) which takes big volume to flexible amino acid Glutamine(Q) to make AKPCIATQ (SEQ ID NO: 33). The productivity of [B3(Fab)-Ext(4CL20FA16)-PE38]$_2$ by pMH22 having SKPCISTK (SEQ ID NO: 34) and [B3(Fab)-Ext(AQ4CL20FA16)-PE38]$_2$ by pMHSS22 having AKPCIATQ (SEQ ID NO: 33) was similar which is nearly 0.2%.

Figure 4:
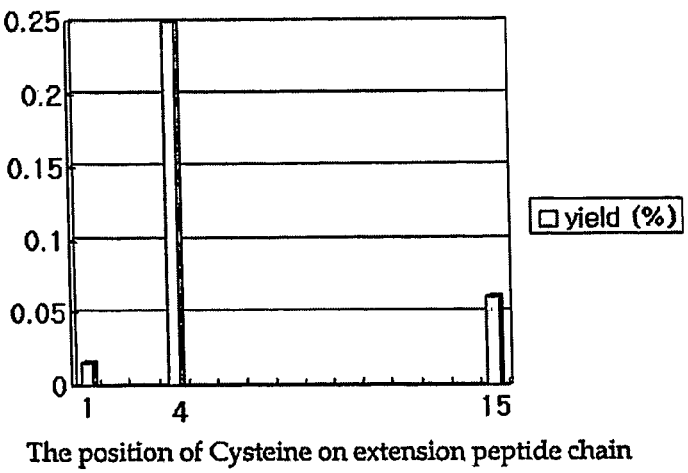
FIG. 4 is a graph showing the production yield according to the position of Cysteine at position 1, 4 and 15 on extension peptide chain.

Through this experiment, the conclusion for the dimerization of antibody-toxin which is a kind of fusion of binding domain and functional group is that the location of uncoupled Cysteine in extension chain doesn't have to be specific like naturally coupled Cysteines for intra- or inter-chain disulfide bond and it can have wide range for dimerization. The relationship between uncoupled Cysteine and dimerization is shown in FIG. 4.

Also, to decrease three dimensional hindrance between the big functional group PE38, the flexible amino acids are needed following uncoupled Cysteine, and according to the experiment the productivity increased with the increased numbers of flexible amino acids. There are 21 flexible amino acids in LFA(flexible chain) for independent refolding of PE38 and Fab and it did not cause inter-domain hindrance between Fab and PE38 though it is a 25 amino acid long length of flexible linker chain, and the formation of [B3(Fab)-Ext(4CL25FA21)-PE38]$_2$ is allowed with appropriate disulfide bond between uncoupled Cysteine.

(Purification of [B3(Fab)-Ext(4CLFA5X)-PE38]$_2$)

Figure 5:
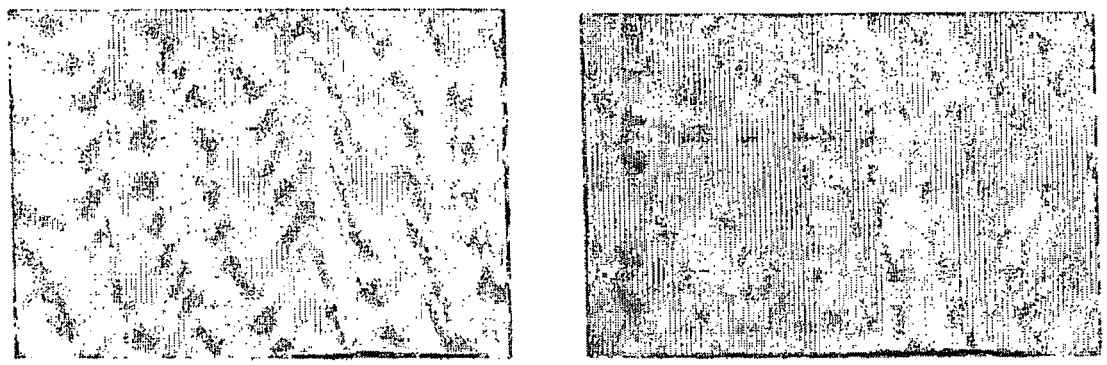
FIG. 5 shows antibody-toxin finally purified.

To purify refolded [B3(Fab)-Ext(4CLFA5X)-PE38]$_2$, the fact that PE has net negative charge was exploited and anion exchange resin was used. First, the one liter of dialyzed sample was loaded into Q-sepharose column and the sample was washed and eluted with buffer A and B. The eluted sample was analyzed on 12% reducing and 8% nonreducing SDS-PAGE electrophoresis. The fractions of divalent antibody-toxin was pooled and were gel filtrated using superdex 200 column and eluted with PBS. The final column result is on FIG. 5.

(Cytotoxicity Assay)

Using $^3$H-incorporation method, the cytotoxicity effect of antibody-toxin was examined on four cancer cell lines. The ADP-ribosylation ability of third domain of PE38 inactivates elongation factor II to inhibit protein synthesis. scFv-PE38 was used as reference molecule for comparison. KB3-1 cancer cell line was used as negative control cell. ID$_{50}$ is the concentration of antibody-toxin when [$^3$H]-leucine-incorporation into cancer cell decreases to 50%. The cytotoxicity assay was held three times each in triplicate samples and the triplicate values were taken average to evaluate the result. The source of error in triplicate cytotoxicity assay might be from sensitive cell condition, mix of active and inactive antibody-toxins obtained through in vitro refolding and purification, and contaminant proteins. But, although the three values are a little different from each other, they are in the range of experimental errors. The results showed same ID$_{50}$ values as that of the reference monovalent molecule and also lower values than that of the reference molecule, which means that the dimer has higher cytotoxicity than the reference. This is due to antigen density and structural conditions on the cell surface as observed in the previous case. More knowledge on cell surface antigen structure will make the explanation possible.

If cytotoxicity from divalent molecule is superior to monovalent molecules the treatment effect of divalent molecule will be higher at the same dosage. Also, the lowest limit of the therapeutic window that is determined by the minimum dosage showing the effect of the drug can be lowered by using the dimer as it has higher binding efficiencies than the monovalent and the same therapeutic effect can be obtained with less amount of dose. This means side effect caused by the functional groups with physiological activities can be overcome by the use of dimer as it can give same therapeutic effect with lower dose.

Example 2

The Dimerization and Effects of Antibody-Toxin Fusion that has Extension Peptide Chain(Ext) with Uncoupled Cysteine at the $15^{th}$ Position and 14 Amino Acids Linker(LFA) Containing 13 Flexible Amino Acids In this example, the B3(Fd)-Ext(15CL14FA13)-PE38 was newly constructed. The flexible peptide G4C(G4S)$_2$ (SEQ ID NO: 35) was inserted following the fourth Serine on extension chain SKPSISTKASGGPE (SEQ ID NO: 42) of B3(Fd)-PE38. The Cysteine on sequence derived from antibody hinge sequence was all changed into Serine that does not form disulfide bond. The composition of B3(Fd)-Ext(15CL14FA13)-PE38 is same to B3(VH)-B3(CH1)-SKPSISTKASGGGGCGGGGSGGGGSGGPE (SEQ ID NO: 36)-PE38. The uncoupled Cys on Ext forms disulfide binds between two B3(Fab)-Ext(15CL14FA13)-PE38 monomers. The uncoupled Cys was located at $15^{th}$ position of extension chain compared to the previous example which uses uncoupled Cys on $1^{st}$ position which is [B3(FabH1)-PE38]$_2$ (=[B3(Fab)-Ext(1CL13FA7)-PE38]$_2$) (protein from pCE1) to place Cys far from binding domain Fab and this showed whether the position of Cys doesn't have to be specific for disulfide bonding. Also, the inventors wanted to find out whether dimerization of B3(Fab)-Ext(15CL14FA13)-PE38 is enhanced by putting 13 flexible amino acids in peptide linker following uncoupled Cys which will give more spaces between PE38 and decrease three dimensional hindrances between them during dimerization.

The B3(Fab)-PE38 derived divalent immunotoxin is expected to have more merits than monovalent immunotoxin. First, the binding affinity will be stronger because it's divalent binding valency. Second, cytotoxicity against cancer cells will be better. Third, the stability in circulation of blood will be better. The longer flexible extension peptide chain was applied expecting that [B3(Fab)-Ext(15CL14FA13)-PE38]$_2$ which has longer flexible extension peptide chain has higher productivity and better refolding yield than [B3(Fab)-Ext(1CL13FA7)-PE38]$_2$ having about half number of flexible amino acid in linker L chain. (Choi. et al., 2001)

(Apparatus and Methods)

The construction of B3(Fd)-Ext(15CL14FA13)-PE38 fusion protein was performed by splicing PCR using four primers of the template pMC74(Fd-SKPSISTKASGGPE (SEQ ID NO: 42)-PE38 protein expressing vector), G4C(G4S)$_2$ (SEQ ID NO: 35) which follows after the fourth Serine on SKPSISTKASGGPE (SEQ ID NO: 42) sequence between Fd and PE38. The Fd and PE38 fragments from PCR were purified and splicing PCR was performed using the appropriate primers. The products from splicing PCR was purified and they were exchanged with appropriate part of pMC74(Fd-PE38 expressing vector) which was cut with Nde I and Sac II.

The expression of protein, isolation of inclusion body, refolding, isolation of protein and cytotoxicity assays were performed the same as in example 1.

(Construction of pCW1 Expression Vector and Isolation of Inclusion Body)

Figure 6:
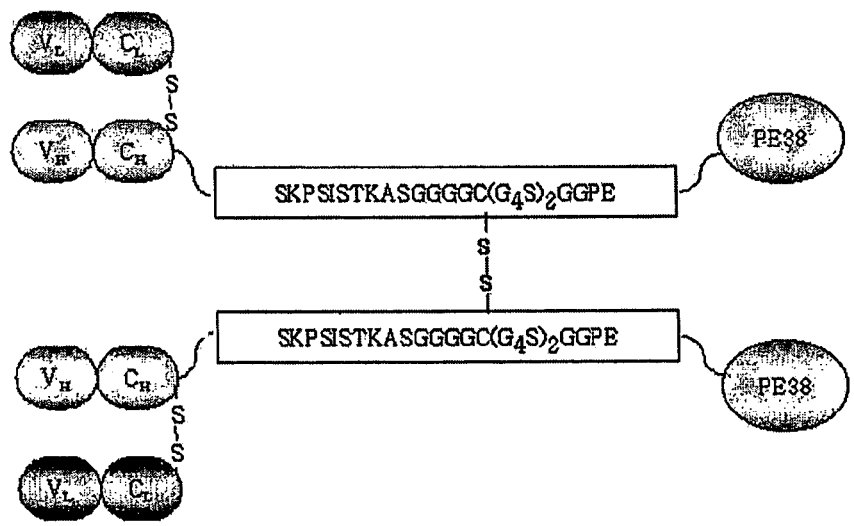
FIG. 6 shows the structure of [B3(Fab)-Ext(15CL14FA13)-PE38]$_2$ produced from pCW1. The sequence shown is SEQ ID NO:36.

The structure of pCW1 which expresses B3(Fd)-Ext(15CL14FA13)-PE38 chain composing [B3(Fab)-Ext(15CL14FA13)-PE38]$_2$ is shown on FIG. 6. B3(Fd)-Ext(15CL14FA13)-PE38 is a modified form of [B3(Fd)-SKPSISTKASGGPE (SEQ ID NO: 42)-PE38] using PCR. The peptide chain G4C(G4S)$_2$ (SEQ ID NO: 35) was inserted between S and G on KASGGPE (SEQ ID NO: 30) of [B3(Fd)-SKPSISTKASGGPE(SEQ ID NO: 42)-PE38]. The plasmids used are on table 5.

TABLE 5

| Name | Coding Proteins |
| --- | --- |
| pMC74 | B3(Fd)-SKPSIST-KASGGPE(SEQ ID NO: 42)-PE38REDLK (SEQ ID NO: 56) |
| pMC75 | B3(L) |
| pCW1 | B3(Fd)-SKPSIST-KASG4C(G4S)2GGPE(SEQ ID NO: 36)-PE38REDLK (SEQ ID NO: 56) |

The nucleotide sequence of pCW1 was confirmed through sequencing. The polypeptide was gained from the inclusion body of E. coli. The protein purity of inclusion body was measured as 40~60% by densitometry(TINA2.0).

(The Refolding of [B3 (Fab)-Ext(15 CL14FA13)-PE38]$_2$ Molecule)

The refolding procedure was performed by mixing in the inclusion bodies B3(Fd)-Ext(15CL14FA13)-PE38 and B3(L) in 1:1 molar ratio. The [B3(Fab)-CKPSISTKASGGPE (SEQ ID NO: 16)-PE38]$_2$ (=[B3(Fab)-Ext(1CL13FA7)-PE38]$_2$) immunotoxin which was reported previously was a form having the uncoupled Cysteine at the 1$^{st}$ position of the extension chain to form disulfide bond between two monomer, and it showed low production yield after refolding(Choi. et al., 2001). This is because of the location of uncoupled Cysteine that is too close to the Fab region, and also because of the three dimensional hindrance between the two big PE38. The solution for this is to transfer the uncoupled Cysteine far from Fab and increase the flexible amino acids in LFA to decrease the three-dimensional collision of PE. The designed molecule have increased number of flexible amino acids in LFA and increased spaces for the rotational freedom of PE that will help dimerization. The uncoupled Cysteine in extension peptide chain forms disulfide bond to form dimer[Fab-Toxin]$_2$, and LFA contains 14 amino acids of GASQEND (SEQ ID NO: 21) group. The dimer([B3(Fab)-Ext(1CL13FA7)-PE38]$_2$) containing Fd-CKPSISTKASGGPE (SEQ ID NO: 16)-PE38 from pCE1 showing low productivity is composed of 13 amino acids from the point of disulfide bond and the start point of PE. [B3(Fab)-Ext(1CL13FA7)-PE38]$_2$ (=Fd-SKPSISTKASGGGGCGGGGSGGGGS GGPE (SEQ ID NO: 36)-PE38) also has 14 amino acids in the same area but the productivity by refolding procedure was examined as 0.06% which is 4~5 times bigger than the dimer [B3(Fab)-Ext(1CL13FA7)-PE38]$_2$ (=Fd-CKPSISTKASG-GPE(SEQ ID NO: 16)-PE38) made from pCE1. Therefore, the insert of flexible amino acids increase refolding efficiency by allowing flexible movement of the chain and decreasing three dimensional collision at dimerization with each B3(Fab)-Ext(15CL14FA13)-PE38.

(Purification of [B3(Fab)-Ext(15CL14FA13)-PE38]$_2$)

Figure 7:
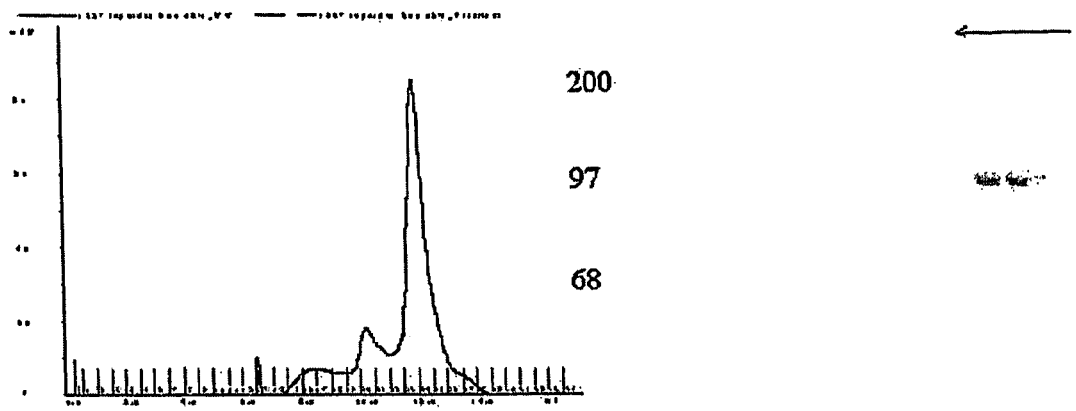
FIG. 7 shows the result profile of Superdex 200 column chromatography and SDS-PAGE analysis.

The same method was used as example 1. The final column result is shown on FIG. 7.

(Cytotoxicity Assay)

Figure 8:
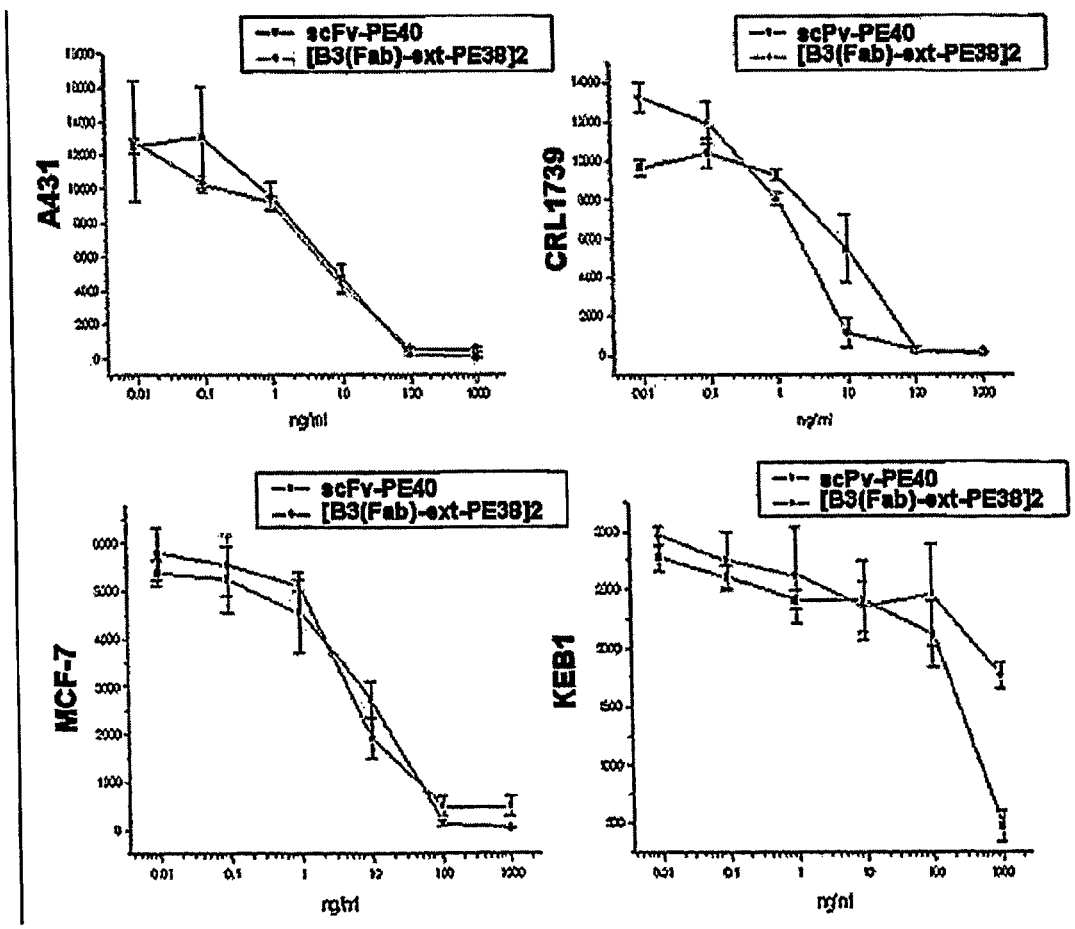
FIG. 8 is a graph showing representative cytotoxicity assay results of [B3 (Fab)-Ext-PE38]$_2$ and control molecule scFv-PE40.
Figure 9:
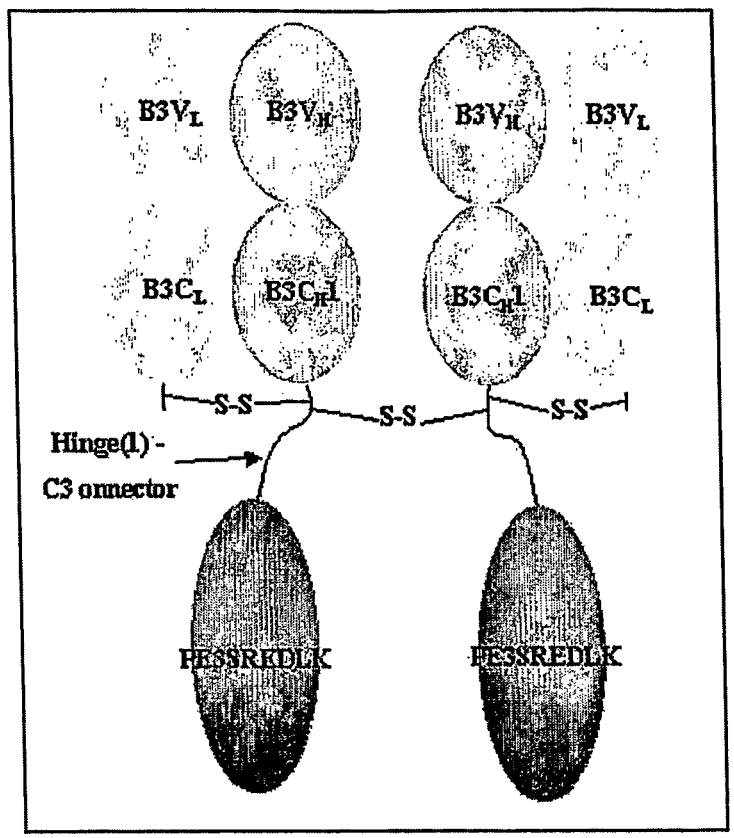
FIG. 9 shows the structure of [B3(FabH1)-PE382 (=[B3(Fab)-Ext(1 CL 13FA7)-PE38]$_2$). The sequence shown is SEQ ID NO:56.
Figure 10:
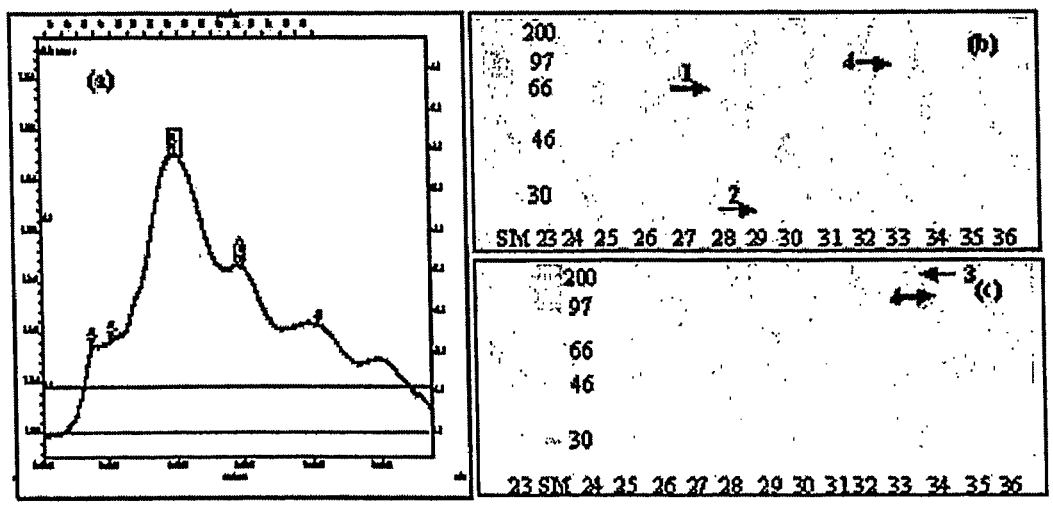
FIG. 10 shows the TSK-GEL G3000SW column chromatography result of B3 (FabH1)-PE38 and [B3 (FabH1)-PE38]$_2$.
Figure 11:
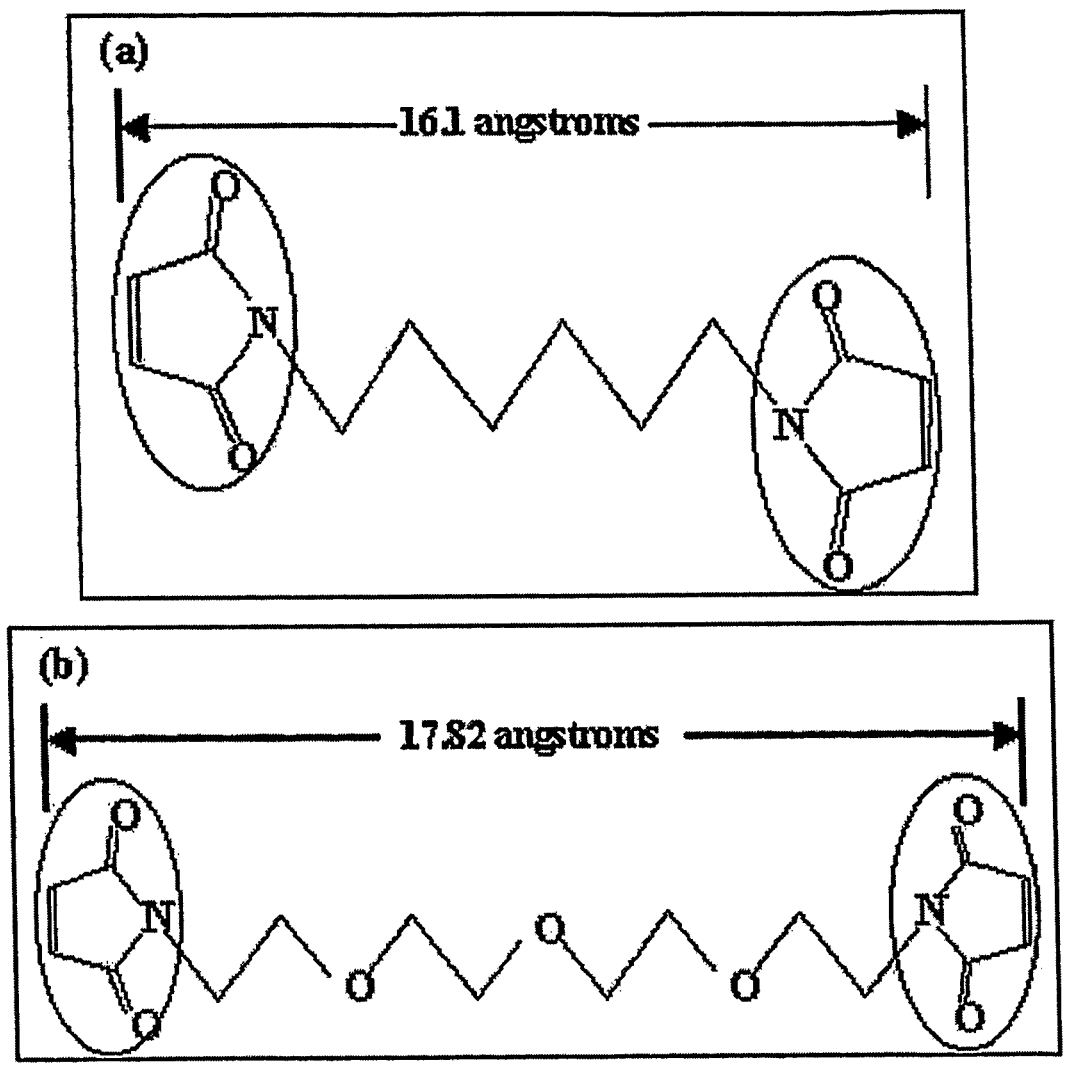
FIG. 11 shows the structure of BMH and BM[PEO]$_4$.

The experiment was performed in triplicate as same as example 1. The ID50 of divalent immunotoxin[B3(Fab)-Ext(15CL14FA13)-PE38]$_2$ was measured as 4 ng/mL with A431 cell line, 1 ng/mL with CRL1739 cell line, 5 ng/mL with MCF-7 cell line. The ID$_{50}$ of monovalent immunotoxin B3(scFv)-PE40 was measured highly as 5 ng/mL with A431, 12 ng/mL with CRL1739, 10 g/mL with MCF-7. The result for monovalent immunotoxin B3(scFv)-PE40 as a control was exactly the same as reported previously(Brinkmann et al., 1991). The ID$_{50}$ of B3(scFv)-PE40 is appropriate for using it as a control because the value was measured many times, and if the known value is gained is obtained in the assay it means that the error in the cytotoxicity assay is negligible. The results are shown on FIG. 8 and table 6.

TABLE 6

| | Cytotoxicity (ID50; ng/ml) on cell lines of B3 antigen | |
| --- | --- | --- |
| Cell line | scFv-PE40 | [B3(Fab)-Ext(15CL14FA13)-PE38]2 |
| A431 | 5 | 4 |
| CRL1739 | 12 | 1 |
| MCF7 | 10 | 5 |
| KB3-1 | >1000 | >1000 |

This results show that the divalent immunotoxin[B3(Fab)-Ext(15CL14FA13)-PE38]$_2$ has 12 times the higher cytotoxicity than the monovalent B3(scFv)-PE40 with CRL1739 cell line.

The CRL1739 cell line that showed 12 times differences in cytotoxicity assay is a stomach cancer cell line. This means that the divalent immunotoxin has more cytotoxicity depending on the surface structure against cancer cells that express same LeY antigen. If LeY is on very long and flexible structure and binding of divalent immunotoxin to two LeY antigens at same time is easy, divalent immunotoxin will bind two of LeY simultaneously showing more binding affinity than monovalent immunotoxin. If LeY is on non-flexible structure or LeY is too far apart from each other, then the binding will be the same for both divalent and monovalent immunotoxin as the binding of the immunotoxin to antigen is through only one binding domain to one antigen even though the molecule has divalent binding domain. In the case of cell line CRL1739, it seems like that it has LeY on a very long and flexible polysaccharide structure and allows [B3(Fab)-Ext(15CL14FA13)-PE38]$_2$ to bind two antigens simultaneously. The binding of antibody with antigen on cell surface depending on their interaction can stimulate the growth of the cell. Some cell growth was observed at very high concentration of divalent immunotoxin (data not shown) but not for monovalent immunotoxin. The previously reported monovalent B3 immunotoxin haven't been yet reported that it stimulates cell growth by interaction of antigen-antibody. The differences between monovalent and divalent immunotoxin on cell growth are remained to be investigated.

Example 3

The Dimerization of Antibody-Toxin Fusion that has Extension Peptide Chain(Ext) with Uncoupled Cysteine at the 1st Position and 13 Amino Acids Linker(LFA) Containing 7 Flexible Amino Acids The B3(Fab) and PE38 are used in constructing divalent immunotoxin [B3(FabH1)-PE38]$_2$ (=[B3(Fab)-CKPSIST-KASGGPE(SEQ ID NO: 16)-PE38]$_2$)(=[B3 (Fab)-Ext (1CL13FA7)-PE38]$_2$). The divalent immunotoxin B3 has about 174.4 kDa of molecular weight and comprises two light chain of B3 and two chains composed of B3(Fd) fused with PE38. There are three Cysteines on the hinge sequence of B3 antibody. The rear two Cysteines are changed to Serines and only the front Cysteine is used to make the Ext chain. It forms disulfide bond between monovalent immunotoxin to produce dimer.

(Materials and Methods)

The method used are same as example 1. MTT(3-[4,5-Dimethylthiazol-2-yl]-2,5-diphenyltetrazolium bromide) from Sigma Co. was used at 1.5 mg/mL final concentration. Cy5™ AutoRead™ sequencing kit for sequence analysis was a product from Pharmacia Biotech. The plasmids used are shown on table 7.

TABLE 7

| Plasmid Name | Coding Protein |
| --- | --- |
| pMC75 | B3(L) |
| pCE1 | B3(Fd)-CKPSISTKASGGPE (SEQ ID NO: 16)-PE38 |
| pMC74 | B3(Fd)-SKPSISTKASGGPE (SEQ ID NO: 42)-PE38 |
| pMC76 | B3(L)-KASGGPE (SEQ ID NO: 30)-PE38 |

The method using chromatography column was the same as example 1.

(Construction of Plasmid pCE1 Expressing B3(FdH1)-PE38=B3(Fd)-Ext(1CL13FA7)-PE38)

Plasmid pCE1(expressing B3(FdH1)-PE38) is a modified form of pMC74(expressing B3(Fd)-PE38=B3(Fd)-SKP-SISTKASGGPE (SEQ ID NO: 42)-PE38). PCR was performed to change the sequence to pCE1. (pCE1 expresses B3(FdH1)-PE38=B3(Fd)-CKPSISTKASGGPE (SEQ ID NO: 16)-PE38).

The constructed expression system was confirmed by DNA sequence analysis. Primers used were designed appropriately to be used with each template DNA and to code designed amino acid sequence. B3(L) is expressed from pMC75.

(Preparation of Protein)

The methods for expression of B3(FdH1)-PE38 and B3L, purification of spheroplast and inclusion body, quantity analysis of inclusion body, refolding procedure, purification of B3(FabH1)-PE38 and [B3(FabH1)-PE38]$_2$ were same as example 1.

(Measurement of [B3(FabH1)-PE38]$_2$ Formation According to Temperature Change)

[B3(FabH1)-PE38]$_2$ formation from B3(FabH1)-PE38 monomer isolated by Mono-Q was measured at 37° C., 40° C., 45° C., 53° C. incubating for 24 hours. [B3(FabH1)-PE38]$_2$ was purified with Mono-Q and proteins of each fraction were analyzed with electrophoresis.

(Measurement of [B3(FabH1)-PE38]$_2$ Formation Using Cross-Linkers)

B3(FabH1)-PE38 obtained from TSK-GEL G3000SW and cross-linkers, which are bis-maleimidohexane(BMH) and 1,11-bis-maleimidotetraethyleneglycol (BM[PEO]$_4$), were reacted together in molar ratio of 6:1, 5:1, 4:1, 3:1, 2:1, 1:1, 1:3 in reaction buffer to connect the Thiol(—SH) groups of Cysteine of two B3(FabH1)-PE38. The proteins were analyzed by electrophoresis.

(Cytotoxicity Assay of Purified Proteins Against Cancer Cells)

Same method with example 1 was used except following description. The viability of cancer cells was measured according to decomposition of MTT to analyze cytotoxic effect of purified B3(FabH1)-PE38 and [B3(FabH1)-PE38]$_2$. Cancer cells were cultured with immunotoxin and 20 µl of 5 mg/mL MTT was added. The samples were wrapped with aluminum foil and left alone at 37° C., 5% CO$_2$ incubator for 10 hours. The reduced MTT-formazan was centrifuged at 3000 rpm for 4~15 minutes to make MTT-formazan crystal to pellet and 200 µl of supernatant was removed. 0.016N acidic isopropanol 100 µl was added. Microfilter plate shaker was used at 300 rpm to melt MTT-formazan and the optical density was measured using ELISA READER at 570 nm. Results were average values of three samples.

(Purification of B3(FabH1)-PE38 and [B3(FabH1)-PE38]$_2$)

Same method as example 1 was used.

The quantity of B3(FabH1)-PE38 and [B3(FabH1)-PE38]$_2$ was 4.3 mg and 16.5 mg respectively which is 3.8% and 0.016% of total quantity of B3(FdH1)-PE38 and B3L used in refolding. The reason for the low productivity of dimer [B3 (FabH1)-PE38]$_2$ is that lots of B3(FdH1)-PE38 and B3L coagulate and precipitate to disappear during refolding and dialysis. Also the reason for the low productivity of [B3 (FabH1)-PE38]$_2$ in spite of 3.8% B3(FabH1)-PE38 produced, is that Cysteine is located in a place which is difficult for disulfide bond to form due to unfavorable interactions of Fab and/or PE38 or being in a wrong orientation or being hided inside of the three-dimensional structure. But the small quantity of [B3(FabH1)-PE38]$_2$ obtained in this example was assumed to be through the rare disulfide bond formation before complete refolding between small amounts of B3(FdH1)-PE38, which can happen before the disturbance on disulfide bond formation by Fab and PE38, and later the disulfide bond is formed with B3L and the dimers are produced.

(Measurement of [B3(FabH1)-PE38]$_2$ Formation According to Temperature Change)

Because the productivity of [B3(FabH1)-PE38]$_2$ is very low, the formation by disulfide bond between B3(FabH1)-PE38 was checked with heating the monomer B3(FabH1)-PE38 to relax the structure of the monomer and to free the Cysteines from the unfavorable interactions of Fab and/or PE38 and to allow the oxidation for disulfide bond formation. Productivity of [B3(FabH1)-PE38]$_2$ was highest at 45° C. heating observed with B3(FabH1)-PE38 monomer isolated from Mono-Q. But many other kinds of side products besides [B3(FabH1)-PE38]$_2$ was formed too.

(Measurement of [B3(FabH1)-PE38]$_2$ Formation Using Cross-Linkers)

To increase productivity of [B3(FabH1)-PE38]$_2$, the cross-linkers(BMH and BM[PEO]$_4$) was used to connect the —SH group between two B3(FabH1)-PE38. The formation of [B3 (FabH1)-PE38]$_2$ was hardly observed when the molar ratio of B3(FabH1)-PE38 and cross-linker was used at 6:1, 5:1, 4:1, 3:1, 2:1, 1:1, 1:3 in the reaction. This result shows when the refolding with cross-linker was performed, the Cysteines for disulfide bond still can not get close each other to be linked by the cross-linker because of unfavorable interactions with Fab and/or PE38, or because of being in a wrong orientation, or because of being hided in three-dimensional structure, or because the Lysine which follows after Cysteine is too big and interrupts the bonding between cross-linkers and Cysteines leading to the failure of forming a dimer between two monomers.

(Cytotoxic Assay Of Purified Proteins On Cancer Cells)

The cytotoxicity effect on cancer cells of B3(FabH1)-PE38 and [B3(FabH1)-PE38]$_2$ can be observed by measuring viability of cancer cells which is indicated by the amount of MTT-tetrazolium being reduced to MTT-formazan by the mitochondrial dehydrogenase. The cancer cells used were A431, MCF7, CRL1739, which have B3 antigens, and KB3-1 as a negative control, which doesn't have B3 antigen. B3(scFv)-PE40 is a single chain immunotoxin, which is a monovalent molecule, and it was used as reference molecule. The ID$_{50}$ which shows cytotoxic effect of B3(scFv)-PE40, B3(FabH1)-PE38 and [B3(FabH1)-PE38]$_2$ was 61.3 ng/mL, 30 ng/mL, 10.3 ng/mL respectively. However, MTT-tetrazolium has to be delivered to the mitochondria in the MTT assay and it may introduce errors depending on the conditions of each cancer cells. But B3(FabH1)-PE38 and [B3(FabH1)-PE38]$_2$ had 2 times and 6 times higher effects than B3(scFv)-PE40 respectively. However, the reference molecule showed very low cytotoxic activity compared to the previous reports reported as 2~5 ng/mL ID$_{50}$. This is because cytotoxic assay is very sensitive to conditions of the cells and the immunotoxins were not purified enough and contain impurities. As the errors of MTT assay is relatively large the reconfirmation of the results is preferable.

In conclusion,

1) B3(FdH1)-PE38 and B3L occupied 17~25% of the total expressed protein in the cell when they were over-expressed.

2) Production yield of B3(FabH1)-PE38 was 4.3 mg which is 3.8% and [B3(FabH1)-PE38]$_2$ was 16.5 μg which is 0.016% when prepared with B3(FdH1)-PE38 and B3L in 82 mg and 32.2 mg amounts respectively in the refolding procedure.

3) The productivity of proteins with correct conformation formed through 100-fold rapid dilution refolding procedure is very low, and 96% of the protein were incorrectly refolded and aggregated.

4) The highest productivity is obtained at 45° C. when [B3(FabH1)-PE38]$_2$ was formed by heating B3(FabH1)-PE38 monomer.

5) B3(FabH1)-PE38 doesn't form dimers by connecting the monomer with long cross-linkers like BMH and BM[PEO]$_4$.

6) The Cysteins used in disulfide bonding between B3(FabH1)-PE38 is placed in an environment difficult to form dimers.

7) The purified B3(FabH1)-PE38 and [B3(FabH1)-PE38]$_2$ prepared from large amount of materials showed 2 times and 6 times higher cytotoxicity respectively than B3(scFv)-PE40 reference molecule.

8) For high purity preparation of [B3(FabH1)-PE38]$_2$, large amount of materials are needed and the contaminating proteins have to be removed.

Example 4

The Dimerization of Antibody-Toxin that has Extension Peptide Chain(Ext) with Uncoupled Cysteine at $1^{st}$, $4^{th}$, $6^{th}$ position and affinity domain Containing Flexible Linker Peptide (LADFA) (SEQ ID NO: 14) Containing CH2, CH3 Self-Affinity Domain of Antibody and (G4S)$_2$ Sequence On this experiment, three uncoupled Cysteines were positioned at the frontal region of extension chain, and they form very thermodynamically stable dimer with three disulfide bonds. In other words, this is to test whether the big sequence Fab and big group PE38, which has natural internal Cysteines, can be refolded into right conformation without being scrambled with three uncoupled Cysteines on extension chain. In another words, this is to confirm whether binding domain-functional group fusion dimer can be formed in triple disulfide bonded thermodynamically highly stable structure while the extension chain connecting binding domain and functional group has multiple uncoupled Cysteines. Predicting whether the multiple uncoupled Cysteines will find their disulfide bond couple correctly without bothering or intermixing with neighboring big sequences to form dimer is not easy for manufacturers concerned.

[B3(Fab)-h(H123-CH2/CH3/Fc)-PE38R]$_2$ having Ext (LADFA) (SEQ ID NO: 14) was produced which has Fc, CH2, CH3 domain in LFA sequence having self-affinity for easy meeting of the Cysteines for dimerization and flexible amino acid sequence following the 'self-affinity domain'. CH3 domain was reported not to disturb antigen binding and induces homodimerization (Acpua et al., 1998, Ridgway et al., 1996). Also, the molecule with CH3 domain has similar antigen binding affinity and homodimerization ability as those with Fc domain which has both CH2 and CH3 domain (Alt et al., 1999). Therefore, the merit of stability of Fab-toxin in blood circulation is saved and also production yield of dimer[Fab-toxin]$_2$ has been increased through the insertion of Fc, CH2, CH3 domain that causes homodimerization(Wu et al., 2001). Also, binding affinity of divalent molecule and monovalent molecule was compared (Gall et al., 1999).

(Materials and Methods)

Figure 12:
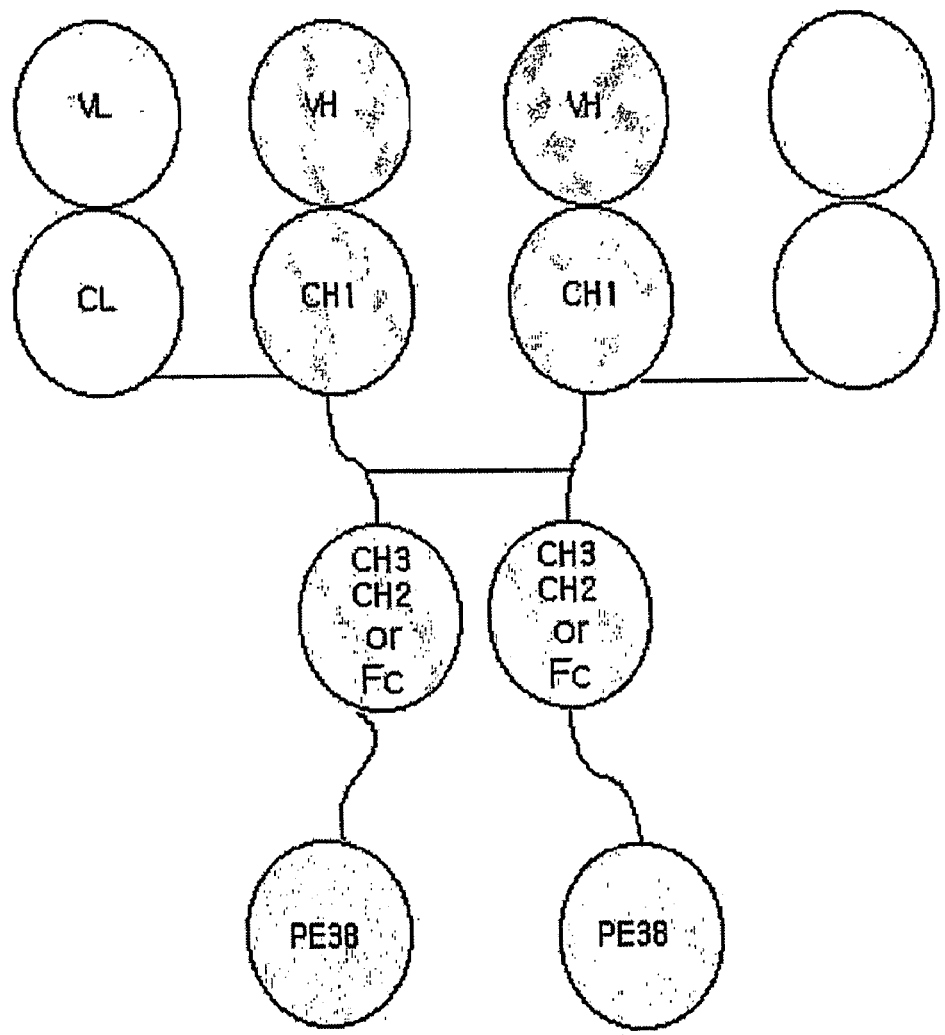
FIG. 12 shows the structure of antibody-toxin fusion produced from pLSC52, 32, 22.
Figure 13:
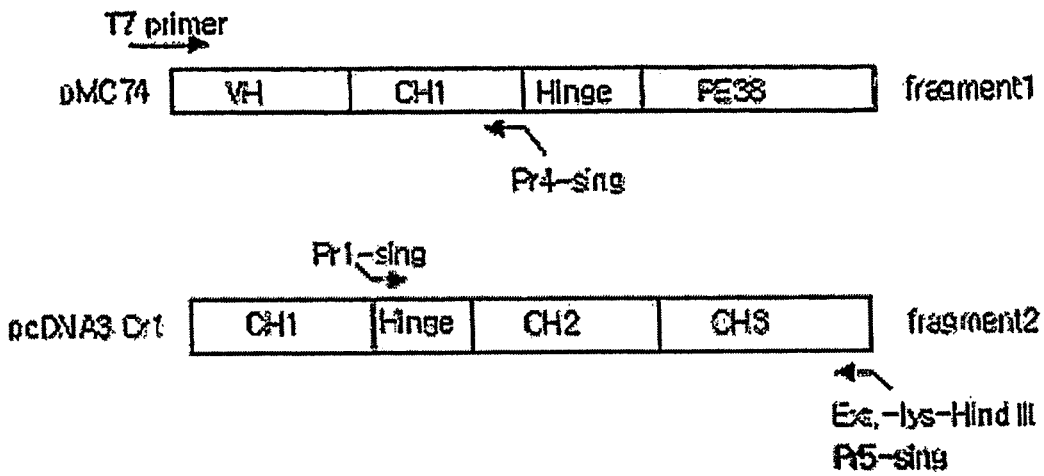
FIG. 13 shows the construction procedure of pLSC52 by PCR.
Figure 13:
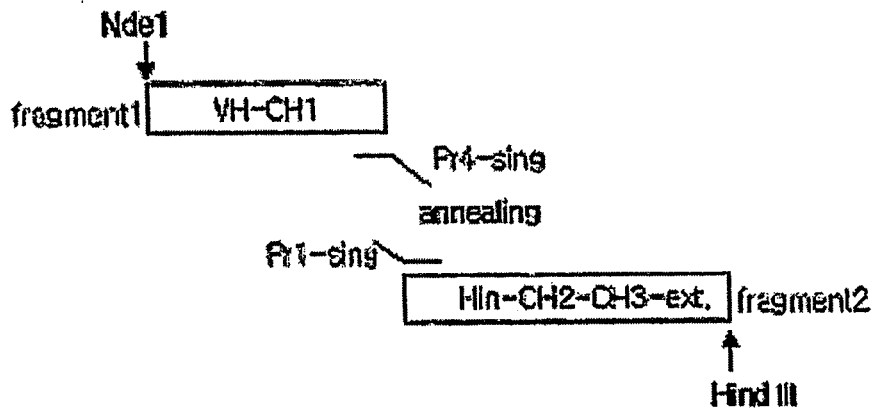
Figure 13:
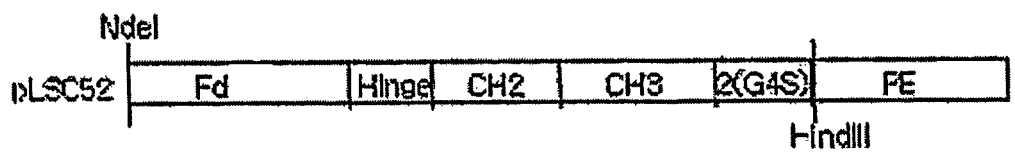
Figure 14:
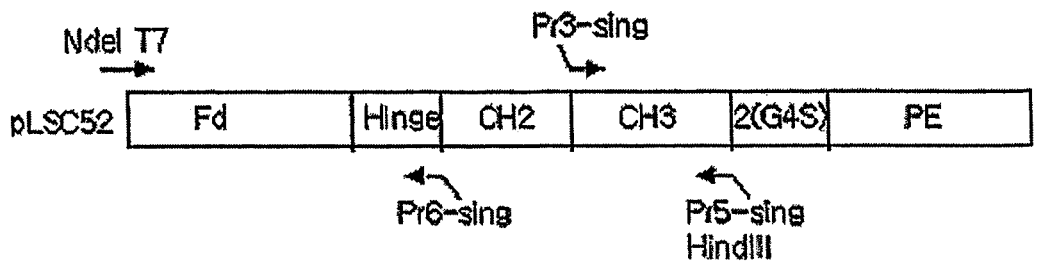
FIG. 14 shows the construction procedure of pLSC32 by PCR.
Figure 14:
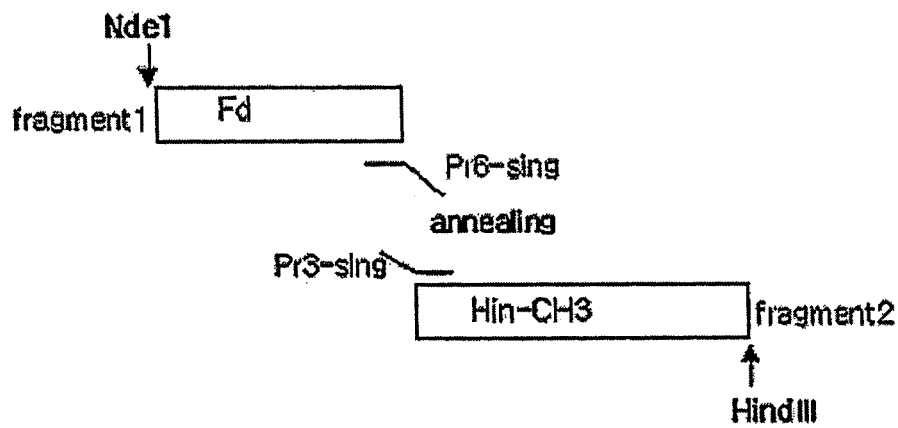
Figure 14:
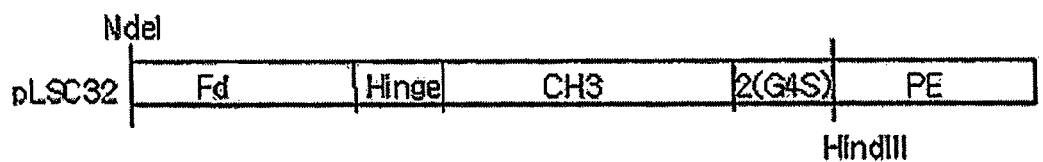
Figure 15:
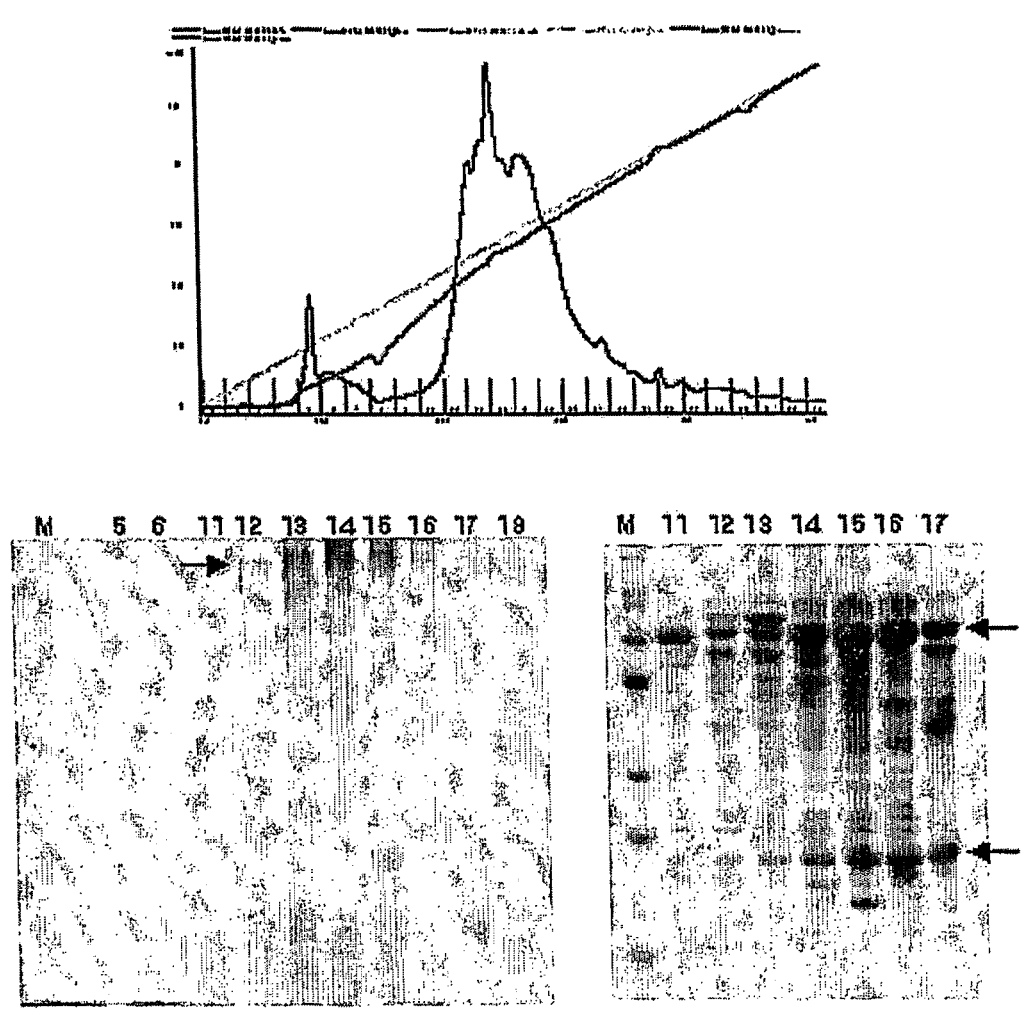
FIG. 15 shows the profile of Source-Q column chromatography and SDS-PAGE results of [B3(Fab)-h(H123-CH3)-PE38R]$_2$.
Figure 16:
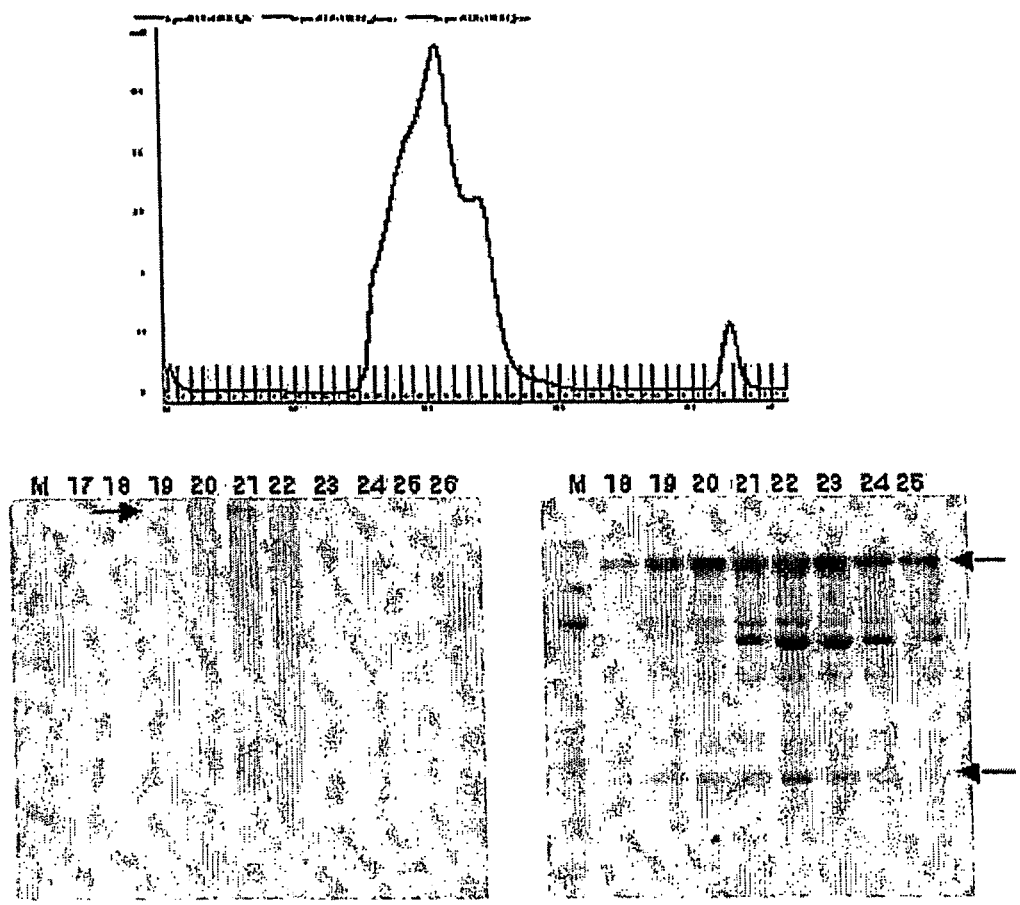
FIG. 16 shows the profile of Superdex 200 column chromatography and SDS-PAGE results of [B3(Fab)-h(H124-Fc)-PE38R]$_2$.
Figure 17:
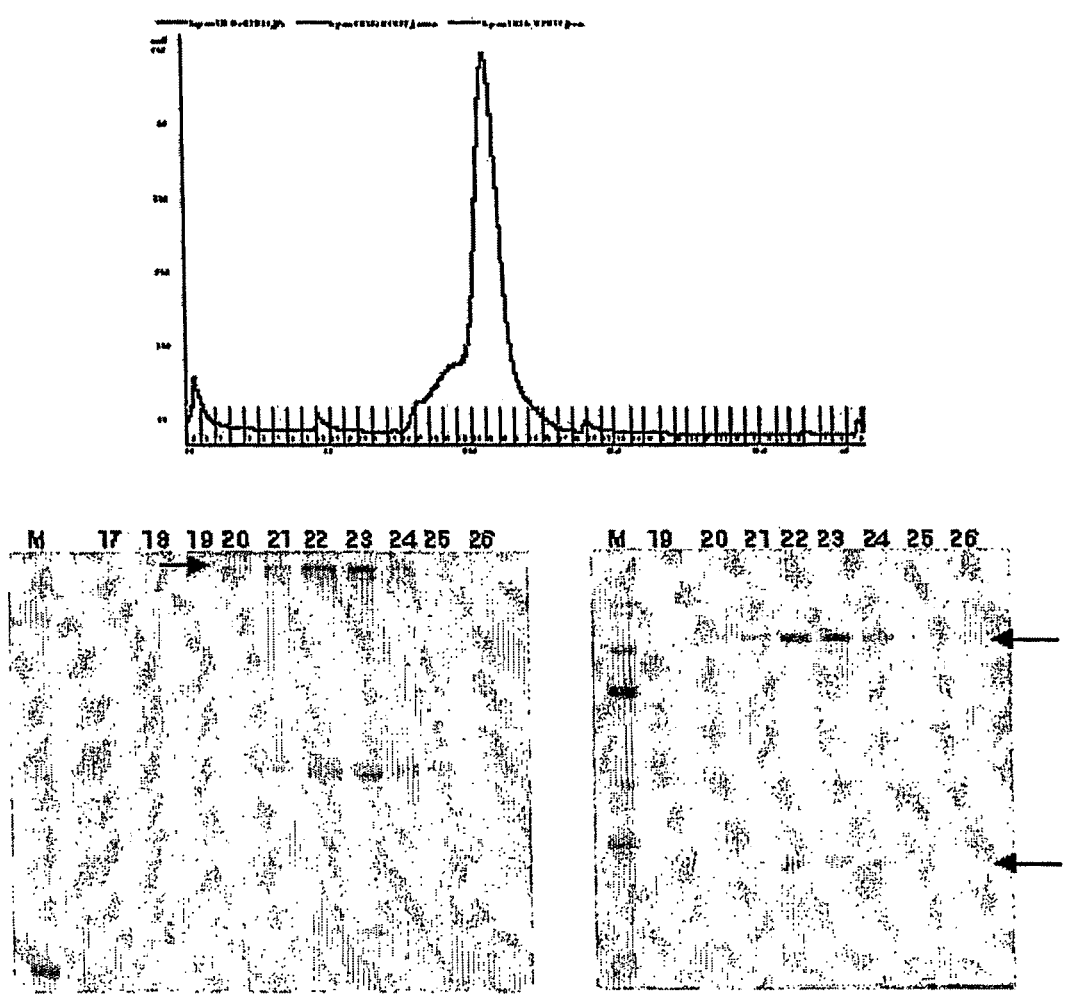
FIG. 17 shows the profile of Superdex 200 column chromatography and SDS-PAGE results of [B3(Fab)-h(H124-CH3)-PE38R]$_2$.
Figure 18:
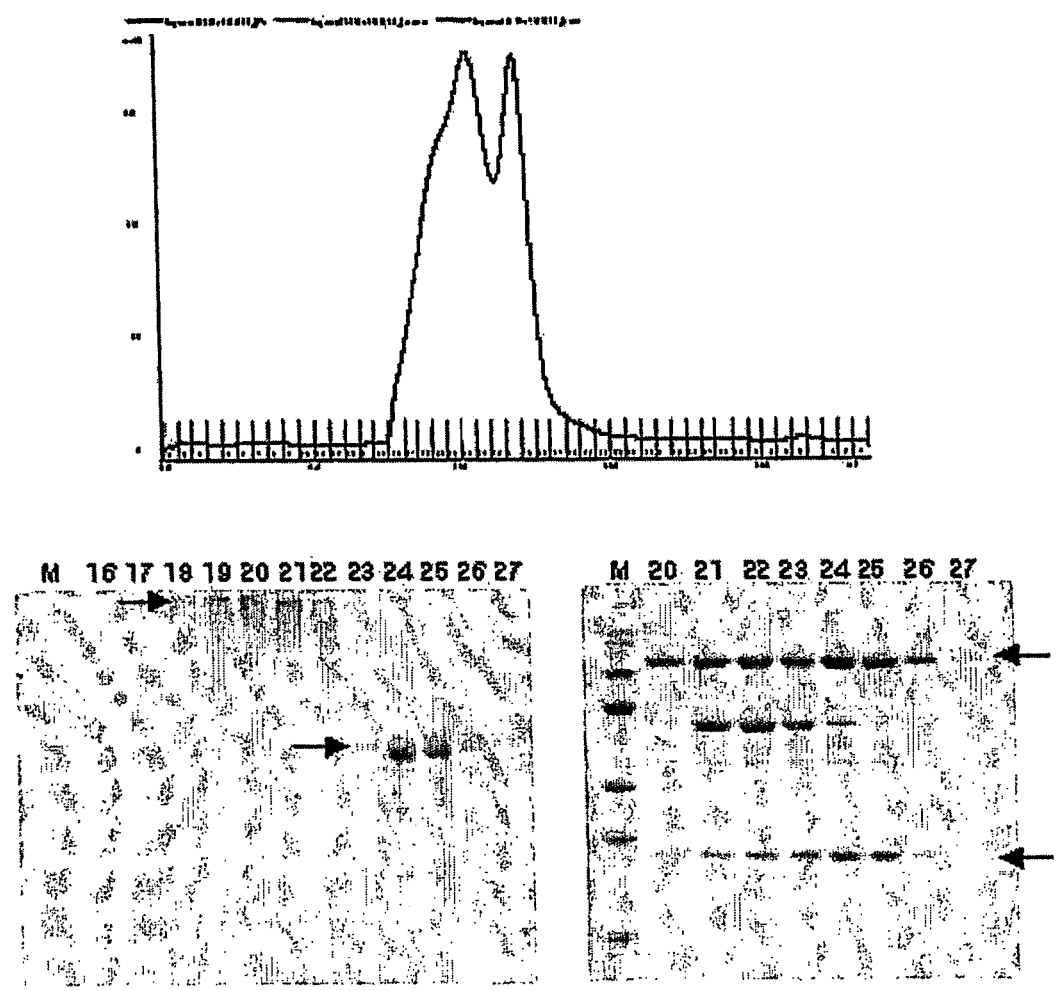
FIG. 18 shows the profile of Superdex 200 column chromatography and SDS-PAGE results of [B3(Fab)-h(H124-CH2)-PE38R]$_2$.

E. coli BL21(DE3) was used for protein expression system. For the construction of plasmid having Fab-h(H123-CH2/CH3/Fc)-PE38 chain gene, Fab-PE38 was obtained from pMC74 as a template and Fc region was obtained from human hinge(including three uncoupled Cysteines) and Fc containing pcDNA3Cγ1 as a template. For the light chain, 5'-end 6×His tagged chain from pMCH75 was used. Each name and construction procedure of the plasmid is on FIGS. 12, 13, 14 and table 8. Mediums, reagents, enzymes, columns are used the same as example 1.

TABLE 8

| Name | Coding Proteins |
|---|---|
| pLSC52 | B3(Fd)-human(H123-Fc)-(G4S)2(SEQ ID NO: 17)-KASGGPE (SEQ ID NO: 30)-PE38REDLK (SEQ ID NO: 56) |
| pLSC32 | B3(Fd)-human(H123-CH3)-(G4S)2(SEQ ID NO: 17)-KASGGPE(SEQ ID NO: 30)-PE38REDLK(SEQ ID NO: 56) |
| pLSC22 | B3(Fd)-human(H123-CH2)-(G4S)2(SEQ ID NO: 17)-KASGGPE(SEQ ID NO: 30)-PE38REDLK(SEQ ID NO: 56) |

TABLE 8-continued

| Name | Coding Proteins |
|---|---|
| pMC74 | B3(Fd)-SKPSIST-KASGGPE(SEQ ID NO: 42)-PE38REDLK (SEQ ID NO: 56) |
| pMCH75 | H6-B3(L) |

(Construction of Plasmid and Preparation of Protein)

To construct pLSC52 which contains all of the Fc, PCR of the region from hinge to Fc using pcDNA3Cγ1 as a template was performed. And PCR of Fd region from pMC74 was performed and splicing PCR was performed with these two fragments. Produced fragments and pMC74 were digested with Nde I and HindIII for insertion ligation. Plasmids with CH2, CH3 were constructed same way and called pLSC22 and pLSC32 respectively.

Methods for expression and isolation of protein and protein refolding procedure were the same as example 1. The molar ratio of LSC52 or LSC32 or LSC22 to MCH75 was 1:1 and the quantity of IT protein added was 40 mg/5 mL for the condition of 500 mL refolding and the method was same as example 1. Method for purification of refolded antibody-toxin was the same as example 1.

The method for cytotoxicity assay on 4 cell lines with [B3(Fab)-h(H123-Fc)-PE38]$_2$, [B3(Fab)-h(H123-CH3)-PE38]$_2$, [B3(Fab)-h(H123-CH2)-PE38]$_2$, [B3(Fab)-h(H123-CH2)-PE38] isolated from Superdex 200 was same as example 1.

(Production and Purification of IB Protein)

To produce [B3(Fab)-h(H123-CH2/CH3/Fc)-PE38]$_2$, plasmids pLSC22, pLSC32, pLSC52 encoding [B3(Fd)-h(H123-CH2/CH3/Fc)-PE38]$_2$ was constructed and pMCH75 was used for light chain.

The inclusion body protein preparation from T7 polymerase mass production system was repeated 12 times to get 38.2 mg/liter culture in average. Measured by densitometry analysis(Tina2.0) the purity of protein on the PAGE gel was 34.2% for heavy chain which was the average of 9 measurements and 40.9% for light chain which was the average of 3 measurements. Inclusion body was analyzed through SDS-PAGE. To enhance the purity of inclusion body, additional washing procedure treating with 4M Urea buffered by Tris-Cl pH7.4 for 3 hours was performed in addition. The purity of inclusion body was over 30% and the protein folding products were observed.

(Refolding of Proteins)

Disulfide bond during refolding procedure can be formed in two different kinds. One is disulfide bond inside the domain chain, intra-chain disulfide bond, and the other is disulfide bond between the chains, inter-chain disulfide bond. B3(Fd)-h(H123-CH2/CH3/Fc)-PE38 from pLSC22, pLSC32, pLSC52 and light chain from pMVH75 forms disulfide bond between Fd and L in refolding solution and composes Fab domain. Disulfide bonds are formed between the H123 Cysteine on two of B3(Fd)-h(H123-CH2/CH3/Fc)-PE38 monomer to make a dimer molecule.

(Purification of Refolded Antibody-Toxin)

After the purification, the yield of [B3(Fab)-h(H123-Fc)-PE38R]$_2$ which has Fc was the lowest value because the molecule size is relatively big(divalent: 228 kd) and the refolding is easily disturbed. [B3(Fab)-h(H123-Fc)-PE38]$_2$ which has both the CH2 and CH3 domains had a dragging bands other than the right size refolded band compared to molecules which has only one domain. This is because the size of [B3(Fab)-h(H123-Fc)-PE38R]$_2$ is big to make other false molecules during refolding.

[B3(Fab)-h(H123-CH3)-PE38]$_2$ which has CH3 didn't show the peaks of divalent and monovalent molecule separated on Superdex 200 column. This is because they exist as divalent form while being isolated through superdex200 column because of the strong self-affinity of CH3 domain. But during SDS-PAGE, the dimer molecules that is formed only by CH3 affinity but not by covalent disulfide bond falls apart and are observed as monomers on the SDS-PAGE. According to band intensity, the dimers formed by disulfide bonds on the Ext or formed by CH3 affinity are in similar quantity. Therefore the CH3 region is effective for dimerization of Fab molecule keeping them in close proximity, and refolding with dimer formation will take place though the numbers of uncoupled Cysteine is 3. The immaturation of disulfide bonds within affinity domain held dimers could be matured by long exposure to oxygen in the air. The immaturation of disulfide bonds are well known to manufacturers concerned who are experienced.

Finally, the quantity of [B3(Fab)-h(H123-CH2)-PE38]$_2$ which has CH2 is small but that of monovalent is big. This shows that CH3 self affinity is much stronger than CH2 self affinity to form more dimer. Through the known fact that self affinity of CH2 is very weak and through the experimentally observed fact that dimer which only has CH2 domain forms in very small quantity, it can be deduced that the dimer can be formed through disulfide bond even in the case of the three uncoupled Cysteines on the extension chain with small helps from the affinity domain.

(Cytotoxicity Assay)

Cytotoxicity effect of purified immunotoxin[B3(Fab)-h(H123-CH2/CH3/Fc)-PE38]$_2$ were tested on 4 cancer cell lines. According to cell types and culture conditions, the effect of divalents and monovalents differed.

(Productivity of Dimerization)

TABLE 9

| Refolding | [B3(Fab)-h(H123-Fc)-PE38]2 | [B3(Fab)-h(H123-CH3)-PE38]2 | [B3(Fab)-h(H123-CH2)-PE38]2 |
|---|---|---|---|
| 1st (240 mg/3 L) | 148 g 0.06% | 455 g 0.19% | 198 g 0.08% |
| 2nd (80 mg/1 L) | 44 g 0.05% | 146 g 0.18% | 78 g 0.10% |
| 3rd 80 mg/1 L | 47 g 0.06% | 162 g 0.20% | 59 g 0.07% |

In the case of [B3(Fab)-Ext(15CL14FA13)-PE38]$_2$, which has extension peptide chain SKPSISTKASG4C(G4S)$_2$GGPE (SEQ ID NO: 36) between Fab and PE38, the Ext (15CL14FA13) has decreased the steric hindrance between PE molecules, and productivity of this molecule was 0.06%.

In this experiment, dimerization was induced using CH3 domain affinity and the productivity was 0.19%. This is three time higher compared to [B3(Fab)-Ext(15CL14FA13)-PE38]$_2$. The productivity using CH2 domain was 0.08%, and using Fc domain was 0.06%. These two results are because of the difficulties in refolding of self affinity region and weak affinity of CH2. These are similar result to that of [B3(Fab)-Ext(15CL14FA13)-PE38]$_2$, and it means that these two cases didn't help the dimer production. However the manufacturers concerned can predict they will get good productivity if they use smaller size and stronger affinity domain. Especially, in the case of [B3(Fab)-h(H123-Fc)-PE38R]$_2$ which has CH3 domain, productivity was 0.06% because the size was too big for the proper folding.

According to the result above, putting self-affinity domain in LFA induces assembly between uncoupled Cysteine, and the disulfide bond formation even with three Cysteines can take place normally without disturbing the sterical conformation of binding domain and functional group domain. And also, this triple disulfide bonded dimer is more stable at room temperature when it is left alone and more resistant to damage by proteinase than single disulfide bonded dimer.

Example 5

Dimerization of [B3(Fab)-Cytosine Deaminase]$_2$ which has Fab of B3 Antibody as a Binding Domain and Cytosine Deaminase as Functional Group Up to Now, Monoclonal Antibodies, Monoclonal Antibody Treatments, Toxins and radionuclide complexes and others have been studied for many years. In recent years, many treatments based on monoclonal antibodies were clinically approved (Rituxan, Herceptin, Panorax). And some other treatments are in clinical demonstration.

To use big molecules as successful therapeutic agent for solid tumor, transmission hindrance into tumor mass, foreign antigen, efficacy of complex treatment and efficient transfer from monoclonal antibody into cancer cell and others must be overcome.

Alternative plan for therapeutic agent delivery is to undergo two steps for cancer treatment. Once the complex binds to cancer cell and be removed from blood circulation, an enzyme activates anti-cancer prodrug to become activated drug. The isolated drug can be transmitted into tumor mass and eliminates both monoclonal antibody binding cells and non-binding neighboring cells.

These treatments are called Antibody-Directed Enzyme Prodrug Therapy(ADEPT) which is a new method for selective cancer treatment. It introduces enzyme-antibody complex to change harmless prodrug at cancer cell surface into cytotoxic compound selectively. Bagshawe first reported this idea at 1987.

The first step of ADEPT is that antibody-enzyme complexes accumulate on cancer cells. As time passes, the complex gets degraded in blood and normal tissues. The second step is to introduce harmless prodrug and it changes into cytotoxic drug by enzymes from complexes.

Through this method, the cancer specificity increases and can deliver higher dose of drugs than direct administration. Also, one molecule of enzyme can amplify cytotoxicity by catalyzing many prodrugs into activated drugs and activated drugs have small molecular weight to be easily diffused near to cancer cells. As a bystander effect, a unique character of ADEPT, the cells near the cancer cells also get killed.

There are various monoclonal antibodies, enzymes and prodrugs that can be applied to ADEPT. Among enzymes there is yeast cytosine deaminase which catalyze exchange of cytosine into uracil and it can change anti-mold reagent 5-Fluorocytosine(5-FC) into 5-Fluorouracil(5-FU) as an anti cancer agent. Especially the yeast cytosine deaminase is reported to have more remedial value than bacterial enzymes used in enzyme-prodrug treatment. In addition, yeast cytosine deaminase prevents prodrug activity by restriction enzymes in blood or cells because it's from non-mammal, which has no homology to mammals. And it can be used easily with large amount because it has no translational modifications on it.

Pharmaceutical efficacy and toxicity must be clinically demonstrated before use and this is the dormant problem of applying ADEPT. However, 5-FU, which is used present clinically, can be used at colon carcinoma, for which it is hard to use other chemical agents. And cytotoxicity of drug and prodrug was confirmed at H2981 human lung adenocarcinoma cells. It is proved that there is no cytotoxicity in 5-FC having no effect at 200 uM concentration compared to 5-FU which has ID$_{50}$=20 μM.

On this experiment, recombinant protein molecule [B3(Fab)-cytosine deaminase]$_2$ for ADEPT application was constructed. This molecule was made by modification of Fab to be a divalent molecule and keeps the structural stability and the turnover rate of Fab. The second disulfide bond in the hinge was used for dimerizing monovalent Fab-enzyme to divalent molecule. Since this molecule is divalent, the binding affinity will be more than 2 times stronger and since the enzyme quantity has increased two times, the cytotoxicity will increase more. Also, although the IgG didn't have complete free rotation ability due to the three disulfide bonds of Fab region on the hinge, [B3(Fab)-enzyme]$_2$ has free rotation ability on its binding domain, and it will lead to stronger binding to antigens spread over the cells.

Though [B3(Fab)-cytosine deaminase]$_2$ is a big molecule, it has strong equilibrium binding affinity, fast binding reaction rate, increment of enzyme administration and long activity turn over rate in blood circulation system, and it will show higher efficacy than Fv derivatives.

(Apparatus and Methods)

The same method was used as example 1. For the construction of plasmid containing B3(Fd)-yCD gene, chromosomal DNA from *Saccharomyces cerevisiae* was used for template and pMC74 was used as template for Fab region. For the light chain, pMCH75, which is 6×His tagged on 3'-end was used as a template. Mediums, reagents, enzymes and columns were used the same as example 1. Constructed plasmids are shown on table 10.

TABLE 10

| Plasmid | Protein Sequence |
|---------|------------------|
| pKL1 | H6-CDase |
| pKL2 | B3(Fd-SKPCIST-KAS-(G4S)2-GGPE(SEQ ID NO: 57)-CDase-H6 |
| pKL3 | B3(Fd-SKPCIST-KAS-(G4S)2-GGPE(SEQ ID NO: 58)-CDase |
| pKL4 | H6-B3(Fd-AKPCIAT-QAS-(G4S)2-GGPE(SEQ ID NO: 59)-CDase |

(Construction of Plasmids)

Plasmid which expresses B3(Fd)-yCD fusion protein was constructed from PCR using CDase containing region of *Saccharomyces cerevisiae* chromosomal DNA as a template and two primers below. The CDase was purified and recombination with pMC74 led to recombinant plasmid pKL1.

Primer 1 (SEQ ID NO: 37): 5'-GGC-CCA-TAT-GCA-TCA-CCA-TCA-CCA-TCA-CGT-GAC-AGG-GGG-AAT-G-3'

Primer 2 (SEQ ID NO: 38): 5'-TTG-GTT-TGA-AGA-TAT-TGG-TGA-GTA-GGA-ATT-CGG-CC-3'

Primer 1 binds to 5'-end of CDase. Primer 2 binds to 3'-end of CDase to be used in CDase purification by PCR.

From PCR using pKL1 as a template with two primers below, CDase fragment was gained and it was recombined with PE of pMC22 to produce pKL2.

Primer 3 (SEQ ID NO: 39): 5'-GGC-CCC-CGA-GGT-GAC-AGG-GGG-AAT-G-3'

Primer 4 (SEQ ID NO: 40): 5'-GAA-GAT-ATT-GGT-GAG-CAT-CAC-CAT-CAC-CAT-CAC-TAG-GAA-TTC-GGC-C-3'

Primer 3 binds to 5' end of CDase. And primer 4 having six Histidines binds to 3' end of CDase to be used in CDase purification by PCR.

pKL2 has B3(Fd)-SKPCISTKAS-GGGGSGGGGS-GGPE (SEQ ID NO: 57)-CDase-6His.

CDase region from pKL1 and CDase region from pKL2 was recombinased to produce pKL3. pKL3 is B3(Fd)-SKPCISTKAS-GGGGSGGGGS-GGPE (SEQ ID NO:58)-CDase and doesn't have six His at the 3' end, pKL4 was constructed as following. PCR was performed by using template pMC74 and two primers below to gain Fd fragment which has six His on 5'-end and recombined with pKL3 to produce pKL4.

Primer 5 (SEQ ID NO: 41): 5'-GGC-CCA-TAT-GCA-TCA-CCA-TCA-CCA-TCA-CGA-TGT-GAA-GCT-GGT-GGA-GTC-T-3'

Primer 6 (SEQ ID NO: 29): 5'-GGG-AAT-TCA-TTA-AGC-TTG-TGT-AGC-TAT-GCA-AGG-CTT-AGC-ACC-ACA-3'

Primer 5 has six His and binds to Fd region. Primer 6 has AKPCIATQAS (SEQ ID NO: 22) and binds to 3' end of Fd.

The nucleotide sequence of plasmid pKL4 was confirmed by ALFexpress Dedeoxy Sequencing Kit(Amersham Pharmacia).

The method for protein expression and isolation, protein refolding, purification of refolded antibody-toxin was the same as example 1.

Cytotoxicity assay was performed on 4 kinds of cell lines with [B3(Fab)-CDase]$_2$ isolated by Superdex200 and the same method was used as example 1.

Through preceding methods, molecules purified had normal binding activity and functional group. And the binding activity of binding domain and cytosine activity of functional domain of the purified molecule was confirmed to be normal.

Example 6

The Dimerization and Increase of the Length of Flexible Chain(LFA) with the Uncoupled Cysteine Fixed at the 4$^{th}$ Position on Extension Peptide Chain(Ext)

The inventors increased the length of peptide linker(L) which is from uncoupled Cys on Ext to functional group to find out the relations with dimerization. The peptide linker(L) must be long enough to give spaces for the refolding to occur without disturbance from the sterical collision between two functional groups when dimerization occurs between two monovalent binding domain-functional domain fusion. Also, the peptide linker must have good flexibilities being composed of flexible amino acids to allow the functional groups to get separated widely enough in an appropriate angle. But if the peptide linker is too long, the uncoupled Cysteine on Ext will have too much freedom to move and meet the other naturally coupled Cysteines of intra-chain and inter-chain disulfide bond to get scrambled leading to inactivation of the molecule. And also since the peptide linker does not have a definite structure, it might penetrate into structures of binding domain or functional group while refolding to disturb their correct refolding.

To find out the relations between the length of the peptide linker and dimerization, plasmids were constructed as below, pMH28: B3(Fd)-SKPCG (SEQ ID NO: 31) - - - PE38; Ext(4CL1FA1)

pMH29: B3(Fd)-SKPCKASPE (SEQ ID NO: 32) - - - PE38; Ext(4CL5FA3)

pMH30: B3(Fd)-SKPCISTKASGGPE (SEQ ID NO: 46) - - - PE38; Ext(4CL10FA6)

pMH34: B3(Fd)-SKPCISTKAS(GGGGS)4GGPE (SEQ ID NO: 51) - - - PE38; Ext(4CL30FA26)

pMH35: B3(Fd)-SKPCISTKAS(GGGGS)5GGPE (SEQ ID NO: 52) - - - PE38; Ext(4CL35FA31)

pMH36: B3(Fd)-SKPCISTKAS(GGGGS)6GGPE (SEQ ID NO: 53) - - - PE38; Ext(4CL40FA36)

pMH37: B3(Fd)-SKPCISTKAS(GGGGS)7GGPE (SEQ ID NO: 54) - - - PE38; Ext(4CL45FA41)

pMH38: B3(Fd)-SKPCISTKAS(GGGGS)8GGPE (SEQ ID NO: 55) - - - PE38; Ext(4CL50FA46)

The protein chains above have Cys on LFA on 4$^{th}$ position of Ext and the peptide linker(L) has 1, 5, 10, 30, 35, 40, 45, 50 amino acids each containing 1, 3, 6, 26, 31, 36, 41, 46 non-bulky flexible amino acids.

The eight molecules of [B3(Fab)-Ext(4CLxxFAxx)-PE38]$_2$ type in this example were made to have the same possibilities of steric hindrance and intermixing that can be caused by the uncoupled Cys by fixing the Cys at 4$^{th}$ position on the Ext chain. And the amino acids following the uncoupled Cys were kept the same except the numbers of flexible amino acid was increased in five amino acids step to increase the peptide linker length and the sterical space was expanded with the same step. Among these molecules, the molecule with the shortest L having 1 amino acids which is Ext(4CL1FA1) and the longest L having 50 amino acids which is Ext(4CL50FA46) showed very low productivity.

Therefore, this example shows that when the peptide linker (L) has over 50 amino acids, it is impossible to get dimer made through the disulfide bond bridge between the two fusion monomers of 50 kD Fab domain of B3 antibody and 38 kD functional group PE38.

(Materials and Methods)

The same materials and methods were used as example 1.

(Construction of Plasmids)

The expression plasmids were constructed by PCR using primers which are appropriate for each DNA sequence. Used templates were same to example 1 and the same plasmids were used as example 1. The procedure for inserting GGGGS (SEQ ID NO: 17) sequence repeatedly was done by restriction and ligation.

(Protein Expression and Isolation of Inclusion Body)

Same methods were used as example 1.

(Refolding Procedure and Isolation of Proteins)

Same methods were used as example 1.

(Construction of Expression Vector and Isolation of Inclusion Body)

The coding nucleotide sequences obtained through PCR and cloned in expression plasmids was confirmed by sequence analysis.

The proteins in the form of inclusion body was analyzed by densitometry analysis(TINA2.0) on PAGE sample and the purity of protein chain was in 25~30%.

(Refolding of [B3(Fab)-Ext(4CLFA5X)-PE38]$_2$ Molecule)

TABLE 11

| Plasmid name | Structure of Ext | Yield of dimer (%) | Position of Cys in Ext | Length of L (distance bet. Cys and F) | Number of GASQEND (SEQ ID NO: 21) in L | Note |
|---|---|---|---|---|---|---|
| pMH28 | Ext(4CL1FA1) | <<0.01 | 4 | 1 | 1 | |
| pMH29 | Ext(4CL5FA3) | 0.01 | 4 | 5 | 3 | |
| pMH30 | Ext(4CL10FA6) | 0.04 | 4 | 10 | 6 | |
| pCE1 | Ext(1CL13FA7) | 0.016 | 1 | 13 | 7 | Example3 |
| pCW1 | Ext(15CL14FA13) | 0.06 | 15 | 14 | 13 | Example2 |
| pMH21 | Ext(4CL15FA11) | 0.18 | 4 | 15 | 11 | Example1 |
| pMH22 | Ext(4CL20FA16) | 0.23 | 4 | 20 | 16 | Example1 |
| pMH23 | Ext(4CL25FA21) | 0.25 | 4 | 25 | 21 | Example1 |
| pMHS22 | Ext(AQ4CL20FA16) | 0.24 | 4 | 20 | 17 | Example1 |
| pMH34 | Ext(4CL30FA26) | 0.32 | 4 | 30 | 26 | |
| pMH35 | Ext(4CL35FA31) | 0.17 | 4 | 35 | 31 | |
| pMH36 | Ext(4CL40FA36) | 0.21 | 4 | 40 | 36 | |
| pMH37 | Ext(4CL45FA41) | 0.08 | 4 | 45 | 41 | |
| pMH38 | Ext(4CL50FA46) | <<0.01 | 4 | 50 | 46 | |

According to table 11 above, molecules with very long peptide linker and very short ones have very small production yield and it is possible to detect them but not enough for testing. It shows that the length of the peptide linker do not have certain relationship with production yield of dimer and that it is possible to obtain dimer in some range of the peptide linker length. It can be assumed that the big sized Fab and PE38 may not get disturbed in forming its dimeric structural conformation during refolding even if the length of the peptide linker is long, but this example shows that if the amino acids on peptide linker is increased more than 50, the dimers can be detected but it is not practical to prepare them.

This means that using more than 50 amino acids on peptide linker is not realistic. If the protein production technology develops, the purification of 50 amino acid peptide linker dimer may be possible.

(Purification of B3(Fab)-Ext(4CLFA5X)-PE38)$_2$)

It was analyzed the same as example 1 and the purity was confirmed on PAGE.

(Cytotoxicity Assay)

Cytotoxicity assay was performed in triplicate. The result was that some molecules had same ID$_{50}$ value as monovalent molecule and some had higher cytotoxicity effect than monovalent molecules like in the previous example. This is because of the density and the structural conditions of antigen on cell surface according to the cell type.

Example 7

Dimerization when the Uncoupled Cysteine is on the 25$^{th}$, 35$^{th}$, 45$^{th}$ Position on the Extension Chain(Ext)

The relationship of uncoupled Cys position at 25$^{th}$, 35$^{th}$, 45$^{th}$ position on Ext and dimerization was observed. The uncoupled Cysteine on Ext between binding domain and functional domain can react and be oxidized to form disulfide bond with the naturally coupled Cys of intra-chain and inter-chain disulfide bond of binding domain and functional domain and can cause scrambling of the disulfide bond and ruining the structures of domains to inactivate them. The position of uncoupled Cys is very important factor that plays a role in scrambling the disulfide bond with the naturally coupled Cysteine of binding domain and functional group. Depending on the uncoupled Cysteine position, the disulfide bond scrambling can happen.

Plasmids below were constructed to find out effects on dimerization when uncoupled Cysteines are in different position from previous examples.

pMH42;
B3(Fd)-SKPSISTKAS(GGGGS)2GGGGC(GGGGS)3GGPE (SEQ ID NO: 43)-PE38; Ext(25CL19FA18)

pMH44;
B3(Fd)-SKPSISTKAS(GGGGS)4GGGGC(GGGGS)3GGPE (SEQ ID NO: 44)-PE38; Ext(35CL19FA18)

PMH46;
B3(Fd)-SKPSISTKAS(GGGGS)6GGGGC(GGGGS)3GGPE (SEQ ID NO: 45)-PE38; Ext(45CL19FA18)

The protein chains above have fixed L19FA18 as LFA sequence on Ext(LFA) and the position of Cys is changed to 25$^{th}$, 35$^{th}$, 45$^{th}$. Therefore, it shows whether there are any limits on the position of Cysteine compared to dimers formed previously. When the uncoupled Cys was on the 45$^{th}$ position, detection of dimers was possible but not enough to purify. Accordingly, this example shows that dimerization is impossible if the uncoupled Cysteine is on over the 45$^{th}$ position.

(Apparatus and Method)

The same apparatus and method was used as example 1.

(Materials and Methods)

The same materials and methods were used as example 1.

(Construction of Plasmids)

Protein expression plasmids were constructed by using primers and PCR. Plasmids for templates used were the same as in example 2 and example 6. For the repeated GGGGS (SEQ ID NO: 17) sequence insertion, restriction and ligation was performed using restriction enzymes and ligase.

(Protein Expression and Isolation of Inclusion Body)

The same method was used as example 1.

(Refolding Procedure and Isolation of Protein)

The same method was used as example 1.

(Construction of Expression Vector and Isolation of Inclusion Body)

The cloned nucleotide sequence into expression plasmids made by PCR was confirmed by sequence analysis.

The proteins in the form of inclusion body was analyzed by densitometry analysis(TINA2.0) on PAGE gel and the wanted protein chain was in 21~27% ratio.

(Refolding of [B3(Fab)-Ext(10XC L19FA18)-PE38]$_2$) L19FA18

The production yield of dimer was calculated by the analysis of the sample on PAGE after refolding procedure and ion exchange chromatography. The compared dimer production yield is shown on table 12.

TABLE 12

| Plasmid name | Structure of Ext | Yield of dimer (%) | Position of Cys in Ext | Length of L (distance bet. Cys and F) | Number of GASQEND (SEQ ID NO: 21) in L | Note |
|---|---|---|---|---|---|---|
| pCE1 | Ext(1CL13FA7) | 0.016 | 1 | 13 | 7 | Example3 |
| pMH21 | Ext(4CL15FA11) | 0.18 | 4 | 15 | 11 | Example1 |
| pMH22 | Ext(4CL20FA16) | 0.23 | 4 | 20 | 16 | Example1 |
| pCW1 | Ext(15CL14FA13) | 0.06 | 15 | 14 | 13 | Example2 |
| pMH42 | Ext(25CL19FA18) | 0.12 | 25 | 19 | 18 | |
| pMH44 | Ext(35CL19FA18) | 0.04 | 35 | 19 | 18 | |
| pMH46 | Ext(45CL19FA18) | <<0.01 | 45 | 19 | 18 | |

According to table 12, when the Cysteine is at the $1^{st}$ position (Ext(1CL13FA7)) the productivity is the lowest and when it is at the $4^{th}$ position (Ext(4CL20FA16)), the productivity is the highest. When the Cys is positioned at the farthest (Ext(45CL19FA18)) position, the dimer can be detected but can't be purified because the quantity is too small. If the protein production technology develops, it can be possible.

This example shows there is no definite relation between the position of Cys on extension chain with production yield, and dimerization is possible when the uncoupled Cys is in certain range of position. This means that Cys positioned over $45^{th}$ position is impractical for the production of dimers.

(Purification of [B3 (Fab)-Ext(10XC L19FA18)-PE38]$_2$)

It was analyzed the same as example 1 and the different purity was confirmed with PAGE.

The invention claimed is:

1. A recombinant fusion protein comprising:
   (i) a binding domain that is an antibody that binds to a cell-surface antigen;
   (ii) a functional group domain for eliciting a desired effect on a target molecule, wherein tile functional group is an enzyme; and
   (iii) an extension peptide located between said binding domain and said functional group domain and containing one uncoupled cysteine residue capable of forming a disulfide bond for dimerization, wherein the extension peptide has a sequence represented by (S/A)KPSI(S/A)T(K/Q)AS($G_4S$)$_n$GGPE, which is SEQ ID NO:13, wherein (n) is an integer ranging from 0 to 8, and wherein the amino acid at position 4, 15, 25 or 35 of SEQ ID NO:13 is substituted with said cysteine residue capable of forming a disulfide bond.

2. A covalent homodimer formed between two recombinant fusion proteins of claim 1 connected via a disulfide bond between the uncoupled cysteine residues.

3. The recombinant fusion protein according to claim 1, wherein the binding domain is an $F_{ab}$.

4. The recombinant fusion protein of claim 1, wherein the enzyme is a protein containing a toxin-functional group.

5. The recombinant fusion protein of claim 4, wherein the protein containing a toxin-functional group is *Pseudomonas* exotoxin A.

* * * * *